United States Patent
Hamilton et al.

(10) Patent No.: US 9,708,674 B2
(45) Date of Patent: Jul. 18, 2017

(54) RESISTANCE ALLELES IN SOYBEAN

(71) Applicant: Syngenta Participations AG, Basel (CH)

(72) Inventors: Mark Charles Hamilton, Slater, IA (US); Harish Gandhi, Andhra Pradesh (IN); Ainong Shi, Fayetteville, AR (US); Craig Lynn Davis, Pekin, IL (US); Thomas Joseph Curley, Jr., Research Triangle Park, NC (US); Baohong Guo, Slater, IA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/254,469

(22) Filed: Sep. 1, 2016

(65) Prior Publication Data

US 2016/0362754 A1    Dec. 15, 2016

Related U.S. Application Data

(62) Division of application No. 13/460,826, filed on Apr. 30, 2012, now Pat. No. 9,458,504.

(60) Provisional application No. 61/480,430, filed on Apr. 29, 2011.

(51) Int. Cl.
| | | |
|---|---|---|
| *C12Q 1/68* | (2006.01) | |
| *A01H 5/10* | (2006.01) | |
| *A01H 1/04* | (2006.01) | |

(52) U.S. Cl.
CPC ............ *C12Q 1/6895* (2013.01); *A01H 5/10* (2013.01); *C12Q 1/6881* (2013.01); *A01H 1/04* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 2006/0041951 A1 | 2/2006 | Sebastian et al. |
| 2010/0122372 A1 | 5/2010 | Sebastian et al. |

OTHER PUBLICATIONS

Hyten et al. (BMC Genomics (Jan. 2010), 11:38, pp. 1-8).*
Soybase.org (SNP report for BARC-024383-04865), accessed on internet Oct. 3, 2013.*
Charlson et al., "Molecular Marker Satt481 is associated with iron-deficiency chlorosis resistance in a soybean breeding population," Crop Sci, 2005, 45:2394-2399.
Wang et al., Association mapping of iron deficiency chlorosis loci in soybean (*Glycine max* L. Merr.) advanced breeding lines.
Hyten et al., "High-throughput SNP discovery through deep resequencing of a reduced representation library to anchor and orient scaffolds in the soybean whole genome sequence," 2010, BMC Genomics, 11:38.
Choi et al., "A soybean transcript map: Gene distribution, haplotype and single-nucleotide polymorphism analysis," 2007, Genetics Society of America, 176:685-696.
SoyBase and the Soybean Breeder's Toolbox; Glycine max; SNP name BARC-044655-08749; Chromosome Gm17; Retrieved from the Internet May 20, 2015.

* cited by examiner

*Primary Examiner* — Brent Page
*Assistant Examiner* — Jared Shapiro
(74) *Attorney, Agent, or Firm* — Kevin Markham

(57) ABSTRACT

The present invention relates to methods and compositions for identifying, selecting and/or producing a soybean plant or germplasm having iron deficiency chlorosis tolerance. A soybean plant, part thereof and/or germplasm, including any progeny and/or seeds derived from a soybean plant or germplasm identified, selected and/or produced by any of the methods of the present invention is also provided.

8 Claims, 1 Drawing Sheet

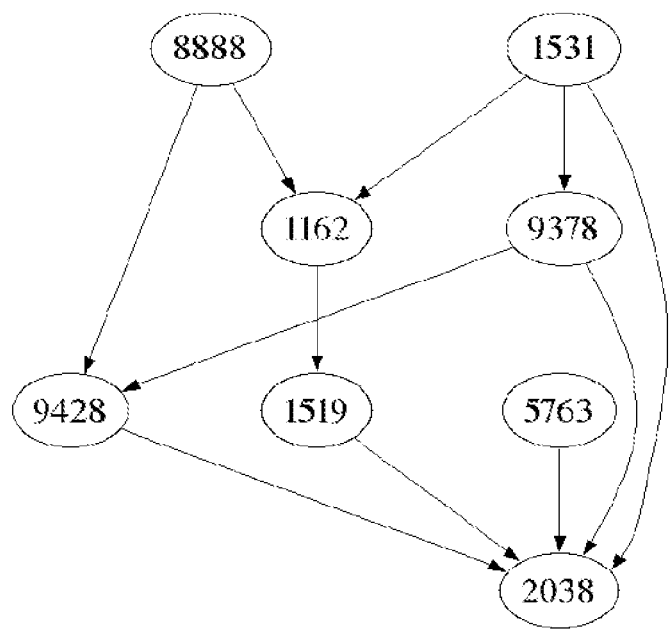

SEQUENCE LISTING

```
<160> NUMBER OF SEQ ID NOS: 367

<210> SEQ ID NO 1
<211> LENGTH: 1174
<212> TYPE: DNA
<213> ORGANISM: Glycine max
<220> FEATURE:
<221> NAME/KEY: misc_feature
<222> LOCATION: (125)..(125)
<223> OTHER INFORMATION: n is a or g
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
```

<400> SEQUENCE: 1

```
gccctcccat catccagcac cggcactcac aacgatctca accccctttt accaagggct    60
ttcatgtctt ctaagaaagc cgtatctttt tcatcaatgc tctgtgtttt tggagctgat   120
gacangctca ccgactctga tttcacaata gttggtccag atgtaccaga gactgcccta   180
gaggttgaca ctgccggttt tggctttgtt ttagacattg ccgcttctct tctcactcgc   240
acagatgcag gaacctagcc aaaaacaaga tatagactca attagagaat atatacaaag   300
agattgaaat aataacaagt gatgccagtt ttaagttctc aatcataaac agntcagata   360
tatgttanat taacttattt aacagctatc tttcctcatg attcaactca cagataacac   420
ttcttccgtt aagaaaatat gtcccataca agtaaatgca caataaatca tttagttgtt   480
attagtttgg tttatataat cactacatac cgtagcaaca aacaattacc accagactaa   540
attacagaat gatggcatta gcttctttcg agttcaggaa agcttataat canaacacta   600
aaaacttcgt accccattgc ccagaggctc ttcgctatgc gaaggtatgg gggagggata   660
ttgtacgcag ccttacccct gcatatgcaa agaggctgtt tccggatttg aacccatgac   720
caacaagtca ccaaggcaca actttaccgc tgcaccaggg ctcgccctcc ttataatcaa   780
aaccctgttg aaagaaattt ttacttgaaa aactcttccg ttatagaatt aagccaaaaa   840
caaacaagta atagagatcc ctaaaagaag aaaaaattaa gagcccatat aaaaagaagt   900
gcaaaaaaaa aaaaatcctc aacttaccat ggctgttagt tctggagtgt gttgagctaa   960
tggccttta acaacagtag aagcagcaga tttaacatat gatggtttcg gaggaggagg  1020
aggtggccta gttgctatat gatcctcttc ctggaagttt ggaggaggac caggaggaag  1080
tggaggtctc atcattggag gaggaccagg tggaggacca ggtagaggaa aaggggtgg   1140
ccttggcatt aggggaccc atcattccagg aggt                               1174
```

<210> SEQ ID NO 2
<211> LENGTH: 1211
<212> TYPE: DNA
<213> ORGANISM: Glycine max
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (300)..(300)
<223> OTHER INFORMATION: n is a or g
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (584)..(585)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t

<400> SEQUENCE: 2

```
aggtacacaa attagtctta ccttcatttc tcagataatt naattcttca aatcaagttc    60
tttttgttaa cgttagtttg tatccactta aagatgagag tgacgatttt ttcttttttct  120
```

```
tttgttattg ttattttgtc ttgtacaggt ttcatctgat gttaacatag aaaaggagca      180
agatgaagaa tttcgctttc ctgttgacca tgnatgttat ttattttttt ccttggcaaa      240
aatattagtc aaaatatttc ttaaattctg tgattttctt atgtgcttga tgtaaccgtn      300
tatgtcataa tatccttact ggaaatatga aattctcttc agcttatcgt gagaggcggg      360
aacagaaggc taatgcagga cataggtaag caaaacagag tattttggat gctttattag      420
gttaactttg atctngtgct tccggtttta agttttaagc atgagtactc cattttgcat      480
tttcaccaat gtatatatat catatataca taaaaatcct ctagaatcaa cctagtgggt      540
tttcgtatag catacccaaa attttatctt caagaatgaa aatnnaaata aggtataatt      600
atttatttga tttntatatc ttagatttca acttaaaatc aatgtgagac ttggatattt      660
cccaacacta tatatgtatc ctcttttgag tttttagtcta tatatttaaa aattacctga    720
tttatgtctc taaacatatt ttttaaaatc tattttaatc attacacata catttttta     780 tctttaaaca agtagtaaat tgctttatgt atttggatca aatgagttga gttattaaat    840
cttaaaataa ggaaatggtt tttgatatat ttgtttgggg ttcatcttct tgttgtttaa    900
tggaggatcc attaggaaag agataaacac aaacatgggg aatcggagac ccaccagtag    960
atatttttcc atttgtttgg tggtgattaa ctatgattat gcagattgtg gaggattgtg   1020
caagacaagg tgcagtgccc attcaaggcc aaatgtgtgc aacagggctt gtggcacatg   1080
ttgtgtgagg tgcaagtgtg ttccacctgg aacttccggc aacagggagc tttgtgggac   1140
ctgctatact gatatgacca cccatggtaa caagaccaag tgcccgtaaa gcccatagaa   1200
ggtgagccct a                                                        1211
```

<210> SEQ ID NO 3
<211> LENGTH: 240
<212> TYPE: DNA
<213> ORGANISM: Glycine max
<220> FEATURE:
<221> NAME/KEY: misc_feature
<222> LOCATION: (100)..(113)
<223> OTHER INFORMATION: cacacctagctaat sequence is present or absent
<220> FEATURE:
<221> NAME/KEY: misc_feature
<222> LOCATION: (237)..(237)
<223> OTHER INFORMATION: n is a, c, g, or t

<400> SEQUENCE: 3

```
cgctgtggga cctgctatac tgatatgacc acccatggta acaagaccaa gtgcccgtaa       60
agcccataga aggtgagccc tatccaattg ggcccttcac acacctagct aatcacacca      120
agcaaagcta gcatagttta gtaaataata aatgtgttat ctacactttt gtagatttgg      180
atttgtcatc tttaagatgt gttctagttt ttatctttgt tataaaggta tggtacnata      240
```

<210> SEQ ID NO 4
<211> LENGTH: 613
<212> TYPE: DNA
<213> ORGANISM: Glycine max
<220> FEATURE:
<221> NAME/KEY: misc_feature
<222> LOCATION: (309)..(309)
<223> OTHER INFORMATION: n is a or c
<220> FEATURE:
<221> NAME/KEY: misc_feature
<222> LOCATION: (366)..(366)
<223> OTHER INFORMATION: n is a, c, g, or t

<400> SEQUENCE: 4

```
tgttaacacc caggttggta atggttatgt tccatctttt ttgcttttcc ttgctgacag       60
```

```
ctatattggc ttaactgctc agtttttac tggtttttat tctgtatatc tgtgaaggtc      120
cttgctttca atggtcaacc agtgaaaaac ctgaagagcc tagccactat ggtagagagc      180
tgcaatgatg aatatctaaa atttgatcta gattatgatc aggttcactt gccatccttc      240
cccgttttat gtgcttgtgt gaaaatggca gtagccttat taactaacta atcctcttat      300
atgcagatng tggtgcttcg catgaagact gcaaaagcag ctactcttga tattcttgca      360
acgcantgta ttccatcagc aatgtctgat gatcttaagt catgatatga atcacaatgt      420
agtagattct gcatcatgat cttaagtcat tatattttta gttagattgt ttccctacat      480
ggtactggga gttatgttta atttaagtgc taatgcctct tgggactctg atggttccac      540
attttgaaag agatgataga taggtaagca ggatttacat tacaattcat tgtcttctga      600
tacattggcc ttt                                                          613

<210> SEQ ID NO 5
<211> LENGTH: 276
<212> TYPE: DNA
<213> ORGANISM: Glycine max
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (187)..(187)
<223> OTHER INFORMATION: n is a or t

<400> SEQUENCE: 5
cgccgaggta tgtggaaaag gccactaagt ttgtgaagcc caaggtgagc ccacgggcta       60
ttcaccagcc caggtagacg ccacccggcc cattccccca ncaccaccag ctatgtacat      120
aaaaaaaaan aagtgtcaag cgcaatgact tcgtctttag agctttcttt acattttcca      180
gattttnatt ttcgtgttga tcttcttgtt actctgatgt tccataaaga taaactcaag      240
tttctttgat gatgatattt gcgacgcctg taagtt                                276

<210> SEQ ID NO 6
<211> LENGTH: 579
<212> TYPE: DNA
<213> ORGANISM: Glycine max
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (500)..(500)
```

<223> OTHER INFORMATION: n c or g

<400> SEQUENCE: 6

| aatgcagcga | tagtggcttc | cgttcttctt | taccttcgct | ttgtagatgt | aagccatgcg | 60 |
| cttcccacag | taccacgcaa | cttcttcctt | agagtttaca | ttctcaatct | ggattaggga | 120 |
| ggtgcttggg | tattgatttg | acttggacct | gaacaacacc | accatnaatc | aatatcaata | 180 |
| tccaatacac | ggcacagatt | gaaactattt | atgagaaaat | caataaacct | aatactgtng | 240 |
| tttattgtac | aatctccaga | aaacctttaa | attaattaat | aataaataaa | acgcacctct | 300 |
| tgtatccaag | aattgaaccc | ctgacgtaga | gtctggtaaa | aacaagaaaa | acaacgataa | 360 |
| cgttaacaaa | tattcatgat | atgtgcatta | cgcatgttgt | acnaacaact | gctaaaattt | 420 |
| gtgaaaatca | aantattatt | aggagacact | aaacccanag | attaaaagcg | atgccataaa | 480 |
| catagcaaat | gaaaggaaan | agtaagatcg | caaaccttac | acgttctcct | tggcgacctt | 540 |
| taaccattgt | ggcaatggtg | atgcctcctg | ctcctcttc | | | 579 |

<210> SEQ ID NO 7
<211> LENGTH: 408
<212> TYPE: DNA
<213> ORGANISM: Glycine max
<220> FEATURE:
<221> NAME/KEY: misc_feature
<222> LOCATION: (255)..(255)
<223> OTHER INFORMATION: n is a or g

<400> SEQUENCE: 7

| tccgctgaga | tcagaaggat | tgagttggaa | gaagtggaaa | atgctaaggc | taaagccaaa | 60 |
| aactttagag | ggtttaggat | ggaggtaatg | gatgtaacaa | aattagcttt | gttaagacca | 120 |
| gatggtcatc | ctggtgctta | tatgaatcct | tttccattcg | ctaatggggt | tccaaagcgt | 180 |
| gtgcagagtg | attgtgttca | ttggtgtttg | ccaggaccta | tagacacatg | gagtgagatt | 240 |
| tttctccaga | tgttngaaaa | catggcacga | gcagccaagg | agtgaagagt | gaagcattct | 300 |
| tcatatccgt | taattcattt | gcaataattt | tttcgccaca | catgtgatgt | gttgcgtcaa | 360 |
| aactagaaag | agtattttgt | tattttgttt | gtgtgtaggt | tgggctaa | | 408 |

<210> SEQ ID NO 8
<211> LENGTH: 770
<212> TYPE: DNA
<213> ORGANISM: Glycine max
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (330)..(330)
<223> OTHER INFORMATION: n is a or t

<400> SEQUENCE: 8

| gcaagcacat | gcatcaaaca | aaagtttgct | aaactgctaa | acgaagttcc | acaatgtcaa | 60 |
| taatgtaaat | cactagcaac | tgaatccatc | atctacaact | catttcatga | aataaaagtt | 120 |
| gctctacatt | gtcatcttga | agctcttatc | ccactnttca | ttgatggatg | gaccaatcca | 180 |
| gtaaaaggat | gaatgccgac | agccacattt | gctccttcaa | tcccatgaaa | atatttttca | 240 |
| atttgtttta | gaaccaatct | tcctcttagc | aaaagatggc | aancagaaag | ccgctgtatg | 300 |

```
aatctgaaat agaaaacaga caaaatatan gagtcaagta agaaaaatca gtcggatgtt      360
ttgaagttag tggaaaaaga acatggtcgg agcaacaaac ctcagagttg taaaatttca      420
atggtcttga ttgctgacta tcattctcat ttataggatt cactggatgc ttgaaatcaa      480
caagaggacc ctcagttgag caaagcataa aaccaatcat cccactgaaa tggaaataat      540
caaaaccaac ataaatatgg ttaataatat aaattctaaa cataggacta tgttttgaag      600
actgcaatgc aaatgggaaa ataatatttg aaagggcata ccttgggtat gtaggaactg      660
tggtccatgc atagttgata gaacctttga atatttggcg acaattagcc acaatgtcct      720
caatgatgtg catatgaagc catatacttt ctgcttgagt acacacaact                 770
```

<210> SEQ ID NO 9
<211> LENGTH: 763
<212> TYPE: DNA
<213> ORGANISM: Glycine max
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (549)..(549)
<223> OTHER INFORMATION: n is a or g

<400> SEQUENCE: 9

```
aactgttaat tcaacaaaaa taatgtatgt catttttttt ctcctttaag ctataatttg       60
acatctaaac aaggtcggcc ataaaatttc gtgaacttct tctgcaaaaa ctggtcttcg      120
gctttaaaac cctcttcacc taagataggt cgatgaaacc cataatagaa catatgttat      180
cagtgatgag atcacttcaa atgcccttgg tcccttaagt atggtaatag gaggaattac      240
tgacaccatc aagaaggttc ccaacagcca cgaaatacca aatgctccaa ccctgcanca      300
aagcatcatg tcatataagt aaaagcctaa agaaaaaaac cactaatgca acaaattcta      360
aagaaagggc acaatgataa tatgatatta acatcngaat gtaacaccat gggaatgtga      420
tgcttttaaa tgaaaaataa caaatcacga tctaacacta tatattctaa acatatttga      480
aagaataaga cgcattgtat gtacccatat agcgaagctc gtatgttgct cttcagccgt      540
tcatggatna aatatattgt ggcgatcaga gatattgcta cctgaagagt tggcccttct      600
tcagttggaa agaggacagt caaaactcca agtaccaaga atgctattga agttttata      660 atgaattttg tagatggagt ttgaaatctg cctctgacag cctgcacaaa tttggattga      720
ttgacttccc tcattttttt cttaatgtca attttggggt ttt                       763
```

<210> SEQ ID NO 10
<211> LENGTH: 1436
<212> TYPE: DNA
<213> ORGANISM: Glycine max
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (955)..(955)
<223> OTHER INFORMATION: n is a or g

<400> SEQUENCE: 10

```
tcatttttt   gccgtcagag  accagcaatt  tgctgtctac  gccgttaaga  aacaaaaaag      60
aacctagcaa  atacaatca   accccttac   aaaattncat  caatcgttaa  tgactaagat    120
gtcgctcaca  acgccgagaa  gcaccaagta  gaatagaagt  attctgatag  gtggcaatat    180
tagcatatct  ctacacaggc  cttcaatcta  acgcgtgttg  aagattgctt  cctagctaga    240
catcatgaca  tgatccattg  cgtgaagtgc  ttgattggaa  aaaaatctta  catcaacatc    300
aggatcctcg  ctgagctcaa  ccagacttgg  acgaatcgtc  ttctccacaa  cctaaatgga    360
aacgagattc  acagaataag  attgaaaaac  aaaaggaag   aaaacaaaga  aagggggatat   420 aaagaaaaca  gaaaggacaa  taatgttta   tcataataca  atataagctt  gtgatgctta    480
gttgcttaca  gattgatcca  ctatggggaa  gattgactcc  aagacctttg  ccacattgaa    540
cttaatgttg  ggtactctac  aagggataca  acaggcagca  gttagaaagg  taattaaaac    600
attactcttt  accataatca  cactaaaaaa  actaaaatac  ctgtctttag  atgcagtaat    660
aacaataggc  aataattctg  aacgagtgat  ttcagagccc  atcacaggag  caagtagaga    720
gatagcatgg  agtatggtca  ttcgatacaa  atagtgagga  ttgctaatca  tctccaaaac    780
ctgtttcatg  catgccaata  tgttagtcgt  tacttgtaag  ttatgtttgg  tagatcaact    840
taaatggtaa  cagtatatta  gattaaaagc  aaatattaca  atatgcatct  tagaccttgg    900
aaaaagggga  gggggggca   tataacaagc  tcaaggaag   ttggttcagt  tcagntaatc    960
aggttaagca  ccaaaaattg  ccaaatattt  gttttggaaa  atgaaatcac  taaaatagtt   1020
ccccataaaa  gccctaacac  atctgttcat  agtgccacta  tcctgactga  cagccaatac   1080
tccgtccatg  acaaccgccc  caccaaatcg  gccactgtag  tagcaagggg  ccattccccc   1140
actatagtgt  gctatttacc  ctagcttatg  tagttatcta  agtatcagtt  tgctttagat   1200
tttggtaaaa  ttgattttga  accattaaat  gtgattgaga  tgtgtgccca  tttagccagt   1260
gtgaaattca  ttttggtagt  aaatcaaatg  gaccataaaa  ctgttctttg  ttaattcaca   1320
gctcacattg  taaacaatga  aatgtaccca  cataaaatta  aaaggcaatg  caaggatagg   1380
aaattcaagt  agaagatata  aaaagatcca  acacaaacac  attcatatag  gcatag       1436
```

<210> SEQ ID NO 11
<211> LENGTH: 628
<212> TYPE: DNA
<213> ORGANISM: Glycine max
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (256)..(256)
<223> OTHER INFORMATION: n is a or g
<220> FEATURE:
<221> NAME/KEY: misc_feature
<222> LOCATION: (450)..(450)
<223> OTHER INFORMATION: n is a, c, g, or t

<400> SEQUENCE: 11

```
gcagttgata  gcaagtagct  aaacatcaca  aaatgcctgc  agattgttgc  taatagctat     60
aaaaactaac  atttggagcc  tcttattgaa  caagcaaaac  agattctagg  tgtgaaanta    120
aacacagaaa  tttggaaaca  aatgctagtt  gaagtgaaaa  tgatcatcta  gactcatgtg    180
tctacatgtg  tgtagtgttg  ctgctcaaaa  tttactaact  ttcactgctc  tctagtctta    240
gttcagatgt  agcttntttc  atttgaagat  gatagctctt  atgttatgcc  ggtgcacttg    300
attgggccag  ttttttgaac  tgcaccaaaa  tcatggtcat  gttatcacat  ccatcaccaa    360
```

```
cagtaattgt tggtgccaaa cattgatcta gtactctttc gcaaacggca gaaagtttag    420
tttcctgtga tgagataaaa tggtatcatn ttcaaaacat ctgctttatg gatcagctaa    480
aaccacattg aaataataac ttggatcatt aacctacaga gtgtgtattc cactgtttgg    540
cattggcata ggtagctaaa aaactagttg atagcttaaa agctagctga aaactaaaac    600
actactgaga gttgaaaaga taccccag                                      628
```

```
<210> SEQ ID NO 12
<211> LENGTH: 515
<212> TYPE: DNA
<213> ORGANISM: Glycine max
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (50)..(55)
<223> OTHER INFORMATION: cttacc sequence is present or absent
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (87)..(89)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 12
gcgaagggtc ctcgttgcgt aaaaatatgg ganagaatta ttgtanngtc ttacccttac     60
ccttacatat gtaaaaggan tattttnnna ttcgaaccna taatcaactc cttaccaagg    120
cacaacttta tgactaaaaa aataaaaatt cataagtgca tcagcaggaa gaaaaaaaat    180
tcaggaattc cccatatcat attactccag atacatgaat ttaacccaat gaaaatccac    240
aatcatcaaa cacaaagag gcagtgaatt acacaatgaa atctacaaca gagagagaga    300
caatggatct ggaaactaat gaagggtacc ctgaattaag ttgtagcagc cagagtatgt    360
gactgagaac tgaactgaac tatgatcact atgtgactat ttccacagga tacttatgaa    420
tgcaatcttc ccatggtcca ttaggagaag gcctcacatt cctcagagcc tgccaaaccg    480
cactgttaca cttgaaacca cttccaaacg cagcc                              515
```

```
<210> SEQ ID NO 13
<211> LENGTH: 492
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
```

```
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (279)..(279)
<223> OTHER INFORMATION: n is c or g
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 13
atcaaggtct acaaagcaga cacatgtgac atgtaactat atacaaaata tcacgaataa      60
ctccagcagg acctaatccg acatgattgt tacatacaaa cantacaatc acttaacgaa     120
caacaaaact ntaccagaca tgatccaaaa catccttagg cacccaaaag gaatgtaagc     180
tcnaactcta acnttgaaag gtcagaagga gttataagac tcaccagagt cactagacag     240
tggagagtta cgaggagaac ccccaatacc acctacatna ctactatcaa aacctatggc     300
ttcaagccaa aaactaatcc agggtgattc agatgtgtca cctttcatga agatattgac     360
ctgcatgtta agagctcncc gcctcctggg tgtgatatgc tcttggttaa ggacattatg     420
gggctcccta tgtcccgtnc gatttntgtt cagttttcct gggcattaag ccctcctcag     480
aataaaaaaa ag                                                         492

<210> SEQ ID NO 14
<211> LENGTH: 778
<212> TYPE: DNA
<213> ORGANISM: Glycine max
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (336)..(336)
<223> OTHER INFORMATION: n is a or g
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t

<400> SEQUENCE: 14
ggcagtttgt ttcacttaca gctcttggtt tgcacttgga ggtctatttg cttttagact      60
tataaaaatt gtgttactat tcgtagagct gtgaaatttc tactcaaaat acanaataag     120
gatggtgggt ggggagagag ttatctttct tgcccaagga aggtttgtaa ttaaatgatt     180
attttgtggt aatagtttag ttaaacttta atgctaatta taagtaatat tattaataat     240
gtcttaatga atgtatgtgt ataatgaaaa tgtacgtacc tcttgaagga agtcgaacaa     300
atattgtaca aacagcttgg gctttaatgg ctctanttca tgttgattgt atcttttgac     360
gtgcacgtgt gtgagactac atgtccattt gattgtatct tggatttcaa cttgtttatt     420
tattactatt actatatcca aaataaatgt tatataattg tttttcttct tccttttta     480
```

```
attttgtata taggtcgaga gagatccaac tccccttcac aatgcagcaa agttactcat    540
taattatcaa tgagaagatg gcgattgggc ccgacaagta cctctcaaat ctcaatcttt    600
tgaattcaat agtntgacta tgatcaatct taantttcat ttttaattct tgtttaattt    660
gacttattta tggcatgaaa ctcttggagt atacttgaga aattgcttgg ttcattacgt    720
acccattcta tatatagaaa tgttttccca atatgggctt tggctgaata tcgcacaa     778
```

<210> SEQ ID NO 15
<211> LENGTH: 620
<212> TYPE: DNA
<213> ORGANISM: Glycine max
<220> FEATURE:
<221> NAME/KEY: misc_feature
<222> LOCATION: (477)..(477)
<223> OTHER INFORMATION: n is a or g

<400> SEQUENCE: 15

```
cttcccttct cttaatataa ttttgagata aatatcgctg tcattaaaaa atgtatctag     60
ctgtgtaatt ggaaaaagaa tttgtaattg actatgaatc atcctaattt tactttgcat    120
gagctatctc accagacttg tacattcttg ctcgtcttga atattcttgg atctttcgat    180
cacgctcttt gagcatctga tccatgttgt ttgatgaaag cagtaatgga ccagagaggt    240
ggtagatatt gtttcccatg gatccatgcc catcctgaaa tagggaccag catcaataac    300
cagcaaaacc ttaagataaa taataaatgc atacaaatta cgaaaatgtg gcaaactagg    360
gacacaaaaa gcaagatttt gtcgttgttg atggctaaca aagccattca ctaacatatg    420
ctgacaatca cgaaagcaga aagacgatag aaattggaag gaaacgatac taatagncaa    480
aactaacctg aattaatgtt tcagttgaaa attttccatt ttcgatttgc ctgggatcaa    540
ttgtctgaga atggcgtttt ttatcatgcc ttcttcttga ctctgatcca ttagttgact    600
cctgtacttg aattgtttct                                               620
```

<210> SEQ ID NO 16
<211> LENGTH: 544
<212> TYPE: DNA
<213> ORGANISM: Glycine max
<220> FEATURE:
<221> NAME/KEY: misc_feature
<222> LOCATION: (449)..(449)
<223> OTHER INFORMATION: n is a or g

<400> SEQUENCE: 16

```
atccactgca catgtaacac tcttacaaag catttccttc acgaaccttt taaaagaaaa     60
aaaaaaatac ttgcaagctc agaaaaacac ctttcaatat atttcaagac taaaaaatcg    120
gtaatgattt tcaagcaata ttggggtatg gtttaataat aatagtataa tctatatata    180
tgaaggcaaa cattatgcag cttgcttgag cttctttgtg atgccggcaa tgtacttgcc    240
ttggtggaat gcttgctgta actcaagctc acttggctgt cttgagccgt caccggcata    300
agttccggca ccatatggac ttccaccttt cactttctcc atctcgaaca tgccagcacc    360
aaacgtgtaa ccgattggaa tgaatatcat cccatgatga accagttgag tgatagcagt    420
gagcctgtca tggattccac atgttaatnt tggatacatc tttggtcgcg caataagaaa    480
ccaagcacta agatagaagg ggcgcttacg ctgtagtctc ttgtccgccg ccttgtaacc    540
agtg                                                                544
```

<210> SEQ ID NO 17

```
<211> LENGTH: 450
<212> TYPE: DNA
<213> ORGANISM: Glycine max
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (86)..(86)
<223> OTHER INFORMATION: n is a or g
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t

<400> SEQUENCE: 17
tatgttttat tcagggtcac cgggcctatg cgggncacaa gaaatatata acaccaaaca      60
aaagacagat gctcccctat tttctnaatt cttccctccc tgaaaaagag ttcaatagga     120
ttatcaagga attgcatcag gattcattag gtcagccaga actcaggact agcaagtctg     180
ggagggatgt caccaagtat cctgttcctg agtgcatgtg caatgatgac tctcatcatc     240
attcttccta aattgcacat ttgataccaa agcttttggt gtgaagatta cncgaaaatg     300
gataaacaaa cacggaagcg atgctacgag tatgattttg atcccttgcg aattttgctt     360
gaaaggtcat ttcctcagaa accacanttc ttaagagcac catcttttaa gagccataat     420
gtcaagcatg cctatcccta catggtgtat                                      450

<210> SEQ ID NO 18
<211> LENGTH: 605
<212> TYPE: DNA
<213> ORGANISM: Glycine max
<220> FEATURE:
<221> NAME/KEY: misc_feature
<222> LOCATION: (194)..(194)
<223> OTHER INFORMATION: n is a or g

<400> SEQUENCE: 18
agtaggaagg tagttgaaat tctccagcaa gaaaatgttc cctttgagag ttttgacatt      60
cttactgatg aagaagttcg tcaagggctt aaggtttatt caaactggtc cagttatcct     120
caactgtata tcaagggtga gcttattggt ggatcagata ttgtgttgga gatgcaaaaa     180
agcggagaac ttangaagaa tttacacgag aaagggattc ttcctgcaga gaccattcaa     240
gatcgactga agaatttgat tgcctcgtcc cctgtgatgc tgttcatgaa gggtacccca     300
gatgcaccaa gatgtggttt tagttccaga gttgctgatg cccttcgaca agagggcttg     360
aattttgggt cctttgatat attgactgat gaggaagtga gacagggatt gaaggtatac     420
tcaaattggc caacctatcc tcaactctac tacaaaagtg agctgattgg tggtcatgat     480
attgtgatgg agctgcgaaa taatgggag ctgaagtcga ctttatctga gtaggattat     540
tattattcct tcaaataaca tgtgttatgt cctagaagcc attttgggag ttgtgttttt     600
gatgt                                                                 605

<210> SEQ ID NO 19
<211> LENGTH: 15
<212> TYPE: DNA
<213> ORGANISM: Artificial
<220> FEATURE:
<223> OTHER INFORMATION: SNP probe sequence
```

<400> SEQUENCE: 19
agtcggtgag cctgt                                                    15

<210> SEQ ID NO 20
<211> LENGTH: 18
<212> TYPE: DNA
<213> ORGANISM: Artificial
<220> FEATURE:
<223> OTHER INFORMATION: SNP probe sequence

<400> SEQUENCE: 20
tgcttgatgt aaccgtat                                                 18

<210> SEQ ID NO 21
<211> LENGTH: 17
<212> TYPE: DNA
<213> ORGANISM: Artificial
<220> FEATURE:
<223> OTHER INFORMATION: SNP probe sequence

<400> SEQUENCE: 21
ctaggtgtgt gaagggc                                                  17

<210> SEQ ID NO 22
<211> LENGTH: 15
<212> TYPE: DNA
<213> ORGANISM: Artificial
<220> FEATURE:
<223> OTHER INFORMATION: SNP probe sequence

<400> SEQUENCE: 22
cgaagcacca cgatc                                                    15

<210> SEQ ID NO 23
<211> LENGTH: 20
<212> TYPE: DNA
<213> ORGANISM: Artificial
<220> FEATURE:
<223> OTHER INFORMATION: SNP probe sequence

<400> SEQUENCE: 23
acattttcca gattttaatt                                               20

<210> SEQ ID NO 24
<211> LENGTH: 16
<212> TYPE: DNA
<213> ORGANISM: Artificial
<220> FEATURE:
<223> OTHER INFORMATION: SNP probe sequence

<400> SEQUENCE: 24
ttgcgatctt actctt                                                   16

<210> SEQ ID NO 25
<211> LENGTH: 18
<212> TYPE: DNA
<213> ORGANISM: Artificial
<220> FEATURE:
<223> OTHER INFORMATION: SNP probe sequence

<400> SEQUENCE: 25
ttttctccag atgttaga                                                 18

<210> SEQ ID NO 26

```
<211> LENGTH: 19
<212> TYPE: DNA
<213> ORGANISM: Artificial
<220> FEATURE:
<223> OTHER INFORMATION: SNP probe sequence

<400> SEQUENCE: 26
ttcttacttg actcatata                                                   19

<210> SEQ ID NO 27
<211> LENGTH: 18
<212> TYPE: DNA
<213> ORGANISM: Artificial
<220> FEATURE:
<223> OTHER INFORMATION: SNP probe sequence

<400> SEQUENCE: 27
agccgttcat ggataaaa                                                    18

<210> SEQ ID NO 28
<211> LENGTH: 19
<212> TYPE: DNA
<213> ORGANISM: Artificial
<220> FEATURE:
<223> OTHER INFORMATION: SNP probe sequence

<400> SEQUENCE: 28
tggttcagtt cagataatc                                                   19

<210> SEQ ID NO 29
<211> LENGTH: 19
<212> TYPE: DNA
<213> ORGANISM: Artificial
<220> FEATURE:
<223> OTHER INFORMATION: SNP probe sequence

<400> SEQUENCE: 29
tcttcaaatg aaacaagct                                                   19

<210> SEQ ID NO 30
<211> LENGTH: 20
<212> TYPE: DNA
<213> ORGANISM: Artificial
<220> FEATURE:
<223> OTHER INFORMATION: SNP probe sequence

<400> SEQUENCE: 30
atgtaagggt aagggtaaga                                                  20

<210> SEQ ID NO 31
<211> LENGTH: 18
<212> TYPE: DNA
<213> ORGANISM: Artificial
<220> FEATURE:
<223> OTHER INFORMATION: SNP probe sequence

<400> SEQUENCE: 31
aataccacct acatcact                                                    18

<210> SEQ ID NO 32
<211> LENGTH: 19
<212> TYPE: DNA
<213> ORGANISM: Artificial
<220> FEATURE:
<223> OTHER INFORMATION: SNP probe sequence

<400> SEQUENCE: 32
```

```
ctttaatggc tctaattca                                                19

<210> SEQ ID NO 33
<211> LENGTH: 18
<212> TYPE: DNA
<213> ORGANISM: Artificial
<220> FEATURE:
<223> OTHER INFORMATION: SNP probe sequence

<400> SEQUENCE: 33
caggttagtt ttgcctat                                                 18

<210> SEQ ID NO 34
<211> LENGTH: 17
<212> TYPE: DNA
<213> ORGANISM: Artificial
<220> FEATURE:
<223> OTHER INFORMATION: SNP probe sequence

<400> SEQUENCE: 34
tgtatccaac attaaca                                                  17

<210> SEQ ID NO 35
<211> LENGTH: 19
<212> TYPE: DNA
<213> ORGANISM: Artificial
<220> FEATURE:
<223> OTHER INFORMATION: SNP probe sequence

<400> SEQUENCE: 35
cagggaggga agaattcag                                                19

<210> SEQ ID NO 36
<211> LENGTH: 19
<212> TYPE: DNA
<213> ORGANISM: Artificial
<220> FEATURE:
<223> OTHER INFORMATION: SNP probe sequence

<400> SEQUENCE: 36
cgtgtaaatt cttcctaag                                                19

<210> SEQ ID NO 37
<211> LENGTH: 16
<212> TYPE: DNA
<213> ORGANISM: Artificial
<220> FEATURE:
<223> OTHER INFORMATION: SNP probe sequence

<400> SEQUENCE: 37
agtcggtgag cttgtc                                                   16

<210> SEQ ID NO 38
<211> LENGTH: 18
<212> TYPE: DNA
<213> ORGANISM: Artificial
<220> FEATURE:
<223> OTHER INFORMATION: SNP probe sequence

<400> SEQUENCE: 38
ttgatgtaac cgtgtatg                                                 18

<210> SEQ ID NO 39
<211> LENGTH: 16
<212> TYPE: DNA
```

```
<213> ORGANISM: Artificial
<220> FEATURE:
<223> OTHER INFORMATION: SNP probe sequence

<400> SEQUENCE: 39
ttgcttggtg tgtgaa                                                    16

<210> SEQ ID NO 40
<211> LENGTH: 17
<212> TYPE: DNA
<213> ORGANISM: Artificial
<220> FEATURE:
<223> OTHER INFORMATION: SNP probe sequence

<400> SEQUENCE: 40
atgcgaagca ccactat                                                   17

<210> SEQ ID NO 41
<211> LENGTH: 20
<212> TYPE: DNA
<213> ORGANISM: Artificial
<220> FEATURE:
<223> OTHER INFORMATION: SNP probe sequence

<400> SEQUENCE: 41
tacattttcc agatttttat                                                20

<210> SEQ ID NO 42
<211> LENGTH: 16
<212> TYPE: DNA
<213> ORGANISM: Artificial
<220> FEATURE:
<223> OTHER INFORMATION: SNP probe sequence

<400> SEQUENCE: 42
ttgcgatctt actgtt                                                    16

<210> SEQ ID NO 43
<211> LENGTH: 16
<212> TYPE: DNA
<213> ORGANISM: Artificial
<220> FEATURE:
<223> OTHER INFORMATION: SNP probe sequence

<400> SEQUENCE: 43
ttctccagat gttgga                                                    16

<210> SEQ ID NO 44
<211> LENGTH: 19
<212> TYPE: DNA
<213> ORGANISM: Artificial
<220> FEATURE:
<223> OTHER INFORMATION: SNP probe sequence

<400> SEQUENCE: 44
ttcttacttg actcttata                                                 19

<210> SEQ ID NO 45
<211> LENGTH: 17
<212> TYPE: DNA
<213> ORGANISM: Artificial
<220> FEATURE:
<223> OTHER INFORMATION: SNP probe sequence

<400> SEQUENCE: 45
agccgttcat ggatgaa                                                   17
```

<210> SEQ ID NO 46
<211> LENGTH: 18
<212> TYPE: DNA
<213> ORGANISM: Artificial
<220> FEATURE:
<223> OTHER INFORMATION: SNP probe sequence

<400> SEQUENCE: 46
ttggttcagt tcaggtaa                                                 18

<210> SEQ ID NO 47
<211> LENGTH: 21
<212> TYPE: DNA
<213> ORGANISM: Artificial
<220> FEATURE:
<223> OTHER INFORMATION: SNP probe sequence

<400> SEQUENCE: 47
tcatcttcaa atgaaataag c                                             21

<210> SEQ ID NO 48
<211> LENGTH: 19
<212> TYPE: DNA
<213> ORGANISM: Artificial
<220> FEATURE:
<223> OTHER INFORMATION: SNP probe sequence

<400> SEQUENCE: 48
acatatgtaa gggtaagac                                                19

<210> SEQ ID NO 49
<211> LENGTH: 17
<212> TYPE: DNA
<213> ORGANISM: Artificial
<220> FEATURE:
<223> OTHER INFORMATION: SNP probe sequence

<400> SEQUENCE: 49
taccacctac atgacta                                                  17

<210> SEQ ID NO 50
<211> LENGTH: 18
<212> TYPE: DNA
<213> ORGANISM: Artificial
<220> FEATURE:
<223> OTHER INFORMATION: SNP probe sequence

<400> SEQUENCE: 50
tttaatggct ctagttca                                                 18

<210> SEQ ID NO 51
<211> LENGTH: 19
<212> TYPE: DNA
<213> ORGANISM: Artificial
<220> FEATURE:
<223> OTHER INFORMATION: SNP probe sequence

<400> SEQUENCE: 51
ttcaggttag ttttgtcta                                                19

<210> SEQ ID NO 52
<211> LENGTH: 21
<212> TYPE: DNA
<213> ORGANISM: Artificial
<220> FEATURE:

<223> OTHER INFORMATION: SNP probe sequence

<400> SEQUENCE: 52
aagatgtatc caatattaac a                                                    21

<210> SEQ ID NO 53
<211> LENGTH: 20
<212> TYPE: DNA
<213> ORGANISM: Artificial
<220> FEATURE:
<223> OTHER INFORMATION: SNP probe sequence

<400> SEQUENCE: 53
tcagggaggg aagaatttag                                                      20

<210> SEQ ID NO 54
<211> LENGTH: 19
<212> TYPE: DNA
<213> ORGANISM: Artificial
<220> FEATURE:
<223> OTHER INFORMATION: SNP probe sequence

<400> SEQUENCE: 54
ctcgtgtaaa ttcttctta                                                       19

<210> SEQ ID NO 55
<211> LENGTH: 694
<212> TYPE: DNA
<213> ORGANISM: Glycine max
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (510)..(510)
<223> OTHER INFORMATION: n is a or g

<400> SEQUENCE: 55
cacatcactc tgctttcctc tctgaagacg ataaacagta acacacagcc tacctcacta           60
gtgatattgt aggcttgaca ataatgccag ttgcatagga accagataca agttgtatac          120
acggttaaag cccatctcac accatataca gaccgagcaa cgcaaaattg aatgctttag          180
acatggttaa agctcaactt cattcaacat tcagccaact tttctatcat cagcatcaac          240
tttaagggtg caaattctaa gcttgacgaa cccgatcacg ccaagacccn ttttgcttgg          300
ccagcacctg aaaccaaata tagcgggatt acttaaatta tttgttatga ttatccatgt          360
gtactgtggc atagaaaaat gcttactgtt tcacttaaaa ggcttgcaac cagttctttt          420
ttatcagcct ccttctcatt ctcccttca ggctcactgt ctgtactggt gggaggcaga           480
agtgctgtag caccaaacat agcttcctcn tgagcagctt gtatttgctc ctcccttctt          540
gcctacataa caaatgaga acaaaatgag attcagtatt ccaaacattg atcaggcatg           600
tacataaaaa ggagctaaat tgactgcttg agcataagag acaaggaaga tacctcaact          660
gcagaaaatc tgaaactttg gccaatgtgc ttga                                     694

<210> SEQ ID NO 56
<211> LENGTH: 497
<212> TYPE: DNA
<213> ORGANISM: Glycine max
<220> FEATURE:
<221> NAME/KEY: misc_feature
<222> LOCATION: (32)..(32)
<223> OTHER INFORMATION: n is a or c

<400> SEQUENCE: 56

```
ggaaaacttt caacttcccc agtattaaac cntcacaaat gacataaagc acaacacaca    60
gcataaacac atacatggaa caacatacag taaagacaga acagaacaca cttgtttgga   120
atgagagaca gcaacaacca attaaagatc taggcagata tttgaattga cttgacttga   180
ggtttcttgt cttcctcctt gggcacagta acagttagca ctccattctc catagcagcc   240
ttgacctgat ccattttggc attctcggga agcctgaacc tcctcatgaa cttcccagtg   300
cttctttcaa cgcggtgcca cctatcatct ttctgttctt gttctttggt cctctcacca   360
ctaatctgca gcaccctccc atcttcaact tcaaccttca cttcctcctt cttcaacccg   420
ggaagatcaa cgttgaacac gtgagccgcc ggagtctcct tccagtccac gcgagtgttg   480
gctatggcac tgctttc                                                  497
```

<210> SEQ ID NO 57
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 57

```
ttgacctctt tgcttcttca gattgcttac ttgctgcaac ctctgacaga ttcactgttt    60
tatcatcaaa accaagcttg aatttattaa ggaaactgtc tcctgattgg ccagcatccc   120
tattcgtttt tgccacattt gtgttctgaa atgcaagatc aattttggaa gatttattcg   180
tttggtccaa ttcatcaggc ccaccatggt tgtcataaaa tctcggaggg aaggaatggg   240
aacctctatc ntattcttgg aaacgtggag gaggctgatt aactggcttc ctacttctca   300
aaggtctact tggaattggt tctgacaaag actgatcaga ttctccatta tctttaaaac   360
ttgagtctga ctgttgaaga aaaaagtcat cggattctcc aacaggttgt ttgcttctgc   420
cactgcaatc atcggtaaag ctaaaatggc gcacagtctc aagcaatggt ggcagatatt   480
gtttgcaatg tacaaaggaa a                                             501
```

<210> SEQ ID NO 58
<211> LENGTH: 370
<212> TYPE: DNA
<213> ORGANISM: Glycine max
<220> FEATURE:
<221> NAME/KEY: misc_feature
<222> LOCATION: (67)..(67)
<223> OTHER INFORMATION: n is a or g

<400> SEQUENCE: 58

```
ctatggcctt gcagcagggg tgttcacaaa aaacattaac acagctaata ctttgactag    60
agcattnaga gctggaacag tgtgggtgaa ctgctttgat acatttgatg cagcaattcc   120
ctttggaggg tacaaaatga gtggtcaagg aagagaaaaa ggagaataca gtctcaagaa   180
ttacttgcaa gtgaaggctg ttgttacatc cttgaagaac ccagcttggc tttgaacatc   240
attagcttta gatttatttg atgaaaagat taataaatag gctccaataa taagatcat   300
taaattgggt ttattccatt catagtttct gataatgatg aaaataatct agtttctttt   360
tctgttttcc                                                          370
```

<210> SEQ ID NO 59

<211> LENGTH: 763
<212> TYPE: DNA
<213> ORGANISM: Glycine max
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (299)..(299)
<223> OTHER INFORMATION: n is a or c
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t

<400> SEQUENCE: 59

```
aactgttaat tcaacaaaaa taatgtatgt catttttttt ctcctttaag ctataatttg    60
acatctaaac aaggtcggcc ataaaatttc gtgaacttct tctgcaaaaa ctggtcttcg   120
gctttaaaac cctcttcacc taagataggt cgatgaaacc cataatagaa catatgttat   180
cagtgatgag atcacttcaa atgcccttgg tcccttaagt atggtaatag gaggaattac   240
tgacaccatc aagaaggttc ccaacagcca cgaaatacca aatgctccaa ccctgcanca   300
aagcatcatg tcatataagt aaaagcctaa agaaaaaaac cactaatgca acaaattcta   360
aagaaagggc acaatgataa tatgatatta acatcngaat gtaacaccat gggaatgtga   420
tgcttttaaa tgaaaaataa caaatcacga tctaacacta tatattctaa acatatttga   480
aagaataaga cgcattgtat gtacccatat agcgaagctc gtatgttgct cttcagccgt   540
tcatggatna aatatattgt ggcgatcaga gatattgcta cctgaagagt tggcccttct   600
tcagttggaa agaggacagt caaaactcca agtaccaaga atgctattga agttttata   660
atgaattttg tagatggagt ttgaaatctg cctctgacag cctgcacaaa tttggattga   720
ttgacttccc tcattttttt cttaatgtca attttgggt ttt                     763
```

<210> SEQ ID NO 60
<211> LENGTH: 453
<212> TYPE: DNA
<213> ORGANISM: Glycine max
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (313)..(313)
<223> OTHER INFORMATION: n is a or t
<220> FEATURE:
<221> NAME/KEY: misc_feature
<222> LOCATION: (349)..(349)
<223> OTHER INFORMATION: n is a, c, g, or t

<400> SEQUENCE: 60

```
cggaagcaag cataaagaat ctattacaaa tatgatctgc gaaatgnatc aggtgaagca    60
attactttgc acccagaatc cataggaaat tatggtgtat tattatttca tcaatcaact   120
caagactgaa ccctttcact aatctactag ctagacttcc aatgaaaggc acgttagaga   180
aaattatgca catactcagg atgccggaaa attgtaatga tcaagtaaga gatatgtaac   240
atgttagcca catagtggca catataactt ttattctcct cctctaccat aactcggcaa   300
tgaagttagt atngacggta tattagttgg ctgcatcatc atgttcagna acctgatcat   360
```

```
gaactgcaga tgttgatcct ctacccacag ggagatagga ccatgctatt gctgcagtac    420
caactgcaat ggcagtagta atagatcccc cac                                 453

<210> SEQ ID NO 61
<211> LENGTH: 453
<212> TYPE: DNA
<213> ORGANISM: Glycine max
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (349)..(349)
<223> OTHER INFORMATION: n is a or g

<400> SEQUENCE: 61
cggaagcaag cataaagaat ctattacaaa tatgatctgc gaaatgnatc aggtgaagca     60
attactttgc acccagaatc cataggaaat tatggtgtat tattatttca tcaatcaact    120
caagactgaa ccctttcact aatctactag ctagacttcc aatgaaaggc acgttagaga    180
aaattatgca catactcagg atgccggaaa attgtaatga tcaagtaaga gatatgtaac    240
atgttagcca catagtggca catataactt ttattctcct cctctaccat aactcggcaa    300
tgaagttagt atngacggta tattagttgg ctgcatcatc atgttcagna acctgatcat    360
gaactgcaga tgttgatcct ctacccacag ggagatagga ccatgctatt gctgcagtac    420
caactgcaat ggcagtagta atagatcccc cac                                 453

<210> SEQ ID NO 62
<211> LENGTH: 265
<212> TYPE: DNA
<213> ORGANISM: Glycine max
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (141)..(141)
<223> OTHER INFORMATION: n is c or g
<220> FEATURE:
<221> NAME/KEY: misc_feature
<222> LOCATION: (246)..(246)
<223> OTHER INFORMATION: n is a, c, g, or t

<400> SEQUENCE: 62
acgaggttta gcaagcctag agaactattc aattctctcc agaagatagc tacaaaatat     60
gactaggctn taggttactt tcatctgtac gttgtgtttg aatttgactt gtgttacaat    120
tataagatct cgtttagaaa natgactccc atgagacaaa taaataaagc catagtcttg    180
caactactgc gtcatttccg atccatacac gcagggatct gtataaattt tatttgataa    240
aaatanaatg atatgaagtt gtgtt                                          265

<210> SEQ ID NO 63
<211> LENGTH: 501
<212> TYPE: DNA
<213> ORGANISM: Glycine max
<220> FEATURE:
<221> NAME/KEY: misc_feature
<222> LOCATION: (70)..(70)
```

```
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (251)..(251)
<223> OTHER INFORMATION: n is a or c

<400> SEQUENCE: 63
taacaggaaa atacaacgat tctaactcct cgagtcgcat aatcacaaac gatcaaacaa        60
tgaaactcan catacaagtg ctaatgatc aaaacttggc accacaaaac tncacttcaa        120
ttcaccagat ccttctggaa acttgaatac gctcaaatta tataattata tatataaaaa        180
taaaaataaa aagaattgaa catgacccta atgtacaaag gaatccttcg ctgaccctga        240
atggagaggg nttgtttctg ggtgctgcac tcaaacaaga ttgatagtga aggagacata        300
agggtgggca tcagcatcac ctgctaggcc agccatccca actccttcgt cctcggtctt        360
ccagtaagca ctgcagcgaa aatatgaaag gaacaataac aatatgagca catgtggcat        420
taaagagaat tatgaaaaaa gttgagaaga aaaaaaaaa ataataataa aaaaaaaata        480
aaatatatat atatatat a                                                    501

<210> SEQ ID NO 64
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 64
cagtaacagg aacttaatca gaatcctcat acacttctcc atcatcagat aactcatcaa        60
atgatctgat gtcaagctgg taacgaagaa ttccaccaat gccaccaaac cctctgcaga        120
attgggagcc ctcttgagat tgttggtca caaattccag ggagcatcca aattttttgt        180
actcattggc aaaccactcg agcaagggca tcttctcctg aacttccaac tctgcagaag        240
tggccaaatc ncggaagttg cttttgattag cctcttgttc cttgttcaag tgcttaatga        300
caatctcacc agtgatacca ttttttcagca catacctatt aatatccaaa ttttcccata        360
caatgagtgt ttccacagca cccatctcca gtgccttcaa agtgtcctca accccaaaga        420
catatttccc agtgtcctgg ctgatctctt caaaatattt ccctatcaag cgtttctctt        480
gaatgaactt cacatttgat a                                                  501

<210> SEQ ID NO 65
<211> LENGTH: 501
<212> TYPE: DNA
<213> ORGANISM: Glycine max
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (251)..(251)
<223> OTHER INFORMATION: n is a or c

<400> SEQUENCE: 65
accttgattt caatgaagag ggtgggaagc aaaagcaaaa gcagaattcc tttggaaaat        60
tggactccga gggnatcttt gacatggact acttttgctc atcaccacca ccaccaaggg       120
```

```
tgagaactca actagtccct tgccaattc aattggagcc aaaaattggg aaggccccag    180
aagatatttt ggtgaaagac atcatcaaga gtagtcctat ggaagtggct attgctaccc    240
catcagagaa nacaaaggaa tttgagacag tggaagctga tagagtgaag gttttcttca    300
agatcaagga gaaagtgag tttgtggaca tgaaaagggg aatcttggct ccaatggatg    360
ctgctggttc cttgaaattt gaggacaaag gtgaggccat ggagatcatc acctctccca    420
gaaggagggt tattgagaag gatgtgtgtg acaaagaaga ggagtccact tgggaggaag    480
acaacaacag tggtttcaac t                                             501
```

<210> SEQ ID NO 66
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 66

```
ttacaataat tacaaatgaa gttctgaaag cattaaaatg tctaatatcc tccggtgatt    60
taactcgtat atctgctgtg tagctgtcct tgaaacaaaa gaatataaag aaaatgaagc    120
tgaatgcttt tattccaaca ctataagatt tctacactca ttgcagcccc agccacaaac    180
agtaacgctt ctgaaccaaa gaattatat agtggcagtg cccatccatc attatgcaaa    240
gccagcctta ntatttacta tgtagacaac aaagccaaga attgcatgct ctttgaaaat    300
aaaataaaaa taaagtactg actgcagaag tataaaacac actcataagc aagacttgag    360
actcataagg aaatgggtgg ccggatgata attctgcatc acagatcatg aggggaacgg    420
ctgttatctg aatgagggga acggctgtta tctgaatgag cctgagatcc cacattagag    480
ttttgagagg taaataagtt g                                             501
```

<210> SEQ ID NO 67
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 67

```
tgtcactgtt tttctggtcc gtatcaaata ctaacgagca ccaggtaaag caaataaaaa    60
aattgaaagc atcacagcac ttaaccaata aaatttatgt tctatggaaa cttgtccaac    120
ataattcaaa atttgcttcc ctaacaaata tctatttctc aaagcaaaca tataacacag    180
cttaacgctt cttagagaca ccaacagttt taccctgcg accagtagtc ttagtgtgct    240
gaccacgaac ncgaagaccc cagtagtgcc tcaaaccacg gtgatttctg cataatagta    300
agaatacaag atgttagtgt tattacctaa taatatgcac aacttaacaa gggcacaaag    360
agaccctatt aagaagtagc aggaaatcac atggtcattt ctgttaatat tttctaaata    420
atttcctaaa caaacttgtc gtggtcaaag tagtcatgta caagaacaag cactctcaaa    480
taatgtccat gcttattgct t                                             501
```

<210> SEQ ID NO 68
<211> LENGTH: 501
<212> TYPE: DNA

<213> ORGANISM: Glycine max
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g

<400> SEQUENCE: 68

```
gttttcactt ttcaaaatga atggaaacct aaagtgaaaa attattacaa aaaaaaaga      60
aaagaaaaga aaagagagag aacaatttga tgccaaaaaa gtctcctatt attcatccca    120
tcataaccca taacccaatc aattaagtat tttgatcttt ttatctatta tagaagttac    180
anacctcaaa gaccctcttg aagaaatgca gggtaactgc agactgaagg agggtggatc    240
tgaggccttg ntgaggaaag atccagaagg atgcaaggcc agcaagaaaa gcaggagtgt    300
acagcaaaag catgccagct tgctagaca acttgacctg cttttctgca gagggattag     360
cattccaaaa ctttgaatag ttcaaatgct tccctctaat ctctgagaag ccagcattag    420
ccagtgacac aaggcttatc actgacatcc ccgaaaccac cagagaagat ggtggtggga    480
atatgaagct gaacaaggca g                                              501
```

<210> SEQ ID NO 69
<211> LENGTH: 501
<212> TYPE: DNA
<213> ORGANISM: Glycine max
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g

<400> SEQUENCE: 69

```
gttgtttgca acacttacta ttattattaa cttaaccttt tgtttcattg acatttttgc     60
ttccagaaca tttagtggac tctgatttag gtagaaaagc tggggtttct gctcaaagtc    120
aggtgttaaa cttggagaag gagaaaggtc attttcatga caataatgct gcaaagtcaa    180
atgttggtna agccgcaatg gagagtagac agacaccagt caagtctact gatacagaga    240
tccagcaaat naaagggact ctgcctgaag gattttttga caataaggag gctgatttgc    300
gtgctcgtgg cataaagctt gtgaagccag atgtcaagta ggttcccact ttatgttgtt    360
ggttactaca tttaactatc atgaatctgg tttttgcatg gaagtaaaga actgaaatat    420
tctaattact gtagagacga gtactaatta ttctacttta ttctaattat tcttttcaat    480
atcatgggag atttatatat t                                              501
```

<210> SEQ ID NO 70
<211> LENGTH: 599
<212> TYPE: DNA
<213> ORGANISM: Glycine max
<220> FEATURE:
<221> NAME/KEY: misc_feature
<222> LOCATION: (446)..(446)
<223> OTHER INFORMATION: n is a or g
<220> FEATURE:
<221> NAME/KEY: misc_feature
<222> LOCATION: (581)..(581)
<223> OTHER INFORMATION: n is a, c, g, or t

<400> SEQUENCE: 70

```
tgccacggta gtagtacatt ttccataaca aaatactcct tatctactga aacattcaac    60
atggaagtaa gtaactgtaa ttcaaaaccc aaataaaaaa gaagcaataa agaacaaaag   120
cacaaactca accagaggag acagagactt cacgcaactc cttactccta agatactccc   180
gcaaaatgga aagcctggcc gtctcgaaag caaaatagcc caacgccgaa aaacaagcac   240
tatgcaggac ccggggcccc attccacggg taagccctac ccaccctttcc tccttcaaaa  300 tctgcttcac cgtggccgaa accccgtcgt acataaccgc agcaaccttg ctcaccccct   360
cgccccgaac ctgcgtcatc aacctcgtct tcaccacatc caacggcgtc gtgagcgacg   420
ccgatatcgc cccggcgagg gccccncaca gaacactctg caccggttcc atgtaactct   480
gcttagtctt ctgaagcacc gcggctttca atactcgaa agaagagtaa ctcagaactc    540
ccgcgggtaa gtttctcagc aatgtcgcgg agtaaccagc ntagaggccc atcacgccg    599
```

<210> SEQ ID NO 71
<211> LENGTH: 90
<212> TYPE: DNA
<213> ORGANISM: Glycine max
<220> FEATURE:
<221> NAME/KEY: misc_feature
<222> LOCATION: (30)..(30)
<223> OTHER INFORMATION: n is a or g

<400> SEQUENCE: 71

```
tatccattat gcagcacaca gacgcttcgn tgtaactaaa agagtgatta tattgttcaa    60
tatctacgcg gaactttaga tataattgtc                                    90
```

<210> SEQ ID NO 72
<211> LENGTH: 948
<212> TYPE: DNA
<213> ORGANISM: Glycine max
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (782)..(782)
<223> OTHER INFORMATION: n is a or g

<400> SEQUENCE: 72

```
aatcgtacgc acacgctttc gtgcatgttg acgggcgaac gtgggtccgt taccgttagg    60
atggttcccg cgcctagggg ttccgggatt gtggcggcta gggttcccaa gaaggtgctg   120
cagtttgctg gtattgatga tgttttcacc tcctccaggg gatccaccaa gacccttggc   180
aacttcgtta aggtttgttt ttggtattct tacaagtttg ctgcttttga cattttcaac   240
tatcatgaaa atttttatgg acgaattaag gttgtaattc caatgtcaca attaatttaa   300 gcttttttatg taaattatta attttaaatt tagggacgaa ctgttgatgc tttaacagtt   360
gcaattgtgg agtccaatct ttaatttacc ctttgtcttt catttttttt gtggcctttt    420
gtgtatgaat gtatttgaac aanctaccaa ttttgtctcc aaagtgctac tgtttcttga   480
ttcttctaag ttgtttataa ggtaatagaa ctatttaagt aattttcaaa atattcagta   540
ttgaatattc atcacttagt acctatgtta ttttacttaa tatgtgttag tctatggtgt   600
ttttgctgca attgatggca ttcaacatgt atcatcactt gtgtgatttg ttacttgtgt   660
atgtgtgttt atgtggatga tcttttgtta gagaggctaa tgtgtatttg tgtgcatgat   720
cctttggtgg agaggctaat gttcatgaaa gaattgctat gatgttgttt ttagtaccca   780
```

```
tnataatgat gatgctttgt attatttaca ggctactttt gattgcttga tgaaaaccta    840
tggattcctg acaccagaat tctggaagga gactcgcttc tccaaatctc cattccaaga    900
gtacacaggt aaactggcat ggagtgaccc cccagtattc ctcccaaa                 948
```

```
<210> SEQ ID NO 73
<211> LENGTH: 1194
<212> TYPE: DNA
<213> ORGANISM: Glycine max
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a or c

<400> SEQUENCE: 73
atggacgggt atgcatattt atactgatta ctatttgttc ttttcctgct ttatttgttt     60
gaaatattta tacttaatgt acttaggaaa ttgtagattc atgtatcaca tgataaatgc    120
aattagtgtc caccagttaa ttgtagtgtc taggaagttg cactcagtta atattagcct    180
gggacatagc ctccaccaag tcttatctac actattattt gtcaagaagc atcatatata    240
acttaggatt gaggctatta ttgactatta tgttaacata agctcaaata taaattgtcc    300
ttttgtacta cacagttttg tcttcttaat taatcttggt tgttaagaat ttagattaga    360
tgcctnaatt aatttacaat gaaaaaagga tggagtagaa ggaaaaagtg ggtttgcaaa    420
ataagatact gatcttagag cattctatat ggttcttctc ctgaagttcc aaccataaaa    480
gatgaaccaa gctggcaaga tgtgaaagtt tgaatacatg gaattttata cttttaatcc    540
atatgtattc ataaaagttt gctacatatt atattaatgt ttttcgttgt tggtttgcac    600
acttgttaat aatcctcaat gctaaggaga agaaanggtg ctagttcatg tgaggaaaat    660
tgggatatgc ttgcatggac ttggggaaac catctaaata gaggctacac attttgcaga    720
tttgaagcaa ccagccgaat tcggatgatg gagagcaagg caaatgagga gatgaataat    780
gggaatgagt ggcatgtgcc tatactggcc atgcagctg atgtgatcca tgctacatac    840
gacaagtgca tgaaatgtgg catggatgga tatgtctcaa agccatttga ggaagagaat    900
ctgtatcagg aagttgcaaa gtttttcaaa tcaaaaacca tgtcagattc atgacaaatg    960
tgcttcctta cttggcaacc aactagatga ttggatttgg agacaacaca ttttagtttg   1020
atcactgcta gcactttcat gtcacatgta acttgttact tttgctttct tgcatngagt   1080
aacacttgtt tttgcaacat atttgagttg agttcgttga gggatcatta ctagtactaa   1140
tcggctgcag tttgtcatta ttagagtaaa attataccac gccacacccc ccaa         1194
```

```
<210> SEQ ID NO 74
<211> LENGTH: 1194
<212> TYPE: DNA
<213> ORGANISM: Glycine max
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (636)..(636)
<223> OTHER INFORMATION: n is a or g
```

<220> FEATURE:
<221> NAME/KEY: misc_feature
<222> LOCATION: (1076)..(1076)
<223> OTHER INFORMATION: n is a, c, g, or t

<400> SEQUENCE: 74

```
atggacgggt atgcatattt atactgatta ctatttgttc ttttcctgct ttatttgttt      60
gaaatattta tacttaatgt acttaggaaa ttgtagattc atgtatcaca tgataaatgc     120
aattagtgtc caccagttaa ttgtagtgtc taggaagttg cactcagtta atattagcct     180
gggacatagc ctccaccaag tcttatctac actattattt gtcaagaagc atcatatata     240
acttaggatt gaggctatta ttgactatta tgttaacata agctcaaata taaattgtcc     300
ttttgtacta cacagttttg tcttcttaat taatcttggt tgttaagaat ttagattaga     360
tgcctnaatt aatttacaat gaaaaaagga tggagtagaa ggaaaaagtg ggtttgcaaa     420
ataagatact gatcttagag cattctatat ggttcttctc ctgaagttcc aaccataaaa     480
gatgaaccaa gctggcaaga tgtgaaagtt tgaatacatg gaattttata cttttaatcc     540
atatgtattc ataaaagttt gctacatatt atattaatgt ttttcgttgt tggtttgcac     600
acttgttaat aatcctcaat gctaaggaga agaaanggtg ctagttcatg tgaggaaaat     660
tgggatatgc ttgcatggac ttggggaaac catctaaata gaggctacac attttgcaga     720
tttgaagcaa ccagccgaat tcggatgatg gagagcaagg caaatgagga gatgaataat     780
gggaatgagt ggcatgtgcc tatactggcc atgacagctg atgtgatcca tgctacatac     840
gacaagtgca tgaaatgtgg catggatgga tatgtctcaa agccatttga ggaagagaat     900
ctgtatcagg aagttgcaaa gttttttcaaa tcaaaaacca tgtcagattc atgacaaatg     960
tgcttcctta cttggcaacc aactagatga ttggatttgg agacaacaca ttttagtttg    1020
atcactgcta gcactttcat gtcacatgta acttgttact tttgctttct tgcatngagt    1080
aacacttgtt tttgcaacat atttgagttg agttcgttga gggatcatta ctagtactaa    1140
tcggctgcag tttgtcatta ttagagtaaa attataccac gccacacccc ccaa          1194
```

<210> SEQ ID NO 75
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t

<400> SEQUENCE: 75

```
cgatccaaat tattcacact ttgggggatt tacctttggt tgaatgttgt tgataaaaga      60
cataccctaat tacgttcatt gacaaacgcc aagatctaaa gagcttcgca ggaagcctat     120
tgtttaatga gaaagagtt gatttaccat gggagaatga agtaaaaagc agagaattaa     180
gtagttctat catgtcatct caagagcatc aagtgttttt gatgaatcct ttttctgttt     240
```

```
gcagtatcat ncaactagtg gggttagcaa gtgcacactt tgcctgagta atcgtcagca    300
cccaactgct acttcctgtg gtcatgtatt ctgctggnan tgtctttgtg cattcttact    360
gctttccatg tacccgcttc ttgctgtgtc tcatcttgtg tttgatgtaa tccatgcngg    420
aactgtatca cggaatggtg caacgaaaag ccagagtgcc ctctttgtcg cacgcccata    480
acacactcga gtctagtttg t                                              501
```

```
<210> SEQ ID NO 76
<211> LENGTH: 501
<212> TYPE: DNA
<213> ORGANISM: Glycine max
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (398)..(398)
<223> OTHER INFORMATION: n is a, c, g, or t

<400> SEQUENCE: 76
```

```
aaaatcgcaa acgccagcta gagagtgtgt gtgtacacac atcacatcct gctgaataat    60
gagaccccaa gaagaagaag aaaaaaaata taaagttaac acacttaaat acttaatnnc    120
catatcaact gcggaaggat ggtcttggtt acgataatga agggcaagtt ctaagcaata    180
gagaaccggg ccggcggntg aaggaatccg aaccgggtcg aagtattggt tggggcccac    240
ggggacggtg ntccagccgt tgcaagggtc gtcactgttg acaaaaacga aaccttccac    300
gtaatcaaaa ccatcacccct ctcggagagt caccagccac tctgcgtctc gagtgaagtc    360
gccaaattct gtgtacacca cccttatcca tctcaccnaa taacaaaaaa atattttttt    420
ttattagata ggtaatatttt tagtttaatt attttattta acctaccatg tccggggctt    480
gttgaaccgg gactcgagcg c                                              501
```

```
<210> SEQ ID NO 77
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or c
<220> FEATURE:
<221> NAME/KEY: misc_feature
<222> LOCATION: (389)..(389)
<223> OTHER INFORMATION: n is a, c, g, or t

<400> SEQUENCE: 77
```

```
cagattttat tctttaatta gtacatattt gatttgtaca gattttgttc cattgtattt    60
ctttccttaa ttaggttgtt ggcagcttat aaataagtct tgtattcact ctttgaaaac    120
agagaattac aataatattc agattattat ctttcaagtt ggtatcagag ctcccaatcc    180
agggggctct gcttctccat ttttccaggc agccttcatt gctgcagttg atactgtttc    240
tgtgcccaat nactgcatat accactggtc gttgtccgcc gctgtccact gctgtcctcc    300
gtcgtcaacc accttccgcc gcaaaactga tcggagaacc caccaggaga agcgctttct    360
```

```
ccagatcggc ccatccctga agtttcacng ccaaccgcca tcggacgcgc tgccactcgc      420
tgtttttgtc tccggcgtgt gtaagccacg cgccaccgta caggccgtct tttttgacgg      480
caccgccaca gaacaggtca c                                                501
```

<210> SEQ ID NO 78
<211> LENGTH: 501
<212> TYPE: DNA
<213> ORGANISM: Glycine max
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g

<400> SEQUENCE: 78

```
aactcttctc tcgagtatcc gaagttcttc atttctaatt atgaaattta gtatttaagc      60
tcatcaaatc caaccactag tttatatact aattgatatt agtgttaata tattcacta       120 ataagaaata attggtagct tcttaggtag cataacaatt gaaacttgaa agtaacagtc      180
taacaacaga tcgttaagga gaccaaacca acagaacaga gtaacagaga gttagcantg      240
caacaaagag naagaaaagt tgaaacattt tcagacagtg gcatgtggga atctattctg      300
ttaacggtgg ctgccaccgc tggcaacaac atcggaaaga tccttcagaa gaagggcact      360
atcattcttc cacctctctc tttcaaactc aaggcatgtc taaagttcta ttttaaaat       420 ttgattttgt tttcactaaa gatctcacct tttttggtaa tattttcatt tgaaacatgt      480
gggtgtctat gaattttgta g                                                501
```

<210> SEQ ID NO 79
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (302)..(302)
<223> OTHER INFORMATION: n is a, c, g, or t

<400> SEQUENCE: 79

```
ctaaaatccc agctgacaag gcgtccaaga tgccttcagt gatgagtgct actggactgt      60
aagggttaaa aattgaagca acactagctc caatagcaac accaagtggc gttgttagtg      120
caaaaaaaca tgacattatt gttgctgata aggtcttgaa ttgggcttgg gagatgcaac      180
caccaagtgc aaatccttca aagaattgat ggaaggataa tgccacaatt aggggtttca      240
tggtacaggg nctttgtgaa actcctagag ataacccaat tatcatcgaa tgtgatacaa      300
tnccaagttc caataaccta acacgagttg gatatcagaa atttgcataa tttgttgcgt      360
atattgtttg taatcaacaa cactttaaca atctttacgc acccttaaaa atatattctt      420
tattattggt ttaaatttat taaaaattaa aaaaaattgc aagcaagtat ggttaaataa      480
gaagttaaat tgacaaaatt c                                                501
```

<210> SEQ ID NO 80
<211> LENGTH: 1270
<212> TYPE: DNA

<213> ORGANISM: Glycine max
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (351)..(351)
<223> OTHER INFORMATION: n is a or g
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (946)..(946)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t

<400> SEQUENCE: 80

```
tactggcgga ggcacatatc ttgtgtatgt tgatgatttt gcatttggtc cagtggcaag      60
atacttgcaa ctcgatcata gacaggtact gtttctcaga ttcactatct aaatctcttg     120
ttgccttctt tcttacagat tgttctcatt catgctagca taccantcac aaatgcatgc     180
atgctttgca atttgcaaaa cagttttata ccaaattcaa ctaactttag tttttggttg     240
gtgacgggat tttaagggac tacagaactt ttatggccaa aatgtagtca agtgtgaaac     300
tataaggtga acattgatg tattgggaaa acaccataac taactgtgat nttgacgatt      360
atgtccttgt tggaaatagg ttgcatttgc acctacaggg ctctcaagtc aaaacctaca     420
agtcatgtcc cccatttgta tcttagaggt ttcaccttga gatatataaa tcttttagtt     480
taaataagaa attccttacc ttttactttt ccatatatca aattgaatct gttttttatt     540
ttacccttt tcccctcata gggactcact tatatttgaa attgcctttt cttaatagat       600
agatctctta agatgctaat tcaaatcagc acactaagtc tgctaaattc gaacagttgt     660
gtttgttacc acccaacaat tcagattat tgacacccca tttgggccct aatttaatac       720
ggtgatatga ccttgatttt ggaaaagtaa ttcagttata gatgtgttga catttttatc     780
catagaataa tccatttgcc aagctctccc tttctctcca ccccttaaan ttttgtttgg     840
tgtcaatttt aattctttaa aagtataaac tcttatttga catgctgtgt aacctgagat     900
gttgcagtgt tgcttccctc ctaacctatc tgcgcataca tgcaancatg gttacctgca     960
tgctgagtat ggtactgcaa tcacatggga ccatgcatta cagacaagtt tgctgtattt    1020
tgagaacaaa actcacaacc ttttcacttg caactgccac tcgtttgtcg ccaactgtct    1080
gaatcgactg tgttatggtg gatcaatgag ttggaaatg gtgaatgtag gagctttggt      1140
actattcaag gggcactggg ttgatttcag gtcaattgta aggtctttct tgcctttttat   1200
tgtggttgtt tgcttaggtg ttttttatggt tggatggccc ttcattactt gggctacgtt    1260
cctccaaaga                                                             1270
```

<210> SEQ ID NO 81
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is c or g
<220> FEATURE:
<221> NAME/KEY: misc_feature

```
<222> LOCATION: (260)..(260)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t

<400> SEQUENCE: 81
tttttttttt gttagcagga gggatgacct ttccctcctt ccattcttct taaccatcca      60
accaacctta tatctccact tttattcctc aaataatcac ttattcctac gagcttttaa     120
aaattaagtg cttaattttg aatattagtt aagtacacgc atagttaggg ttttgttgct     180
catttgctgt gtttttttt tttttgcag atgtgaaggg tccatactcg gtgccgtcga       240
tttcgccgtc ngcggtgtcn tactcgtacc agggtggtgg tgcgagcaag aagattgaca     300
ttcccaatgg gagggttggt gttatcattg gaaaggtggt gagaccatc aagtaccttc      360 agctgcagtc tggtgccaaa attcaagtca ctcgtgatat ggacgcngat ccgaattcgg     420
ctactaggac tgttgagctt atgggttctc ctgatgctat tgccacngct gagaagctca     480
tcaacgaagt tctcgctgag g                                               501

<210> SEQ ID NO 82
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or t

<400> SEQUENCE: 82
gttatattga gatcaatcag tccacggctt agtgaatcag cccagacgcc agacttcacc      60
tgaaaagcat ccttttagg ggaaacttta gagtctgcta aagatttacc agtcacatta     120
tcatgcttgc catcactgac aacattattg gagggctgtg aagacacaga atcagattga     180
gaagtaaaat caccaaaaat atcagatcca tcaaaattat taagaggaac agcagcaaag     240
ggatcgatag ngctgttatt cataggaaca gacttctccg acttgttgtt tggctgcact     300
gccagttcag gaatggaaaa caagtcaact gtaggtgtaa ctgcaggaat ggctggttgt     360
gaagaaaata gatcaacctc agcctataca cacaatcaac aagacacatg gaattttagc     420
agtgacaaaa atgtggagaa agaaggtaag aatataaatc cattgttcta tcccgtgagt     480
aattcacaat cacctttat a                                                501

<210> SEQ ID NO 83
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 83
cttcttcttc ttcttcacaa aaggatgatt cttctgagtc ccaacaacaa cattccctca      60
ggcacttcat tgatgactct cccaaaccac agtctcatca taatcataac catcgttcgt     120
cgtcatctat ttggcctgaa ctcgacaaca tgcagtcaga caggactcag ttatcaatct     180
```

| ccataccaat atcttcctca gatcacttca tgtcatttgc aacttcctcg ccctcgaatg | 240 |
| aaaaactcac nttgtcgcca ctaaggcttt cgagggagtt cgaccccatt caaatgggat | 300 |
| taggagtggg aagtgcctcc aatgaagcaa acactaggca agccaattgg attccaatca | 360 |
| cttgggagag ttcaatgggt ggtcctcttg gagaggtttt gaaccttagt aacaataata | 420 |
| ataacagcaa tgcaagtgat caatgtggca agaacaacaa caacacttca gctctcaacc | 480 |
| tcatgaaaga tgatgacgat g | 501 |

<210> SEQ ID NO 84
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (305)..(305)
<223> OTHER INFORMATION: n is a, c, g, or t

<400> SEQUENCE: 84

| ctatcaactt ggaggagtca tgagtgaaaa tcatagaatg ggcaaatggt aatatctgag | 60 |
| gaagctccct ttttctaaca tcccacttga ttttttccaac ttcatcccctt ttcaattgaa | 120 |
| aaagactagg cttttatga tcagagtatg caaatagcgc ccctgaatta gaatggtgc | 180 |
| tgcaaattat cttctgagat gccttactgt taacttgagc cactacaacg ttctttgtaa | 240 |
| agcctccaga ngtgcggaca tttttttagtt gtagcaattg aacctctatc ttttgcgaag | 300 |
| attgnactaa aagcagtttg cgttgattaa agacagaatt atgcactagt tgaatgggtg | 360 |
| ttctctgagg cgcaggacag atatcatgag gagaaaacat ggtgaattct ttcactgggt | 420 |
| atgcaaaaag ttttgtgtca tctcctgctg agataagcat aggaaccccc aaatgagccc | 480 |
| acttatggta acggaaacta a | 501 |

<210> SEQ ID NO 85
<211> LENGTH: 501
<212> TYPE: DNA
<213> ORGANISM: Glycine max
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g

<400> SEQUENCE: 85

| agaagaaatg tatcagaaag tgtgttgctc cactctcatg agaaaaaaaa tctgaaaatt | 60 |
| gttaaagaac atcaataaat acttggtttt gcaaatatgc atttgaaata ttaatttaac | 120 |
| atctgacaat taaaagcaca tgattacaaa aaattaacta cttacaaaat tacttaagca | 180 |
| ttggaacttg gcttttatca agcacagacc aacctttgta ttttgtaaac ttgccnatcc | 240 |
| ttgtggagaa nctgatttgt gctccaatga caatgctggg agtacccatc atcccagaaa | 300 |
| aatcaatagc tggggagcgg tttaaaccaa ggggtgtgta tctcaacaca accaatgcaa | 360 |
| ataacagtca ttcaataact cttccagagt caacaatgtc ttaaaacacc tttacgaaaa | 420 |
| agaagtccaa gataacagac ttggaccgaa tattccaacc ttttatccca agacaatctc | 480 |
| agtaccttgc cagaattgta a | 501 |

<210> SEQ ID NO 86
<211> LENGTH: 101
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a or c
<220> FEATURE:
<221> NAME/KEY: misc_feature
<222> LOCATION: (96)..(96)
<223> OTHER INFORMATION: n is a, c, g, or t

<400> SEQUENCE: 86
acaacaatta tacatgtata tacaagaatt aaaacatgga atttgaatct tctggtcctt    60
naggctcagg aaaagcaagt caatagggat cgattntcca t                      101

<210> SEQ ID NO 87
<211> LENGTH: 530
<212> TYPE: DNA
<213> ORGANISM: Glycine max
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (281)..(281)
<223> OTHER INFORMATION: n is a, c, g, or t

<400> SEQUENCE: 87
aagacaaaat ccttcagaaa cttcgcgaga aagaagctat ggtagaaagc atcaacaaga    60
ggaacattga actcgaagat caaatggagc agttgactgt ggaagctggt tcgtggcaac   120
agcgagcaag atataatgaa aatatgattg ctgctctcaa gttcaacctt cagcaagcnt   180
atgtccaaag cagagatagt aaagaaggat gtggtgacag tgaggtcgac gatacagctt   240
cttgctgcaa nggccgttcc ctcgattttc atctgctttc nagggagaac accgacatga   300
aagagatgat gacatgcaag gcttgcagag tcaatgaagt gaccatggtt ttgttacctt   360
gtaagcatct ttgcctctgt aaagattgtg aaagtaagct tagtttctgt cctctatgtc   420
aatcctccaa atttatcggc atggaggtct acatgtaact gcaaagtata cttctacttg   480
tgaaatctct aatttcatgt ttttattatg tgtcctttca tgtagcttgt                530

<210> SEQ ID NO 88
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or a
<220> FEATURE:
<221> NAME/KEY: misc_feature
<222> LOCATION: (382)..(382)
<223> OTHER INFORMATION: n is a, c, g, or t

<400> SEQUENCE: 88
aataatttct aaaatatttt gtgatgcgat ctcatttgat ttggtttaat tcaatcaatc    60
cgtgaaattt ggaaaataaa aaaatcaaa ccaaaataat taataaccat aaattttttca   120

```
ggggttttca atattttgaa tgagttttgg ttcttaagct ggatttagtt cagttctaaa        180
tacctaatca atattcatcc aatagaacgc gccnctactg agagacccga aacacactca        240
ttgcgcggaa ncagttatcg ctgcaagaac aacaatggaa gacggcgata cgacggagga       300
ggcggttgtc gttccggtct caaacggcga cgagcaatcg ttttctcatt cttcctcacg       360
gcaacgcgat tcggaggagg antctccgca cgaaacgttg cgtaacacaa aagcttcaat       420
agagaacatc gtagccgaga ttctctctct gaagaaccag gcaaaaccca aaccactcct       480
cactctccga ctccgagagc t                                                 501

<210> SEQ ID NO 89
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or a

<400> SEQUENCE: 89
aagtataata tattatagtc atgataatat aaattttta atcattatct aataaaataa          60
taattatggt aagcttataa taattacttt aaaaacgaat ttcacgggat tttatcacta       120
ctttaaaact gaaaacataa ataaaatgcg aagacgtgga gaagcgacaa ctcagagtta       180
taactcttat aaaacagctt gctacagctt tgaagcgttt tattttacta gttcgttcc        240 cactcacacc nacaacacaa gctacaccac cggcactact agcatcatcc tccacaattt       300
gacgcgtcct tttgcttgct ccgcacgtca catcgcgttt tctcagattc actctcgccg       360
tcgcagatct cgccgcagat ctgaacaaca atggacggtt acgacggcac cgtcaggctc       420
ggtgccatca acctcaagca cgatcgcgcc gccgatttcg actccgccac cgccgccccc       480
gacgtctccg tctcctctcc g                                                  501

<210> SEQ ID NO 90
<211> LENGTH: 501
<212> TYPE: DNA
<213> ORGANISM: Glycine max
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (251)..(251)
<223> OTHER INFORMATION: n is a or c
<220> FEATURE:
<221> NAME/KEY: misc_feature
<222> LOCATION: (313)..(313)
<223> OTHER INFORMATION: n is a, c, g, or t

<400> SEQUENCE: 90
cggaacttgc tgtagttgta ctcgttgtag gtgccattct cggcccgcgg atttcggatc        60
cgggttatga gtcggatctt ccagccggag agttcgaggg ncggcgtttt cgcgacggag      120
atggaggtgt ccaggaggag gattaggtca cgcttggttc cggtttggag cagggtttgt      180
gctagcgtta ttgcgccgca cacgtagcct tctgaggagt ggagcactgt tgcataggcc      240
tcacgttttg ntcgcgcttc gcttttaacg ctttgttcca ggttccacgt gtcgtacacc      300
ttgtcgattc ctnaaacatt aaacaaaatt taaattaaca tattaattag ctactttta      360 aacattttt gtaggtttag ttacatattg atccaccaaa taatttatta ttataatatt        420
attgttatat ttaagcagat tttctcctcc tatcacattt ttttatcctt ttgaatcaat      480
```
ttaatgttac tcaaatatca t                                              501

<210> SEQ ID NO 91
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 91
agacttggtt tccatccaag tgccaaggat ttttccctca agaccggtct aagactgagg    60
tgaggtgaat tagatttgtt tgttttaaat tcttagatga tgatgtaatg ggacgtttaa   120
ccacaaaagg ctgagttggt ttcacgtttg ggaagccaag tggtttggaa gatgaattgt   180
agattgttag tcaaatattt gcttccttta aagatgcgct gggaagtgtt gtttcctgtt   240
agtcttctcc naaatgtgaa actatcatgc actaactgat gaggaaatta tttagttgtg   300
atgtagctga aatcataatt cattgtatct gtgggattta ttatgttatt gatgttgatt   360
tttatcatca aaatcgtttg tctattcttc cttttaatac atcataatca tacctcgaca   420
aaattgaata tatcacttac agataggtaa tacatagtcc aattaatttt gtcgaacaga   480
ttttgaaaat gcaattatcc t                                             501

<210> SEQ ID NO 92
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or a
<220> FEATURE:
<221> NAME/KEY: misc_feature
<222> LOCATION: (417)..(417)
<223> OTHER INFORMATION: n is a, c, g, or t

<400> SEQUENCE: 92
agcacagaca catatatggc aatacagttg tctaagaaac tcaccatcga ctgaaatttg    60
aatagcttgg tttgaaagtc tttcctataa atggtgatga aagaaataa aagaacccaa   120 acaagcaggc atacatagac caccatttaa cattttttgtc taattttttct acaagggtat  180 gtatattgtc agatgagatg aaaaagaggc aacccacaac aacagcaatt acagcatggc   240
gggaatgttc ntgagggtaa ggataagtgt gggttagaat agttctaacc ctctccattt   300
tcagcgtatc aagaatacca gcagactgct tactagagcc cattccaatt aaaaaaaatc   360
taatataatg tatcaaattt ctggcaatga agttcacttt aggagctcca gaaaacnata   420
gagagcagca ctagcagaat cctgcagaag attataaaaa caataatatc agtattattt   480
gcaataagat aacctcatca t                                             501

<210> SEQ ID NO 93
<211> LENGTH: 501
<212> TYPE: DNA
<213> ORGANISM: Glycine max
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (49)..(49)

<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (251)..(251)
<223> OTHER INFORMATION: n is a or t

<400> SEQUENCE: 93

```
aacatctttg gcngcttcgg aatctgaaat agagggaggg cttatgttna aggagaggtc      60
nggctccgcc gaaggtgatg atagtaaggt ttgcattacc gtttgtgaat tagtgaacat     120
ggagaataga agatctagct aataggtttg tttttcaggg ggtgaaatat acaaaaggta     180
atgaaattat taatagctag aaggggtgag agtacttgag agtttaattg gggatgtgat     240
gtggaaaaac ncgagttcag aaaagcaaag aattgatgaa gggggaatg gaaaggaatg      300
aattgaaaga ggtgaaaagg aagggtttta ttaagggctt tgattatatc atgagtgact     360
tatgatttgt gttggtaagg caatagtagg cttttagta ggatccccac tagggttgaa      420
agaacactgc catagggaaa aaaattaaag ttgagagact gagagatcga gtaattaatt     480
ttccagggac tacttgtcac t                                               501
```

<210> SEQ ID NO 94
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 94

```
tttcgtgttt gagcctttca gcagacaaaa cgtatttata ctccgcatcg tgggacagga      60
caatcaaggt gtggaggatt tcagactcca aatgcttgga atcaatccac gcccacgacg     120
acgcggtgaa cgccgtcgtg tgcggggacg ggggcgtgat gttttccggc tcggcggacg     180
gcaccgtcaa ggtgtggcgg cgggagccgc gagggaaagg cctgaagcac gccccggtga     240
agactctgct naagcaggag tgcgcggtga cggcgctggc gatggacgcg gcgggggggt     300
cgatggtgta ctgcggcgcc tccgacggac tggtgaactt tgggaaagc gacaagaatt      360
acgcgcacgg tggggttttg aagggccaca agctcgcggt gctgtgcctc accgcagcgg     420
ggacgttagt gttcagcggt tccgcggata agaccatatg cgtgtggaaa cgcgagggtt     480
tgattcacac gtgcatgtcg g                                               501
```

<210> SEQ ID NO 95
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is c or g
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t

<400> SEQUENCE: 95

```
attggagtgg gaaggggaaa ccatgggtga gattggacgc taacaggcct tgtcctttgg      60
atgcgctttg ggcaccttat gatctattac gtacccctt ttctttcgac tcttgaaatt     120
tgaatttggg atattcctgt aacatagcta catacaaatc aggcttaatt tctcgatcta    180
tatgctgctt gggaagattg aattgaagag acaacaacat aacatgggtc aattatacac    240
cgtacgaaga nctagctact catcggacca aggatacatg ttcaaagtgt acattaagat    300
gtgaaggagg tgagtggggt tcgtgantgg gattgtacga ttgagtttgt atatagcgaa    360
gatcgagcta cgtaataagt tttggatgcg cntattcaga tttcttttt tggtcctgat     420 aatgtgaaca tagtgagggt ttttgtatag gcaaactcat tttccgtgtt cagatccttt    480 tcttttttacc ttgtatttt c                                              501

<210> SEQ ID NO 96
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or c

<400> SEQUENCE: 96
acccactggc cagactcacc aatggaagta tcggactcat cgcattctgg aatagtgaga     60
ggggtgtaaa ggtgacggtg cgtggggcta gcaggggcag acgctgcaaa gaaagggtaa    120
ttgaaggagg ccatggattc tttggcaata gactcccatg taggaattgg ttttgaattt    180
cttgatgttg gtgatgaaag aggtggtgtc acaggggcac tgtttgatat cctgagagga    240
ggaagagaca nggacgcatt gcgaatgtat ggaatgaggt ttgatacatt gtccttatcc    300
ccatctaaac gaaacgggct tggcaaagag gaggaggaag ggctaacttg gtatgaagga    360
attgggctgg gaaatgatga agaaagagga cttggatttt gagaagaaga aaagggaatg    420
tttctcatgg agctcccagc accattggct agaggcggct tgcaacccta ttcatccaaa    480
acacataacc acgttaccac t                                              501

<210> SEQ ID NO 97
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or c

<400> SEQUENCE: 97
ctcagagctc caccgagaag gtatggctct ccttcaaggt atcccggtgg cggggctgca     60
acttcctata ggcttggtgt tggtggtgct tctgctgatc acaatgctag gccagcttca    120
gttgatccag attttcgtgc agcctccgag ctcaaattta gggcctccac catgaccct     180 ccaggttttc ctaaaagaag agatggtatg tttgtaggga atcaagttgt aaatgaccgc    240
agttgagtgg nagagttaat tgcatgatat aggttttct ctaactagtt tcagatttcc     300
ttagctttta atcgtatgca tcatttgcta tctggtctcg cagttttta actttcaagt    360 tgttgcacaa aagagagaaa taaattataa tgagaaactt ccaagtcttt tcttctccca    420
tatatttttt atgtccttcg agttttgatt ttattaacaa gtcccatata tgagaaatat    480
attgtcccaa ggactggttg a                                              501
```

<210> SEQ ID NO 98
<211> LENGTH: 813
<212> TYPE: DNA
<213> ORGANISM: Glycine max
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (561)..(561)
<223> OTHER INFORMATION: n is a or t

<400> SEQUENCE: 98

```
ctcacagcat gacaaacgat tgacaactcg gcaaggtacc ttttgctgaa cgcacgcttt      60
aatttatttt aatttcgttg cttatactta ccgtattcaa ttttacaata tataaattaa     120
catgatgact cgcatgtaat aagtttatag tctggtaatt aaagcaaaag gcaatcgata     180
caatttactt catatttagg tatttgttca tagtatattt ttattttatg gttttagtaa     240
acaaatggtt tatttgctcg tatgtatatt gtcatgttgt ttaatatttt tgtgattaga     300
attgaattga aagtcttaca attaattgac tatacaatca atttccttca gaagagatca     360
ntgtagatta ctactagctg tataatatat ataaactatg acgtgtttat tttcatgatt     420
aggattgaat tcaaagtttc gtacaattaa atgactcgtt caatgttggt aatcggtata     480
caatctactt caaaagacat ttgcctggca gtacagtgct ttatgttcac tataatttga     540
ttaattaaaa attaactatt natcgtcgtc attgagaata gcataatttt ttaatattgg     600
ctttgagttt ttaacttgtt caataactga attaaagtgg ttttggatca tctaaaaatt     660
tctaacctat ggataattta cgatgaaaaa tgtgtaagtg cttagtttgc ctacttcaac     720
cagatgcatc taatcccatg ttccaatatc ttaagttgta agtttattat ttatgttcag     780
cgtatattta ctatatatca gcttatatcc tta                                  813
```

<210> SEQ ID NO 99
<211> LENGTH: 553
<212> TYPE: DNA
<213> ORGANISM: Glycine max
<220> FEATURE:
<221> NAME/KEY: misc_feature
<222> LOCATION: (33)..(33)
<223> OTHER INFORMATION: n is a or g
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t

<400> SEQUENCE: 99

```
ggccatctac gacagggaaa ccccagatct gtngaagaac ttggtcaggg ccgtgggagg      60
gaagacggtn gaggaagtta aaaggcacta tgagatgctc gttgatgatt tgaagcaaat     120
tgaagaaggt cacgtgccct tgcctaatta cagaaatgtt gctgcaacag gaggaagcag     180
catcagaggc tacagttaca tggaggaaga acaaaggttg aaatcaaatc cttattgaac     240
ctcttgcttg catatatatt gcttaagcag tcttggagaa ttacaaaatc tcacatcaaa     300
caaataaaga taagaaaaga aatatgtttc acacctcatt aggggctata tacatagaa     360
cttattttan ctatgtaatt gttcttcctt tttctaacat ggcttgagtc tgattatgta     420
tgttcatggt catgcaggaa gaaggctcta agcctccgct gaagtataag aaagagacat     480
```

```
gcatgttagc tcattgcgaa ccaatcaagc taagtgaaga ttaaaatgca tgcatgatgc      540
acctaggttt ggt                                                        553
```

<210> SEQ ID NO 100
<211> LENGTH: 553
<212> TYPE: DNA
<213> ORGANISM: Glycine max
<220> FEATURE:
<221> NAME/KEY: misc_feature
<222> LOCATION: (184)..(184)
<223> OTHER INFORMATION: n is a or g
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t

<400> SEQUENCE: 100

```
accaaaccta ggtgcatcat gcatgcattt taatcttcac ttagcttgat tggttcgcaa       60
tgagctaaca tgcatgtctc tttcttatac ttcagcggag gcttagagcc ttcttcctgc      120
atgaccatga acatacataa tcagactcaa gccatgttag aaaaaggaag aacaattaca      180
tagntaaaat aagtctatgt atatatagcc cctaatgagg tgtgaaacat atttcttttc      240
ttatctttat ttgtttgatg tgagattttg taattctcca agactgctta agcaatatat      300
atgcaagcaa gaggttcaat aaggatttga tttcaacctt tgttcttcct ccatgtaact      360
gtagcctctg atgctgcttc ctcctgttgc agcaacattt ctgtaattag gcaagggcac      420
gtgaccttct tcaatttgct tcaaatcatc aacgagcatc tcatagtgcc ttttaacttc      480
ctcnaccgtc ttccctccca cggccctgac caagttcttc nacagatctg gggtttccct      540
gtcgtagatg gcc                                                        553
```

<210> SEQ ID NO 101
<211> LENGTH: 492
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (439)..(439)
<223> OTHER INFORMATION: n is a or t
<220> FEATURE:

```
<221> NAME/KEY: misc_feature
<222> LOCATION: (446)..(446)
<223> OTHER INFORMATION: n is a, c, g, or t

<400> SEQUENCE: 101
atcaaggtct acaaagcaga cacatgtgac atgtaactat atacaaaata tcacgaataa    60
ctccagcagg acctaatccg acatgattgt tacatacaaa cantacaatc acttaacgaa   120
caacaaaact ntaccagaca tgatccaaaa catccttagg cacccaaaag gaatgtaagc   180
tcnaactcta acnttgaaag gtcagaagga gttataagac tcaccagagt cactagacag   240
tggagagtta cgaggagaac ccccaatacc acctacatna ctactatcaa aacctatggc   300
ttcaagccaa aaactaatcc agggtgattc agatgtgtca cctttcatga agatattgac   360
ctgcatgtta agagctcncc gcctcctggg tgtgatatgc tcttggttaa ggacattatg   420
gggctcccta tgtcccgtnc gatttntgtt cagttttcct gggcattaag ccctcctcag   480
aataaaaaaa ag                                                       492

<210> SEQ ID NO 102
<211> LENGTH: 314
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (90)..(90)
<223> OTHER INFORMATION: n is a or g
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (120)..(121)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 102
atgttactct ctctatccaa caagaaaaat gtctcaagca agaatcacgt gctngcanat    60
ngtattccct attattccat catctcctan acgatgannt ttgtagtcat gggcgcctcn   120
nacnncacaa acgccaacaa cataagcacc gccattatgc caacagggaa gaagaggaga   180
acaagcggcg gcngagagag tgatggcaac attagtggta gcactaccat caatgctgtc   240
acggaaacca aaattagaat ggacaccact ctaaagaatc gaaccatgtt ttccccagca   300
ggtcggatac cgtt                                                    314

<210> SEQ ID NO 103
<211> LENGTH: 314
```

```
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (120)..(121)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (193)..(193)
<223> OTHER INFORMATION: n is a or g

<400> SEQUENCE: 103
atgttactct ctctatccaa caagaaaaat gtctcaagca agaatcacgt gctngcanat        60
ngtattccct attattccat catctcctan acgatgannt ttgtagtcat gggcgcctcn       120
nacnncacaa acgccaacaa cataagcacc gccattatgc caacagggaa gaagaggaga       180
acaagcggcg gcngagagag tgatggcaac attagtggta gcactaccat caatgctgtc       240
acggaaacca aaattagaat ggacaccact ctaaagaatc gaaccatgtt ttccccagca       300
ggtcggatac cgtt                                                         314

<210> SEQ ID NO 104
<211> LENGTH: 498
<212> TYPE: DNA
<213> ORGANISM: Glycine max
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (327)..(327)
<223> OTHER INFORMATION: n is a or g

<400> SEQUENCE: 104
acgcttacat tccaagcaaa atatcaaggt gtanaacacc taagaatcct taagtgaccc        60
tacctaattc aatcatttgc actccaagaa aaaattcatg ggtacaagta caacacatga      120
gaatcctgaa gtgaccccag ttttgctact tctagtgttg aactgttgat caattcaatc      180
atttgcactc caagaaaaat atcaaagtgt aaaacaccta agaatcctga attgatccta      240
tctttgttaa ctgctagttg atcaattcaa tcatttacat tgcaatcaaa atcaagatgt      300
agctggatgg ataaggctag cccttgngta gaagctacag aaaacaaata attcaagtgc      360
aaaagcatat atacacgtaa gatcacagaa accaaaatcg tcaaatttcc ttgcctcttt      420
```

| tatcttaagg gttccaaaat tacaggaaat tgattttca tattttggt ttagctacca | 480 |
| gaaagcagct cacaataa | 498 |

<210> SEQ ID NO 105
<211> LENGTH: 498
<212> TYPE: DNA
<213> ORGANISM: Glycine max
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (465)..(465)
<223> OTHER INFORMATION: n is c or g

<400> SEQUENCE: 105

| ttattgtgag ctgctttctg gtagctaaac caaaaatatg aaaaatcaat ttcctgtaat | 60 |
| tttggaaccc ttaagataaa agaggcaagg aaatttgacg attttggttt ctgtgatctt | 120 |
| acgtgtatat atgcttttgc acttgaatta tttgttttct gtagcttcta cncaagggct | 180 |
| agccttatcc atccagctac atcttgattt tgattgcaat gtaaatgatt gaattgatca | 240 |
| actagcagtt aacaaagata ggatcaattc aggattctta ggtgttttac actttgatat | 300 |
| ttttcttgga gtgcaaatga ttgaattgat caacagttca acactagaag tagcaaaact | 360 |
| ggggtcactt caggattctc atgtgttgta cttgtaccca tgaattttt cttggagtgc | 420 |
| aaatgattga attaggtagg gtcacttaag gattcttagg tgttntacac cttgatattt | 480 |
| tgcttggaat gtaagcgt | 498 |

<210> SEQ ID NO 106
<211> LENGTH: 831
<212> TYPE: DNA
<213> ORGANISM: Glycine max
<220> FEATURE:
<221> NAME/KEY: misc_feature
<222> LOCATION: (168)..(168)
<223> OTHER INFORMATION: n is a or g
<220> FEATURE:
<221> NAME/KEY: misc_feature
<222> LOCATION: (485)..(485)
<223> OTHER INFORMATION: n is a, c, g, or t

<400> SEQUENCE: 106

| tcttggtggt tttccggaaa cttgcctaat atgcaagggc catcaaatgc taattatcct | 60 |
| caaggtgctt catttaacag acctcagggt ggccaaatgc ctctgatgca agggtataat | 120 |
| ccttaccagg tgggataata tgcttctgct tcatgaacca cttaaaantt gaaacttctt | 180 |
| ttgttttctt atcttttcc tttatcataa attatgtggt tacttgagtt gtgttttgat | 240 |
| agctattaag cagtgcacat gtcaaagtat aaattatttc tatgtttgca tcgcaacaat | 300 |
| aatgacttcc ctctccccaa acacctttgg aaccatttct tactttctcg tttcatttat | 360 |
| ttcactaata agagatgttg tttgatgcat agctgagtag agtgcataag tatatgcatt | 420 |
| tatttctac tccccttgtc cacttgataa tagaatttat tcaagatctg tcattgagaa | 480 |
| atccntttct tttcatttct ctctggtcca ttgagtaata aatatttata cataatcaag | 540 |
| tgccaaaaaa tgcctgtcga ccaagactgt tagccttgat gatcttatgc aatatctttg | 600 |
| atagtcaatt acttgaaaat ttcacttgat cattggatca aaaagggtct gaatatgtgg | 660 |
| gaggagctag tcttatgtct tgaggattaa ttaatttgtt ttgggaagtg gactgtccaa | 720 |
| ttctgaatgg aaattaattc ttatgttttt gttttgcag tctggtaatc aatctgggat | 780 |

```
gcctccaaac gcaccaccat agaataggaa attgctttct tccttaatag c          831
```

<210> SEQ ID NO 107
<211> LENGTH: 831
<212> TYPE: DNA
<213> ORGANISM: Glycine max
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (485)..(485)
<223> OTHER INFORMATION: n is a or g

<400> SEQUENCE: 107

```
tcttggtggt tttccggaaa cttgcctaat atgcaagggc catcaaatgc taattatcct    60
caaggtgctt catttaacag acctcagggt ggccaaatgc ctctgatgca agggtataat   120
ccttaccagg tgggataata tgcttctgct tcatgaacca cttaaaantt gaaacttctt   180
ttgttttctt atctttttcc tttatcataa attatgtggt tacttgagtt gtgttttgat   240
agctattaag cagtgcacat gtcaaagtat aaattattc tatgtttgca tcgcaacaat   300
aatgacttcc ctctccccaa acacctttgg aaccatttct tactttctcg tttcatttat   360
ttcactaata agagatgttg tttgatgcat agctgagtag agtgcataag tatatgcatt   420
tattttctac tccccttgtc cacttgataa tagaatttat tcaagatctg tcattgagaa   480
atccntttct tttcatttct ctctggtcca ttgagtaata aatatttata cataatcaag   540
tgccaaaaaa tgcctgtcga ccaagactgt tagccttgat gatcttatgc aatatctttg   600
atagtcaatt acttgaaaat ttcacttgat cattggatca aaaagggtct gaatatgtgg   660
gaggagctag tcttatgtct tgaggattaa ttaatttgtt ttgggaagtg gactgtccaa   720
ttctgaatgg aaattaattc ttatgttttt gttttgcag tctggtaatc aatctgggat   780
gcctccaaac gcaccaccat agaataggaa attgctttct tccttaatag c            831
```

<210> SEQ ID NO 108
<211> LENGTH: 852
<212> TYPE: DNA
<213> ORGANISM: Glycine max
<220> FEATURE:
<221> NAME/KEY: misc_feature
<222> LOCATION: (131)..(131)
<223> OTHER INFORMATION: n is a or c
<220> FEATURE:
<221> NAME/KEY: misc_feature
<222> LOCATION: (480)..(480)
<223> OTHER INFORMATION: n is a, c, g, or t

<400> SEQUENCE: 108

```
atatggatat atattaacat ttctgacttc tatttgaatc ccttttagga agaagcattt    60
tgaacaaaaa agtgtgatag ccctttttat tgacagagtt ccgccacaag aagcttgtac   120
gtatagacaa nggagagtaa actagagtaa ataagggtaa agaaaaata ttgtagggga   180 gggagaagca aactcaatcg aataattccc acgtggttga ggatggagga tgatcaaaga   240
tctcccactt ggttgtaaca acaacaggtt ttattcttgc attagatacc ttaagttgat   300
ccagtttttc aacacatttt tgcactctct ttccctggaa aatgtaatca tatcagatta   360
ttaagcatat aaccaattac tccatgtgac ttaccaattg aggagaaaat gtacactatg   420
ctcctattga acttttttgg tatagtcgac aaaagactgt atacttcata ttcagcaatn   480
```

| | |
|---|---|
| ttttccatgg taaaactatt ctaaataaat aaagcgaatt ttctttcatt tttttactct | 540 |
| ttctttcttc ttcttttca cttaatttta ataaatgagc acgaccaagt cctctttaat | 600 |
| taattttatg ataagattaa agaataata aatttattta aagaggatgt tcacccaccc | 660 |
| ataccaaaat atttagaaac attatctatc tatagcaatt agaaacattt atttccaaat | 720 |
| gaaaccaaac aaaatgcatg cgggaattaa tataagtact tgacaggaaa gtagaattcc | 780 |
| attgaaaata cctgcaaatt tttaaatgga gaggcaccgc cttctgcaga aatgctttct | 840 |
| aattgatgct gt | 852 |

<210> SEQ ID NO 109
<211> LENGTH: 852
<212> TYPE: DNA
<213> ORGANISM: Glycine max
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (480)..(480)
<223> OTHER INFORMATION: n is a or g

<400> SEQUENCE: 109

| | |
|---|---|
| atatggatat atattaacat ttctgacttc tatttgaatc cctttttagga agaagcattt | 60 |
| tgaacaaaaa agtgtgatag ccctttttat tgacagagt ccgccacaag aagcttgtac | 120 |
| gtatagacaa nggagagtaa actagagtaa ataagggtaa aagaaaaata ttgtagggga | 180 |
| gggagaagca aactcaatcg aataattccc acgtggttga ggatggagga tgatcaaaga | 240 |
| tctcccactt ggttgtaaca acaacaggtt ttattcttgc attagatacc ttaagttgat | 300 |
| ccagtttttc aacacatttt tgcactctct ttccctggaa aatgtaatca tatcagatta | 360 |
| ttaagcatat aaccaattac tccatgtgac ttaccaattg aggagaaaat gtacactatg | 420 |
| ctcctattga actttttgg tatagtcgac aaaagactgt atacttcata ttcagcaatn | 480 |
| ttttccatgg taaaactatt ctaaataaat aaagcgaatt ttctttcatt tttttactct | 540 |
| ttctttcttc ttcttttca cttaatttta ataaatgagc acgaccaagt cctctttaat | 600 |
| taattttatg ataagattaa agaataata aatttattta aagaggatgt tcacccaccc | 660 |
| ataccaaaat atttagaaac attatctatc tatagcaatt agaaacattt atttccaaat | 720 |
| gaaaccaaac aaaatgcatg cgggaattaa tataagtact tgacaggaaa gtagaattcc | 780 |
| attgaaaata cctgcaaatt tttaaatgga gaggcaccgc cttctgcaga aatgctttct | 840 |
| aattgatgct gt | 852 |

<210> SEQ ID NO 110
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (254)..(254)
<223> OTHER INFORMATION: n is a, c, g, or t

<400> SEQUENCE: 110

| | |
|---|---|
| gatatacata tagaccgagc aaaatcaata cacttcagca agctgaacgt ctgggtgggc | 60 |
| ctattttgtc tcttggcacc attgagcctc agccgagatc tatagagaaa gatgtttcta | 120 |

```
cottgtcaat aacacaaccc aaaaacagaa atcctgtgta tgaacctctg ttatcagatt    180
ctccaaatgc ctccagaaga tcttttggag caggaacacc atttgatttt ttccagtcac    240
aatcaagatt ntcngtgtcg tctagctaca cacgaaattg caaggacaac tgagattaag    300
gagcaattgg aagagctcca gatgccgcat cttagttgta tatcccgttt tatcaaaact    360
aacaaagtac aatgttaatt ccgtgtatac taatgttatt taaagtgcca ttagataact    420
ggttatacaa aaaggcaata ggaaatgaat tttcacgatt ttatgtagat tatctgatta    480
acttgatatt atttttgttt t                                              501
```

<210> SEQ ID NO 111
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t

<400> SEQUENCE: 111

```
agcatttgct agcgcgtgaa gctgaagcag caaggtggag tcaaaggaaa caattgttgg    60
cagcagcagg agtaggtaga ggaggaggaa gcaagagaga agtgaaccct tggcttacac   120
caaccatggg tttccctccc atgacatcaa tgcaccattt tagaccttta catgtatggg   180
ggcatcaaac catggaccag tccttcatgc acatgtggcc taaacatcca ccatacttgc   240
cgtcaccgcc ngtatggccg ccacaaacag ctccgtctcc accggcaccn gaccctctat   300
attggcacca acaccaacgg gntnactctt ttgactttg aacattctca cttctctttc   360
ttttactata ttcaaaactc atttaattat aattgactat tgagttggtg aataaaagt    420 ataggtat tataaatttt taatattata ttcgattttt ccatataaaa aatattaatt    480
gactcaaaaa atgattgtaa c                                             501
```

<210> SEQ ID NO 112
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or c

<400> SEQUENCE: 112

```
agattcccag cgttggtaag gctggttctg ctccttcgga ttctcctaag gatactaatg    60
ctgccaatgg gatgaatgtg ggtttcggac ttgttcttgg acttggcttc atttgcatgg   120
gagctctctc ttgatcacca gaaaatactt cattgtcaat gtgtcgtctt atcttttttc   180
ttttactctc acttcttcat ttcctaatct ttcttttctt ctacgggcaa aaggaactgt   240
gttgggtttt nttgagcctc attctttcta tttaatgccc tcttttttat gtatttaatt   300
```

```
taatccttgt cttgtattta ctatttaatt tggatcacat gattttgttt atgaggaaaa    360
cgaacaccta gctactttag ctttttttt ttcttttatt tctcatccta ataaaacata    420
aataaatgga tgctcaacca ttgtgtcatg tatgtcattc ttcatttctt tgctttttta    480 cttttaact ttaaggaatg g                                              501
```

<210> SEQ ID NO 113
<211> LENGTH: 335
<212> TYPE: DNA
<213> ORGANISM: Glycine max
<220> FEATURE:
<221> NAME/KEY: misc_feature
<222> LOCATION: (260)..(260)
<223> OTHER INFORMATION: n is a or g

<400> SEQUENCE: 113

```
tcatcccatt ggcagcatta gtatccttag gagaatccga aggagcagaa ccagccttac     60
caacgctggg aatctcagga gtgctcttag aacccttagg agaaggagcc gcagaagaag    120
cacgagtctt ggtggttccg aagagttcca acggcaacag aaccttgtca acctggtaca    180
cagccagagg aaacttctcc ctcagtgggt tgttgagctg cgtctgcacc accccctgtgg    240 agatgttcac ctggttaccn ccttggccgg tgaagttcag cccccaggtc ccttcttct     300 ccgtggcctg cgtcctcacg ggttgctca cgggc                               335
```

<210> SEQ ID NO 114
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or a
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t

<400> SEQUENCE: 114

```
attgtggatg ttgattcttg ggattgtcag tctcgatatc catcaggcca ttgtgtgcga     60
actatagggg agataggtga tagagatact gaaagcgagg tatggaatat tggattttgt    120 acgattctc tctttgtatc aatagtggga aaaattagta taatcatcag tcactagagc    180
aagtcattag gaacttggca acttgcttgt gctctctgca acttactcag cttgtttaaa    240
aactgggggg nttgagggtc agttccgtca gcaacaaata acngtcaaga gagaacaaaa    300
tccaaaaccc tttcaattct gaagatttcg ctctctttct tcttgagaaa caaactctcc    360
ttcgcttcag aagcttcttc ctctgatttc tgaccatgaa ttcccaaacc actganttcc    420
ccatgaatga agctcgactt ggaagcaata tcttatagct tcaagctccc tttcatcagg    480
catggggaac tcagtggttt g                                             501
```

<210> SEQ ID NO 115
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is c or g

<400> SEQUENCE: 115

```
agcttttcct gcattattat tcgtgtgaaa atttggtatt ggtactaacg ttagcttttg      60
tgatcaatag attttcaaat gaaaaatcag aagcaagaaa ctctcagtct atggtgcctt     120
cagaagtgaa atccacatct gtttatcctc ctgaggtaca tgataaatta ataattatta    180
tgagcatatt tataaatttc gtaaaaaaaa tatttatatg gcttttggac attttttttc    240
ctatgtgtat naggagtaac gagtggagat atgaccagaa gcagtactgg gagaaaaatg    300
gctttgctca atcagatttt tatccttgat atggatggac atatagattt atgatgcgga    360
atgtgaaaaa gctaattata tacgttgata tgttgcatcc cgcggaaatt catgtatgtt    420
aggtaacatc aattttcctg aaaacattac acataatgta attgctgtta aatttaacga    480
gtaaataatt tatgttcaaa c                                              501
```

<210> SEQ ID NO 116
<211> LENGTH: 501
<212> TYPE: DNA
<213> ORGANISM: Glycine max
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (251)..(251)
<223> OTHER INFORMATION: n is g or a
<220> FEATURE:
<221> NAME/KEY: misc_feature
<222> LOCATION: (440)..(440)
<223> OTHER INFORMATION: n is a, c, g, or t

<400> SEQUENCE: 116

```
ctcactcact cactcttcct gtgaacgaca ccgacaacat gttaaagcaa gacaatgcca     60
cacacaattt ctctctctct ctgctctctt ggatgacaag ttaacacaga aaagaaaatg    120
gacctcttaa ccactctcaa atctatcttc tgctactttc atcatcctca ttgcacttga    180
aagttctacg agttgaagca ttcttttaca taattctctt tctgaacaaa aaaaanaac    240 aacaacgtgc nagtgtgggt gtacacgaca gcataagcat gttctgtcgg tccctcgttc    300
caaactcaac aaaaccgagc ctattgcatt cccacattct tctccctcac cccatgtgcc    360
actgctagca ttccctcttc tgcatttcca tgtaagagga gggacttaat aaggttaagg    420
atccaaagct ttcaactttn aactttgaag tttgaatctc actctctttt tggctcatct    480
atggacccaa acactcgtct t                                              501
```

<210> SEQ ID NO 117
<211> LENGTH: 670
<212> TYPE: DNA
<213> ORGANISM: Glycine max
<220> FEATURE:
<221> NAME/KEY: misc_feature
<222> LOCATION: (163)..(163)
<223> OTHER INFORMATION: n is a or g

<400> SEQUENCE: 117

```
tatgagcaac ttcaccacac ccacatggct gaatgatttt attgagtctt gattcacaaa     60
aagccattga caccttacat caaagcaaag aagctcctag ctaacaaaac aacatcaatg    120
cattcaaaat gataggatgt tatctatcca ctcttttgag acntcatttt cttcctccat    180
gcaagtgcaa ggtctctaga acaacatggg atgttggagg ctcctcccac ttaggcaaaa    240
```

```
ccaacaagtt tctcactaat ctcccagatc ttacgagcct tctctgtatc actggcctcc      300
tgagacaact ggttttcaaa cgaagctgat gctttgttcc agctccagta aacaccagat      360
tttgttaggc ttggatcact tacaacctat ataaaagaca accacacatg agaaataaag      420
atatttgaaa acttcatact cttgtagtca ttatcttccc tagagggtta ttattgatat      480
tacctgagca agtctctttc ctgcttcatc ttctgagaca tagcctttgg ttatgtactt      540
ctggaatgga gggaacagag ttctgaacaa gggaatgtgc tctctgaaca ggcctgttgt      600
ggcaatgcaa ccggggtaaa gggaagcaaa tgtgattcca gtttcctcat ggaatcgtct      660
gtggaattct                                                            670
```

<210> SEQ ID NO 118
<211> LENGTH: 494
<212> TYPE: DNA
<213> ORGANISM: Glycine max
<220> FEATURE:
<221> NAME/KEY: misc_feature
<222> LOCATION: (46)..(46)
<223> OTHER INFORMATION: n is a or c

<400> SEQUENCE: 118

```
attggttgaa ttctgggctc catggtgtgg tccctgccgt atgatncatc cgataattga       60
tgagctggca aaggaatatg ttggtaggct taagtgctac aaactcaata ctgatgaaag      120
cccttcaacc gctactcggt acgggatccg aagtatccca actgtcatta ttttcaagaa      180
tggtgagaag aaagatacag ttattggagc tgtgcccaag acaacattga cctcaagcat      240
agaaaaattc ttgtgaggtg gtaagcaaag gcttcagctg gaagtaaagc tattttttctc      300 gttagcttcc tctcatctaa gccaaatatc tcaagtttgg gtgatttgtt tcttaaataa      360
ccatttatgg tcctgtataa ttatggatca accatatttt ctgtgctgtt tacataatcg      420
tagttgttgc gtaaagttgc tatctattat agtacgattt aaaattccgt ttacatcttt      480
ggcttcctgc tcct                                                       494
```

<210> SEQ ID NO 119
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 119

```
ttcactaccc attttaggat tttttatttt aagtcatttt aagagattat tgatgcatcc       60
atttttagtt actgagggtc ctggactatc agttgtgccc aaatgaggtt tgcaaattcc      120
aagtcagcct cgtaccatat ttggaggaat aaagtgattt caaaagttct aaaaaatact      180
tgagtatttt catcaaacag aatgattaaa cacgcacgat ataccatctg agagagcttg      240
tttgcatgtg ncagagcaaa cataggtaag gtctttcatc ttccaccaga agaactaat       300 aataaagacc ttcttcatgt tgcaatggct gcattaatat tattgtgaca ggccacattc      360
aaataatcta cgaatacaat gttacctaaa aataaaataa aatatagcta ataatagaga      420
aattgatgta tttcttgaag ttcaaacacg gatgaatcaa cagataatct cttcatctct      480
atactttctt gcacatgtct c                                               501
```

<210> SEQ ID NO 120
<211> LENGTH: 501

```
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g

<400> SEQUENCE: 120
tccattccct ttgcacctga actcgcgctc gatgaaggga cacgtggcgg gatcataggg    60
cgggtacgat tcgtccacca cccacgttcc cgtgaacaca tcgcactgcg cataatccaa   120
agccgaagaa gaacccttc ctctcacttt cgacaacaac aacccatgaa gaaggaagaa   180
gaacagctgc agacgacaag agacaacacc ctcacccatt ttcttaatct ctctctcttg   240
ggtacgagga nagacaaaga atatggtaat gcagaagaaa ggggtatgga gagggttctt   300
ttctctctga tgagttatga gtatttgtgt tgttctatcc actaagcttg tggcatttat   360
atacatacaa ctaagtgcgg ctgcatgtgt ttatgcaaat tgaatgggga cactcgagag   420
agagagagag aaggagtttt ttttttttt tttctttttt tccttctact tcttcttctt   480
attatcatta ttaaatgatg t                                             501

<210> SEQ ID NO 121
<211> LENGTH: 119
<212> TYPE: DNA
<213> ORGANISM: Glycine max
<220> FEATURE:
<221> NAME/KEY: misc_feature
<222> LOCATION: (61)..(61)
<223> OTHER INFORMATION: n is c or g

<400> SEQUENCE: 121
tttgacatca aggttttaaa ctgagcccat ggttacaatt tcgtcccatt tttttatatt    60
ntgagaaatt acagataaat gttgttgaag ttgcagttga aacacaacaa agaactccc    119

<210> SEQ ID NO 122
<211> LENGTH: 501
<212> TYPE: DNA
<213> ORGANISM: Glycine max
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (254)..(255)
<223> OTHER INFORMATION: n is a, c, g, or t

<400> SEQUENCE: 122
aagtccaaaa ttattctgac caaacattcc tggagtgcca ccgaagctgc ttgcaccaac    60
tatttaagac catacaataa aatagtcatt caaaatatta atccttcaat cattgcatga   120
aacaaaacaa atagtataag cattatataa tatattgaac tgancaggtt gtgtctggcc   180
aaagttgcca aagccaaaag caccactcga ctgagcaggt tgtgcagatt gaaaaggtgt   240
tgaaatggac ngcnncagtt ataaaagtca aacaaaagta ttagaaagtc aaaatgcagt   300
acaaacttga gcgtttatta tctcacaggg gaaatccact atacatgcat atataagaca   360
aaggaaactt gaaatggac aaaaagatgc taagtttgag cacaaatatc caaagtaaa   420 ttagttattt taaggatct tcaattttc cctgtaagtt ctcatatcaa taacacaaat   480
```

```
aaattcaaag gtgcaatgtg c                                              501

<210> SEQ ID NO 123
<211> LENGTH: 501
<212> TYPE: DNA
<213> ORGANISM: Glycine max
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g

<400> SEQUENCE: 123
gatgaagaaa tctcagcaga aaanagatct tcaagatttg atggagttag gatcttggac    60
cgaccagatc tactcacaga accagcacca gnccgcggct gtaagtaaca gctcaagtca   120
ttcaaaggat gctgctgctg gccatcaaga tcagacatca tgttcaagtc gtctggtggc   180
atgtcgcggg cactaaggga agacctcaat cgactagact gaagattgct tcctggtaaa   240
tgaagagctg ncacatttgg ctgtgcccaa gcagaagaca gtgacatgcc atttgcagat   300
ggggacattg gttgcccaaa gtgggatggc gacatggaag agaccgaaga aggcgagccc   360
ggcaaaaggc tcatcgcagc agccatgtcc atgacattag gagccgaggc agatgacctg   420
ggcgaaggga cagcagatcc agtggacaca tacagcggac gaagctcctc cgcagtgtga   480
gcaaaaaaac acacccttcg a                                              501

<210> SEQ ID NO 124
<211> LENGTH: 303
<212> TYPE: DNA
<213> ORGANISM: Glycine max
<220> FEATURE:
<221> NAME/KEY: misc_feature
<222> LOCATION: (155)..(155)
<223> OTHER INFORMATION: n is a or g
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t

<400> SEQUENCE: 124
aaaagcgcgt ttgcttttcg gttataacgt gtatttacat aacgtgccga ttatatcttc    60
atcacaaaat ggtcaacaac aattccgagc atcatgtcat ccactactca cacttagctg   120
ctgctccctc tccgtaacac tataatttct cgagngcaat ttcgtcacaa aaaatgcgt   180 agtagtgttc ccagatgctt aaaaangtag tacgaaaaaa attgcggaaa accagatctc   240
cctgcatgaa tcaggcaacc tcngggagag gaggcacgtt caggtcaaga tcaaggagca   300
cgc                                                                  303

<210> SEQ ID NO 125
<211> LENGTH: 646
<212> TYPE: DNA
<213> ORGANISM: Glycine max
<220> FEATURE:
<221> NAME/KEY: misc_feature
```

```
<222> LOCATION: (108)..(108)
<223> OTHER INFORMATION: n is a or g

<400> SEQUENCE: 125
gaggaagatc ttgcaacata cggagccttg tatgagaaat ctggattcca aactgcattg    60
cagattccat ataggtgcta gcttttgttc gtcattgccc ttttagtnaa aaatgttgtt   120
tcttactaca aagcaatgaa acatggtct  ctcgaactct caaattttct tatctctggg   180
tgagttcttg ttaattgttt gttggttttg tttgtatttg taggtcatta ggtgaagtgc   240
ttagcttgcc agatcctgtg gttaaagttc cggcatttct gataatgggt ggcaaggatt   300
atgttctgaa gtttccaggg attgaagatt taacaaaggg tgaaaaagca aaatggtttg   360
ttccaaactt ggaggttaca tttatcccgg agggaaccca ttttgttcaa gaacagtttc   420
ccgagaaggt gaatcagctt attcttgact tccttgccaa gcacacttga tattggactg   480
tcgtcatgaa tggtgtatgt ggattgtgaa ctgtgggaaa atcagacaaa gtgcagcaca   540
aaatgatcga ttgctgaagc taaatgatgc aaagcttgct ggtagagctt tgttagatga   600
atttcttgta caaagaattc gtgaaatatg cgactgagtt gtctag                  646

<210> SEQ ID NO 126
<211> LENGTH: 492
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (131)..(131)
<223> OTHER INFORMATION: n is a or c
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 126
atcaaggtct acaaagcaga cacatgtgac atgtaactat atacaaaata tcacgaataa    60
ctccagcagg acctaatccg acatgattgt tacatacaaa cantcaatc  acttaacgaa   120 caacaaaact ntaccagaca tgatccaaaa catccttagg cacccaaaag gaatgtaagc   180
tcnaactcta acnttgaaag gtcagaagga gttataagac tcaccagagt cactagacag   240
tggagagtta cgaggagaac ccccaatacc acctacatna ctactatcaa aacctatggc   300
ttcaagccaa aaactaatcc agggtgattc agatgtgtca cctttcatga agatattgac   360
```

```
ctgcatgtta agagctcncc gcctcctggg tgtgatatgc tcttggttaa ggacattatg    420
gggctcccta tgtcccgtnc gatttntgtt cagttttcct gggcattaag ccctcctcag    480
aataaaaaaa ag                                                        492

<210> SEQ ID NO 127
<211> LENGTH: 646
<212> TYPE: DNA
<213> ORGANISM: Glycine max
<220> FEATURE:
<221> NAME/KEY: misc_feature
<222> LOCATION: (108)..(108)
<223> OTHER INFORMATION: n is a or g

<400> SEQUENCE: 127
gaggaagatc ttgcaacata cggagccttg tatgagaaat ctggattcca aactgcattg     60
cagattccat ataggtgcta gcttttgttc gtcattgccc ttttagtnaa aaatgttgtt    120
tcttactaca aagcaatgaa acatggtct ctcgaactct caaattttct tatctctggg     180
tgagttcttg ttaattgttt gttggttttg tttgtatttg taggtcatta ggtgaagtgc    240
ttagcttgcc agatcctgtg gttaaagttc cggcatttct gataatgggt ggcaaggatt    300
atgttctgaa gtttccaggg attgaagatt taacaaaggg tgaaaagca aaatggtttg     360 ttccaaactt ggaggttaca tttatcccgg agggaaccca ttttgttcaa gaacagtttc    420
ccgagaaggt gaatcagctt attcttgact tccttgccaa gcacacttga tattggactg    480
tcgtcatgaa tggtgtatgt ggattgtgaa ctgtgggaaa atcagacaaa gtgcagcaca    540
aaatgatcga ttgctgaagc taatgatgc aaagcttgct ggtagagctt tgttagatga    600
atttcttgta caaagaattc gtgaaatatg cgactgagtt gtctag                  646

<210> SEQ ID NO 128
<211> LENGTH: 316
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 128
tgctagaaaa tcaggtgtga atcaaatgga cagagaaacc aaagcaaaag ctttcaaata     60
tagggtatga ttctttcttt ccttttaat tgtctaagtt aaattctagg aaatagaagc    120
tacttattca ctagctaatg aaagttaaac caaactttaa ttcttttatg tattgtttca    180
tgttatgaca caggaaaaat gaatcaagaa agcgttgcac aagggtatac tccagcaatg    240
ttcaaactga ngganttttgg tgctgcaaag tgtttctata atgacaaaag ngttaggaga    300
ctagtagggc aaggga                                                  316

<210> SEQ ID NO 129
<211> LENGTH: 501
<212> TYPE: DNA
<213> ORGANISM: Glycine max
<220> FEATURE:
<221> NAME/KEY: misc_feature
```

```
<222> LOCATION: (119)..(119)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (343)..(343)
<223> OTHER INFORMATION: n is a, c, g, or t

<400> SEQUENCE: 129
tccctcactg atttctctgc accccttcca tttcccacgt tctcaaaaca actttctcaa      60
atatcatgct acgtacccca ccaagcatag taaaccaaac tgccacgttt ccaaagtgnc     120
atgccatagt aatcaaaaca actcaacaca aaacctagaa gaaggaaaac tatcacacaa     180
cttaggagga aaaaatagga gggattttct cattggcttt ggagaacttt acggtgcttc     240
tactcttagc nacaataaca acaaccttt agccatcgct gctccaattc tccctcctga     300
cctagaaact tatggttcac cagagttacc aactgatgta aaccggcca ccatttgttg     360 ccctccagta tcttctatcg tcatagactt caagcttcct tgtaacattc cgattttct     420 tttctaatta tataaatata ttaattatta ttaaacattt taattttct tgttttaatt     480 aaaataaata atttggcaat t                                               501

<210> SEQ ID NO 130
<211> LENGTH: 312
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (62)..(62)
<223> OTHER INFORMATION: n is g or a
<220> FEATURE:
<221> NAME/KEY: misc_feature
<222> LOCATION: (66)..(66)
<223> OTHER INFORMATION: n is a, c, g, or t

<400> SEQUENCE: 130
tcccttgccc tactagtctc ctaacnctt tgtcattata gaaacacttt gcagcaccaa      60
antccntcag tttgaacatt gctggagtat acccttgtgc aacgctttct tgattcattt     120
ttcctgtgtc ataacatgaa acaatacata aagaattaa agtttggttt aactttcatt     180
agctagtgaa taagtagctt ctatttccta gaatttaact tagacaatta aaaggaaag     240 aaagaatcat accctatatt tgaaagcttt tgctttggtt tctctgtcca tttgattcac     300
acctgatttt ct                                                         312

<210> SEQ ID NO 131
<211> LENGTH: 501
<212> TYPE: DNA
<213> ORGANISM: Glycine max
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (251)..(251)
<223> OTHER INFORMATION: n is c or a
<220> FEATURE:
<221> NAME/KEY: misc_feature
<222> LOCATION: (397)..(397)
```

<223> OTHER INFORMATION: n is a, c, g, or t

<400> SEQUENCE: 131

```
tgtggggat aaacaggcaa ggacagagat gtcttttcat caacattgta gtcgaaatag      60
caaaagtagt agtggaaata gtagctttcc aagtgagtct tgacagggca gaaaaactga    120
atccaattat ccaaaccggt tggttaaact ctaggcagcc gaaaggcaca aaaaaacaat    180
gtcctcttga aaattttcaa ttgtctattg acacgaccaa tacacaaaan cacagccaca    240
aaggcagcat natcagagag caacaatgga agaagaaaaa gaagaccaaa agctcctgac    300
ataccccac tactggggct tcaccccaga agaggactac tacaaacaac aaggaatcac     360
atccacaagc tccttcttca ccactcccca aggcctnaaa ctcttcacaa gatcctggct    420
cccaaaccct aacactcctc cccgtgccct aatcttcatg gttcacggct acggcaacga    480
catctcctgg accttccaat c                                              501
```

<210> SEQ ID NO 132
<211> LENGTH: 303
<212> TYPE: DNA
<213> ORGANISM: Glycine max
<220> FEATURE:
<221> NAME/KEY: misc_feature
<222> LOCATION: (251)..(251)
<223> OTHER INFORMATION: n is a or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 132

```
tgctagaaaa tcaggtgtga atcaaatgga cagagaaacc aaagcaaaag ctttcaaata     60
tagggtatga ttctttcttt ccttttaat tgtctaagtt aaattctagg aaatagaagc    120
tacttattca ctagctaatg aaagttaaac caaactttaa ttcttttatg tattgtttca    180
tgttatgaca caggaaaaat gaatcaagaa agcgttgcac aagggtatac tccagcaatg    240
ttcaaactga nggantttgg tgctgcaaag tgtttctata atgacaaaag ngttaggaga    300
cta                                                                  303
```

<210> SEQ ID NO 133
<211> LENGTH: 501
<212> TYPE: DNA
<213> ORGANISM: Glycine max
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (310)..(310)
<223> OTHER INFORMATION: n is a, c, g, or t

<400> SEQUENCE: 133

```
ctccaccaca gtccccaacc tgggcttccc gcggtaacgc aaagggttca tgtcggcgat     60
gacttttttg tggtcaactt tgacggactt gtagagaaga tcgggagtgg gaacaatggg    120
gagagtgggg aagaatcttg ataggaaagt gaggatttgc gggattggcc atttgggtcg    180
```

```
cacgttgtcg gagattttgc acatnggggc caccaaaacg gcaccttgga agggttgaga    240
tttgggttcc ntttcggagt tgacgaggtg gatgaggagg gagattgcgg cgcccatgga    300
ctcgccgtan aggaaggaag ggaggttagg gttttgggtt ctgatggaat tgaagaagga    360
gaggcaatcg tgtgcggcga ggtgtacgtt agggacgtag gctttgaggc cctgggagtg    420
gccgtggccc tggaggtcta gggcgaagca tgagaaggag ttttgggcga ggaagatagg    480
ggttgattgg aaggtccagg a                                              501
```

```
<210> SEQ ID NO 134
<211> LENGTH: 529
<212> TYPE: DNA
<213> ORGANISM: Glycine max
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t
<220> FEATURE:
<221> NAME/KEY: misc_feature
<222> LOCATION: (251)..(252)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (361)..(361)
<223> OTHER INFORMATION: n is a or c
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t

<400> SEQUENCE: 134
tgacctcata catgtcccct tcgtttaaaa tacatttctt ttgtcttggc catcactatt    60
```

```
actaatattg gtggtttaat caccaaatga cgatgatgga gtagagttgg ggtaatgagg    120
ttgagnttga tgatgatcat agttgtttgt gttgaagcat tgccccacct cttttcatca    180
cccaaacact atttgttgcc attccaattt ggtaaattct tcttcttttt ttgtnttnan    240
tgnttnnctt nntctctcnt cnattattta gaagataaga gcttggaatt caaaggatag    300 tttttagca cctgcacctt tggggccata ttctcnagat aagggcattt ttgtcttaaa     360
natgcatgtg cacaacacat gacacacttg ttatgttctt gaccgatncg gnaaagtcaa    420
aatgagacac cgtggcgcgc cagaggaacc accgcaaccc caaccttcat ttcctcaccg    480
gaaaaagaag cgcaagcgca gagccaccgc caccgccacc gtcggnttc              529
```

<210> SEQ ID NO 135
<211> LENGTH: 527
<212> TYPE: DNA
<213> ORGANISM: Glycine max
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (402)..(402)
<223> OTHER INFORMATION: n is c or g

<400> SEQUENCE: 135

```
gaanccgacg gtggcggtgg cggtggctct gcgcttgcgc ttcttttcc ggtgaggaaa      60 tgaaggttgg ggttgcggtg gttcctctgg cgcgccacgg tgtctcattt tgactttncc    120
gnatcggtca agaacataac aagtgtgtca tgtgttgtgc acatgcatnt ttaagacaaa    180
aatgcccttt tctngagaat atggccccaa aggtgcaggt gctaaaaaac tatcctttga    240
attccaagct cttatcttct aaataatnga ngagaganaa gnaancantn aanacaaaaa    300
aagaagaaga atttaccaaa ttggaatggc aacaaatagt gtttgggtga tgaaaagagg    360
tggggcaatg cttcaacaca aacaactatg atcatcatca anctcaacct cattacccca    420
actctactcc atcatcgtca tttggtgatt aaaccaccaa tattagtaat agtgatggcc    480
aagacaaaag aaatgtattt taaacgaagg ggacatgtat gaggtca                  527
```

<210> SEQ ID NO 136
<211> LENGTH: 529
<212> TYPE: DNA
<213> ORGANISM: Glycine max
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (194)..(194)
<223> OTHER INFORMATION: n is a or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (278)..(279)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (404)..(404)

<223> OTHER INFORMATION: n is a, c, g, or t

<400> SEQUENCE: 136

```
gaanccgacg gtggcggtgg cggtggctct gcgcttgcgc ttcttttttcc ggtgaggaaa    60
tgaaggttgg ggttgcggtg gttcctctgg cgcgccacgg tgtctcattt tgactttncc   120
gnatcggtca agaacataac aagtgtgtca tgtgttgtgc acatgcatnt ttaagacaaa   180
aatgcccctta tctngagaat atggccccaa aggtgcaggt gctaaaaaac tatcctttga   240
attccaagct cttatcttct aaataatnga ngagaganna agnnaancan tnaanacaaa   300
aaaagaagaa gaatttacca aattggaatg gcaacaaata gtgtttgggt gatgaaaaga   360
ggtggggcaa tgcttcaaca caaacaacta tgatcatcat caanctcaac ctcattaccc   420
caactctact ccatcatcgt catttggtga ttaaaccacc aatattagta atagtgatgg   480
ccaagacaaa agaaatgtat tttaaacgaa ggggacatgt atgaggtca              529
```

<210> SEQ ID NO 137
<211> LENGTH: 14
<212> TYPE: DNA
<213> ORGANISM: Artificial
<220> FEATURE:
<223> OTHER INFORMATION: SNP probe sequence

<400> SEQUENCE: 137
caagctgctc acga    14

<210> SEQ ID NO 138
<211> LENGTH: 18
<212> TYPE: DNA
<213> ORGANISM: Artificial
<220> FEATURE:
<223> OTHER INFORMATION: SNP probe sequence

<400> SEQUENCE: 138
tatgtcattt gtgagggt    18

<210> SEQ ID NO 139
<211> LENGTH: 18
<212> TYPE: DNA
<213> ORGANISM: Artificial
<220> FEATURE:
<223> OTHER INFORMATION: SNP probe sequence

<400> SEQUENCE: 139
tgggaacctc tatcatat    18

<210> SEQ ID NO 140
<211> LENGTH: 14
<212> TYPE: DNA
<213> ORGANISM: Artificial
<220> FEATURE:
<223> OTHER INFORMATION: SNP probe sequence

<400> SEQUENCE: 140
tgttccagct ctca    14

<210> SEQ ID NO 141
<211> LENGTH: 15
<212> TYPE: DNA
<213> ORGANISM: Artificial
<220> FEATURE:
<223> OTHER INFORMATION: SNP probe sequence

<400> SEQUENCE: 141

```
tgatgctttg gtgca                                                      15

<210> SEQ ID NO 142
<211> LENGTH: 18
<212> TYPE: DNA
<213> ORGANISM: Artificial
<220> FEATURE:
<223> OTHER INFORMATION: SNP probe sequence

<400> SEQUENCE: 142
tataccgtca atactaac                                                   18

<210> SEQ ID NO 143
<211> LENGTH: 19
<212> TYPE: DNA
<213> ORGANISM: Artificial
<220> FEATURE:
<223> OTHER INFORMATION: SNP probe sequence

<400> SEQUENCE: 143
catcatcatg ttcagaaac                                                  19

<210> SEQ ID NO 144
<211> LENGTH: 17
<212> TYPE: DNA
<213> ORGANISM: Artificial
<220> FEATURE:
<223> OTHER INFORMATION: SNP probe sequence

<400> SEQUENCE: 144
ctcatgggag tcatctt                                                    17

<210> SEQ ID NO 145
<211> LENGTH: 15
<212> TYPE: DNA
<213> ORGANISM: Artificial
<220> FEATURE:
<223> OTHER INFORMATION: SNP probe sequence

<400> SEQUENCE: 145
cagaaacaag ccctc                                                      15

<210> SEQ ID NO 146
<211> LENGTH: 15
<212> TYPE: DNA
<213> ORGANISM: Artificial
<220> FEATURE:
<223> OTHER INFORMATION: SNP probe sequence

<400> SEQUENCE: 146
agcaacttcc gcgat                                                      15

<210> SEQ ID NO 147
<211> LENGTH: 17
<212> TYPE: DNA
<213> ORGANISM: Artificial
<220> FEATURE:
<223> OTHER INFORMATION: SNP probe sequence

<400> SEQUENCE: 147
accccatcag agaaaac                                                    17

<210> SEQ ID NO 148
<211> LENGTH: 17
<212> TYPE: DNA
```

```
<213> ORGANISM: Artificial
<220> FEATURE:
<223> OTHER INFORMATION: SNP probe sequence

<400> SEQUENCE: 148
aagccagcct taatatt                                                  17

<210> SEQ ID NO 149
<211> LENGTH: 15
<212> TYPE: DNA
<213> ORGANISM: Artificial
<220> FEATURE:
<223> OTHER INFORMATION: SNP probe sequence

<400> SEQUENCE: 149
ctgaccacga acacg                                                    15

<210> SEQ ID NO 150
<211> LENGTH: 17
<212> TYPE: DNA
<213> ORGANISM: Artificial
<220> FEATURE:
<223> OTHER INFORMATION: SNP probe sequence

<400> SEQUENCE: 150
atctgaggcc ttgatga                                                  17

<210> SEQ ID NO 151
<211> LENGTH: 19
<212> TYPE: DNA
<213> ORGANISM: Artificial
<220> FEATURE:
<223> OTHER INFORMATION: SNP probe sequence

<400> SEQUENCE: 151
cagagatcca gcaaataaa                                                19

<210> SEQ ID NO 152
<211> LENGTH: 16
<212> TYPE: DNA
<213> ORGANISM: Artificial
<220> FEATURE:
<223> OTHER INFORMATION: SNP probe sequence

<400> SEQUENCE: 152
agagtgttct gtgcgg                                                   16

<210> SEQ ID NO 153
<211> LENGTH: 15
<212> TYPE: DNA
<213> ORGANISM: Artificial
<220> FEATURE:
<223> OTHER INFORMATION: SNP probe sequence

<400> SEQUENCE: 153
cagacgcttc gatgt                                                    15

<210> SEQ ID NO 154
<211> LENGTH: 19
<212> TYPE: DNA
<213> ORGANISM: Artificial
<220> FEATURE:
<223> OTHER INFORMATION: SNP probe sequence

<400> SEQUENCE: 154
tagtacccat aataatgat                                                19
```

<210> SEQ ID NO 155
<211> LENGTH: 18
<212> TYPE: DNA
<213> ORGANISM: Artificial
<220> FEATURE:
<223> OTHER INFORMATION: SNP probe sequence

<400> SEQUENCE: 155
acaagtgtta ctcgatgc                                                 18

<210> SEQ ID NO 156
<211> LENGTH: 16
<212> TYPE: DNA
<213> ORGANISM: Artificial
<220> FEATURE:
<223> OTHER INFORMATION: SNP probe sequence

<400> SEQUENCE: 156
tgaactagca cccttt                                                   16

<210> SEQ ID NO 157
<211> LENGTH: 17
<212> TYPE: DNA
<213> ORGANISM: Artificial
<220> FEATURE:
<223> OTHER INFORMATION: SNP probe sequence

<400> SEQUENCE: 157
ttgcagtatc atacaac                                                  17

<210> SEQ ID NO 158
<211> LENGTH: 14
<212> TYPE: DNA
<213> ORGANISM: Artificial
<220> FEATURE:
<223> OTHER INFORMATION: SNP probe sequence

<400> SEQUENCE: 158
aacggctgga ccac                                                     14

<210> SEQ ID NO 159
<211> LENGTH: 20
<212> TYPE: DNA
<213> ORGANISM: Artificial
<220> FEATURE:
<223> OTHER INFORMATION: SNP probe sequence

<400> SEQUENCE: 159
agtggtatat gcagtcattg                                               20

<210> SEQ ID NO 160
<211> LENGTH: 20
<212> TYPE: DNA
<213> ORGANISM: Artificial
<220> FEATURE:
<223> OTHER INFORMATION: SNP probe sequence

<400> SEQUENCE: 160
atgtttcaac ttttcttcct                                               20

<210> SEQ ID NO 161
<211> LENGTH: 14
<212> TYPE: DNA
<213> ORGANISM: Artificial
<220> FEATURE:

<223> OTHER INFORMATION: SNP probe sequence

<400> SEQUENCE: 161
cacaaagccc ctgt                                                14

<210> SEQ ID NO 162
<211> LENGTH: 20
<212> TYPE: DNA
<213> ORGANISM: Artificial
<220> FEATURE:
<223> OTHER INFORMATION: SNP probe sequence

<400> SEQUENCE: 162
aactaactgt gatattgacg                                          20

<210> SEQ ID NO 163
<211> LENGTH: 13
<212> TYPE: DNA
<213> ORGANISM: Artificial
<220> FEATURE:
<223> OTHER INFORMATION: SNP probe sequence

<400> SEQUENCE: 163
ccgtccgcgg tgt                                                 13

<210> SEQ ID NO 164
<211> LENGTH: 19
<212> TYPE: DNA
<213> ORGANISM: Artificial
<220> FEATURE:
<223> OTHER INFORMATION: SNP probe sequence

<400> SEQUENCE: 164
cctatgaata acagcacta                                           19

<210> SEQ ID NO 165
<211> LENGTH: 15
<212> TYPE: DNA
<213> ORGANISM: Artificial
<220> FEATURE:
<223> OTHER INFORMATION: SNP probe sequence

<400> SEQUENCE: 165
tagtggcgac aacgt                                               15

<210> SEQ ID NO 166
<211> LENGTH: 17
<212> TYPE: DNA
<213> ORGANISM: Artificial
<220> FEATURE:
<223> OTHER INFORMATION: SNP probe sequence

<400> SEQUENCE: 166
taaagcctcc agaagtg                                             17

<210> SEQ ID NO 167
<211> LENGTH: 17
<212> TYPE: DNA
<213> ORGANISM: Artificial
<220> FEATURE:
<223> OTHER INFORMATION: SNP probe sequence

<400> SEQUENCE: 167
tccttgtgga gaaactg                                             17

```
<210> SEQ ID NO 168
<211> LENGTH: 16
<212> TYPE: DNA
<213> ORGANISM: Artificial
<220> FEATURE:
<223> OTHER INFORMATION: SNP probe sequence

<400> SEQUENCE: 168
tttcctgagc ctgaag                                                    16

<210> SEQ ID NO 169
<211> LENGTH: 16
<212> TYPE: DNA
<213> ORGANISM: Artificial
<220> FEATURE:
<223> OTHER INFORMATION: SNP probe sequence

<400> SEQUENCE: 169
tgttctccct cgaaag                                                    16

<210> SEQ ID NO 170
<211> LENGTH: 16
<212> TYPE: DNA
<213> ORGANISM: Artificial
<220> FEATURE:
<223> OTHER INFORMATION: SNP probe sequence

<400> SEQUENCE: 170
cagcgataac tgcttc                                                    16

<210> SEQ ID NO 171
<211> LENGTH: 15
<212> TYPE: DNA
<213> ORGANISM: Artificial
<220> FEATURE:
<223> OTHER INFORMATION: SNP probe sequence

<400> SEQUENCE: 171
tgtgttgtcg gtgtg                                                     15

<210> SEQ ID NO 172
<211> LENGTH: 14
<212> TYPE: DNA
<213> ORGANISM: Artificial
<220> FEATURE:
<223> OTHER INFORMATION: SNP probe sequence

<400> SEQUENCE: 172
cgcgagcaaa acgt                                                      14

<210> SEQ ID NO 173
<211> LENGTH: 18
<212> TYPE: DNA
<213> ORGANISM: Artificial
<220> FEATURE:
<223> OTHER INFORMATION: SNP probe sequence

<400> SEQUENCE: 173
ctgttagtct tctccaaa                                                  18

<210> SEQ ID NO 174
<211> LENGTH: 18
<212> TYPE: DNA
<213> ORGANISM: Artificial
<220> FEATURE:
<223> OTHER INFORMATION: SNP probe sequence
```

<400> SEQUENCE: 174
atggcgggaa tgttcatg                                                   18

<210> SEQ ID NO 175
<211> LENGTH: 19
<212> TYPE: DNA
<213> ORGANISM: Artificial
<220> FEATURE:
<223> OTHER INFORMATION: SNP probe sequence

<400> SEQUENCE: 175
tgtgatgtgg aaaaacacg                                                  19

<210> SEQ ID NO 176
<211> LENGTH: 17
<212> TYPE: DNA
<213> ORGANISM: Artificial
<220> FEATURE:
<223> OTHER INFORMATION: SNP probe sequence

<400> SEQUENCE: 176
aagactctgc taaagca                                                    17

<210> SEQ ID NO 177
<211> LENGTH: 16
<212> TYPE: DNA
<213> ORGANISM: Artificial
<220> FEATURE:
<223> OTHER INFORMATION: SNP probe sequence

<400> SEQUENCE: 177
tacgaagacc tagcta                                                     16

<210> SEQ ID NO 178
<211> LENGTH: 15
<212> TYPE: DNA
<213> ORGANISM: Artificial
<220> FEATURE:
<223> OTHER INFORMATION: SNP probe sequence

<400> SEQUENCE: 178
atgcgtccgt gtctc                                                      15

<210> SEQ ID NO 179
<211> LENGTH: 18
<212> TYPE: DNA
<213> ORGANISM: Artificial
<220> FEATURE:
<223> OTHER INFORMATION: SNP probe sequence

<400> SEQUENCE: 179
atgcaattaa ctctgcca                                                   18

<210> SEQ ID NO 180
<211> LENGTH: 19
<212> TYPE: DNA
<213> ORGANISM: Artificial
<220> FEATURE:
<223> OTHER INFORMATION: SNP probe sequence

<400> SEQUENCE: 180
ctcaatgacg acgataaat                                                  19

<210> SEQ ID NO 181
<211> LENGTH: 16

```
<212> TYPE: DNA
<213> ORGANISM: Artificial
<220> FEATURE:
<223> OTHER INFORMATION: SNP probe sequence

<400> SEQUENCE: 181
caagttcttc cacaga                                                  16

<210> SEQ ID NO 182
<211> LENGTH: 22
<212> TYPE: DNA
<213> ORGANISM: Artificial
<220> FEATURE:
<223> OTHER INFORMATION: SNP probe sequence

<400> SEQUENCE: 182
aggaagaaca attacataga ta                                           22

<210> SEQ ID NO 183
<211> LENGTH: 15
<212> TYPE: DNA
<213> ORGANISM: Artificial
<220> FEATURE:
<223> OTHER INFORMATION: SNP probe sequence

<400> SEQUENCE: 183
ctatgtcccg tacga                                                   15

<210> SEQ ID NO 184
<211> LENGTH: 17
<212> TYPE: DNA
<213> ORGANISM: Artificial
<220> FEATURE:
<223> OTHER INFORMATION: SNP probe sequence

<400> SEQUENCE: 184
catcatctcc taaacga                                                 17

<210> SEQ ID NO 185
<211> LENGTH: 14
<212> TYPE: DNA
<213> ORGANISM: Artificial
<220> FEATURE:
<223> OTHER INFORMATION: SNP probe sequence

<400> SEQUENCE: 185
agcggcggca gaga                                                    14

<210> SEQ ID NO 186
<211> LENGTH: 18
<212> TYPE: DNA
<213> ORGANISM: Artificial
<220> FEATURE:
<223> OTHER INFORMATION: SNP probe sequence

<400> SEQUENCE: 186
ctgtagcttc tactcaag                                                18

<210> SEQ ID NO 187
<211> LENGTH: 20
<212> TYPE: DNA
<213> ORGANISM: Artificial
<220> FEATURE:
<223> OTHER INFORMATION: SNP probe sequence

<400> SEQUENCE: 187
```

```
aggattctta ggtgttgtac                                              20

<210> SEQ ID NO 188
<211> LENGTH: 19
<212> TYPE: DNA
<213> ORGANISM: Artificial
<220> FEATURE:
<223> OTHER INFORMATION: SNP probe sequence

<400> SEQUENCE: 188
tgaaccactt aaaagttga                                               19

<210> SEQ ID NO 189
<211> LENGTH: 18
<212> TYPE: DNA
<213> ORGANISM: Artificial
<220> FEATURE:
<223> OTHER INFORMATION: SNP probe sequence

<400> SEQUENCE: 189
tcattgagaa atccgttt                                                18

<210> SEQ ID NO 190
<211> LENGTH: 20
<212> TYPE: DNA
<213> ORGANISM: Artificial
<220> FEATURE:
<223> OTHER INFORMATION: SNP probe sequence

<400> SEQUENCE: 190
tagtttactc tccgttgtct                                              20

<210> SEQ ID NO 191
<211> LENGTH: 20
<212> TYPE: DNA
<213> ORGANISM: Artificial
<220> FEATURE:
<223> OTHER INFORMATION: SNP probe sequence

<400> SEQUENCE: 191
acttcatatt cagcaatatt                                              20

<210> SEQ ID NO 192
<211> LENGTH: 19
<212> TYPE: DNA
<213> ORGANISM: Artificial
<220> FEATURE:
<223> OTHER INFORMATION: SNP probe sequence

<400> SEQUENCE: 192
ccagtcacaa tcaagatta                                               19

<210> SEQ ID NO 193
<211> LENGTH: 14
<212> TYPE: DNA
<213> ORGANISM: Artificial
<220> FEATURE:
<223> OTHER INFORMATION: SNP probe sequence

<400> SEQUENCE: 193
tcaccgccag tatg                                                    14

<210> SEQ ID NO 194
<211> LENGTH: 18
<212> TYPE: DNA
<213> ORGANISM: Artificial
```

```
<220> FEATURE:
<223> OTHER INFORMATION: SNP probe sequence

<400> SEQUENCE: 194
tgtgttgggt tttattga                                              18

<210> SEQ ID NO 195
<211> LENGTH: 15
<212> TYPE: DNA
<213> ORGANISM: Artificial
<220> FEATURE:
<223> OTHER INFORMATION: SNP probe sequence

<400> SEQUENCE: 195
ccaaggcggt aacca                                                 15

<210> SEQ ID NO 196
<211> LENGTH: 15
<212> TYPE: DNA
<213> ORGANISM: Artificial
<220> FEATURE:
<223> OTHER INFORMATION: SNP probe sequence

<400> SEQUENCE: 196
actgaccctc aaccc                                                 15

<210> SEQ ID NO 197
<211> LENGTH: 17
<212> TYPE: DNA
<213> ORGANISM: Artificial
<220> FEATURE:
<223> OTHER INFORMATION: SNP probe sequence

<400> SEQUENCE: 197
ttcctatgtg tatcagg                                               17

<210> SEQ ID NO 198
<211> LENGTH: 17
<212> TYPE: DNA
<213> ORGANISM: Artificial
<220> FEATURE:
<223> OTHER INFORMATION: SNP probe sequence

<400> SEQUENCE: 198
aacaacaacg tgcaagt                                               17

<210> SEQ ID NO 199
<211> LENGTH: 18
<212> TYPE: DNA
<213> ORGANISM: Artificial
<220> FEATURE:
<223> OTHER INFORMATION: SNP probe sequence

<400> SEQUENCE: 199
cactcttttg agacatca                                              18

<210> SEQ ID NO 200
<211> LENGTH: 16
<212> TYPE: DNA
<213> ORGANISM: Artificial
<220> FEATURE:
<223> OTHER INFORMATION: SNP probe sequence

<400> SEQUENCE: 200
cctgccgtat gataca                                                16
```

<210> SEQ ID NO 201
<211> LENGTH: 16
<212> TYPE: DNA
<213> ORGANISM: Artificial
<220> FEATURE:
<223> OTHER INFORMATION: SNP probe sequence

<400> SEQUENCE: 201
ttgtttgcat gtgaca                                                   16

<210> SEQ ID NO 202
<211> LENGTH: 17
<212> TYPE: DNA
<213> ORGANISM: Artificial
<220> FEATURE:
<223> OTHER INFORMATION: SNP probe sequence

<400> SEQUENCE: 202
cttgggtacg aggaaag                                                  17

<210> SEQ ID NO 203
<211> LENGTH: 18
<212> TYPE: DNA
<213> ORGANISM: Artificial
<220> FEATURE:
<223> OTHER INFORMATION: SNP probe sequence

<400> SEQUENCE: 203
ctgtaatttc tcacaata                                                 18

<210> SEQ ID NO 204
<211> LENGTH: 19
<212> TYPE: DNA
<213> ORGANISM: Artificial
<220> FEATURE:
<223> OTHER INFORMATION: SNP probe sequence

<400> SEQUENCE: 204
aggtgttgaa atggacagc                                                19

<210> SEQ ID NO 205
<211> LENGTH: 18
<212> TYPE: DNA
<213> ORGANISM: Artificial
<220> FEATURE:
<223> OTHER INFORMATION: SNP probe sequence

<400> SEQUENCE: 205
tgaagagctg acacattt                                                 18

<210> SEQ ID NO 206
<211> LENGTH: 15
<212> TYPE: DNA
<213> ORGANISM: Artificial
<220> FEATURE:
<223> OTHER INFORMATION: SNP probe sequence

<400> SEQUENCE: 206
cgaaattgcc ctcga                                                    15

<210> SEQ ID NO 207
<211> LENGTH: 17
<212> TYPE: DNA
<213> ORGANISM: Artificial
<220> FEATURE:
<223> OTHER INFORMATION: SNP probe sequence

<400> SEQUENCE: 207 cctttagta aaaaatg                                                17

<210> SEQ ID NO 208
<211> LENGTH: 18
<212> TYPE: DNA
<213> ORGANISM: Artificial
<220> FEATURE:
<223> OTHER INFORMATION: SNP probe sequence

<400> SEQUENCE: 208
catgtctggt atagtttt                                              18

<210> SEQ ID NO 209
<211> LENGTH: 19
<212> TYPE: DNA
<213> ORGANISM: Artificial
<220> FEATURE:
<223> OTHER INFORMATION: SNP probe sequence

<400> SEQUENCE: 209
tcattgccct tttagtaaa                                             19

<210> SEQ ID NO 210
<211> LENGTH: 19
<212> TYPE: DNA
<213> ORGANISM: Artificial
<220> FEATURE:
<223> OTHER INFORMATION: SNP probe sequence

<400> SEQUENCE: 210
caatgttcaa actgaagga                                             19

<210> SEQ ID NO 211
<211> LENGTH: 17
<212> TYPE: DNA
<213> ORGANISM: Artificial
<220> FEATURE:
<223> OTHER INFORMATION: SNP probe sequence

<400> SEQUENCE: 211
ttctactctt agcaaca                                               17

<210> SEQ ID NO 212
<211> LENGTH: 16
<212> TYPE: DNA
<213> ORGANISM: Artificial
<220> FEATURE:
<223> OTHER INFORMATION: SNP probe sequence

<400> SEQUENCE: 212
ttgcagcacc aaaatc                                                16

<210> SEQ ID NO 213
<211> LENGTH: 17
<212> TYPE: DNA
<213> ORGANISM: Artificial
<220> FEATURE:
<223> OTHER INFORMATION: SNP probe sequence

<400> SEQUENCE: 213
tgttgctctc tgatgat                                               17

<210> SEQ ID NO 214

```
<211> LENGTH: 19
<212> TYPE: DNA
<213> ORGANISM: Artificial
<220> FEATURE:
<223> OTHER INFORMATION: SNP probe sequence

<400> SEQUENCE: 214
caatgttcaa actgaagga                                                      19

<210> SEQ ID NO 215
<211> LENGTH: 15
<212> TYPE: DNA
<213> ORGANISM: Artificial
<220> FEATURE:
<223> OTHER INFORMATION: SNP probe sequence

<400> SEQUENCE: 215
tcaactccga aacgg                                                          15

<210> SEQ ID NO 216
<211> LENGTH: 16
<212> TYPE: DNA
<213> ORGANISM: Artificial
<220> FEATURE:
<223> OTHER INFORMATION: SNP probe sequence

<400> SEQUENCE: 216
cacatgcatg tttaag                                                         16

<210> SEQ ID NO 217
<211> LENGTH: 18
<212> TYPE: DNA
<213> ORGANISM: Artificial
<220> FEATURE:
<223> OTHER INFORMATION: SNP probe sequence

<400> SEQUENCE: 217
tcatcatcaa cctcaacc                                                       18

<210> SEQ ID NO 218
<211> LENGTH: 18
<212> TYPE: DNA
<213> ORGANISM: Artificial
<220> FEATURE:
<223> OTHER INFORMATION: SNP probe sequence

<400> SEQUENCE: 218
ccatattctc aagataag                                                       18

<210> SEQ ID NO 219
<211> LENGTH: 16
<212> TYPE: DNA
<213> ORGANISM: Artificial
<220> FEATURE:
<223> OTHER INFORMATION: SNP probe sequence

<400> SEQUENCE: 219
tacaagctgc tcatga                                                         16

<210> SEQ ID NO 220
<211> LENGTH: 19
<212> TYPE: DNA
<213> ORGANISM: Artificial
<220> FEATURE:
<223> OTHER INFORMATION: SNP probe sequence

<400> SEQUENCE: 220
```

-continued

```
ttatgtcatt tgtgatggt                                          19

<210> SEQ ID NO 221
<211> LENGTH: 18
<212> TYPE: DNA
<213> ORGANISM: Artificial
<220> FEATURE:
<223> OTHER INFORMATION: SNP probe sequence

<400> SEQUENCE: 221
atgggaacct ctatcgta                                           18

<210> SEQ ID NO 222
<211> LENGTH: 17
<212> TYPE: DNA
<213> ORGANISM: Artificial
<220> FEATURE:
<223> OTHER INFORMATION: SNP probe sequence

<400> SEQUENCE: 222
actgttccag ctcttaa                                            17

<210> SEQ ID NO 223
<211> LENGTH: 18
<212> TYPE: DNA
<213> ORGANISM: Artificial
<220> FEATURE:
<223> OTHER INFORMATION: SNP probe sequence

<400> SEQUENCE: 223
tgacatgatg ctttgttg                                           18

<210> SEQ ID NO 224
<211> LENGTH: 18
<212> TYPE: DNA
<213> ORGANISM: Artificial
<220> FEATURE:
<223> OTHER INFORMATION: SNP probe sequence

<400> SEQUENCE: 224
tataccgtct atactaac                                           18

<210> SEQ ID NO 225
<211> LENGTH: 17
<212> TYPE: DNA
<213> ORGANISM: Artificial
<220> FEATURE:
<223> OTHER INFORMATION: SNP probe sequence

<400> SEQUENCE: 225
catcatgttc aggaacc                                            17

<210> SEQ ID NO 226
<211> LENGTH: 17
<212> TYPE: DNA
<213> ORGANISM: Artificial
<220> FEATURE:
<223> OTHER INFORMATION: SNP probe sequence

<400> SEQUENCE: 226
catgggagtc atgtttc                                            17

<210> SEQ ID NO 227
<211> LENGTH: 16
<212> TYPE: DNA
```

```
<213> ORGANISM: Artificial
<220> FEATURE:
<223> OTHER INFORMATION: SNP probe sequence

<400> SEQUENCE: 227
cacccagaaa caatcc                                                        16

<210> SEQ ID NO 228
<211> LENGTH: 18
<212> TYPE: DNA
<213> ORGANISM: Artificial
<220> FEATURE:
<223> OTHER INFORMATION: SNP probe sequence

<400> SEQUENCE: 228
aaagcaactt ccgtgatt                                                      18

<210> SEQ ID NO 229
<211> LENGTH: 16
<212> TYPE: DNA
<213> ORGANISM: Artificial
<220> FEATURE:
<223> OTHER INFORMATION: SNP probe sequence

<400> SEQUENCE: 229
cccatcagag aacaca                                                        16

<210> SEQ ID NO 230
<211> LENGTH: 16
<212> TYPE: DNA
<213> ORGANISM: Artificial
<220> FEATURE:
<223> OTHER INFORMATION: SNP probe sequence

<400> SEQUENCE: 230
aagccagcct tagtat                                                        16

<210> SEQ ID NO 231
<211> LENGTH: 14
<212> TYPE: DNA
<213> ORGANISM: Artificial
<220> FEATURE:
<223> OTHER INFORMATION: SNP probe sequence

<400> SEQUENCE: 231
accacgaacg cgaa                                                          14

<210> SEQ ID NO 232
<211> LENGTH: 16
<212> TYPE: DNA
<213> ORGANISM: Artificial
<220> FEATURE:
<223> OTHER INFORMATION: SNP probe sequence

<400> SEQUENCE: 232
atctgaggcc ttggtg                                                        16

<210> SEQ ID NO 233
<211> LENGTH: 17
<212> TYPE: DNA
<213> ORGANISM: Artificial
<220> FEATURE:
<223> OTHER INFORMATION: SNP probe sequence

<400> SEQUENCE: 233
tccagcaaat gaaaggg                                                       17
```

```
<210> SEQ ID NO 234
<211> LENGTH: 17
<212> TYPE: DNA
<213> ORGANISM: Artificial
<220> FEATURE:
<223> OTHER INFORMATION: SNP probe sequence

<400> SEQUENCE: 234
cagagtgttc tgtgtgg                                                  17

<210> SEQ ID NO 235
<211> LENGTH: 16
<212> TYPE: DNA
<213> ORGANISM: Artificial
<220> FEATURE:
<223> OTHER INFORMATION: SNP probe sequence

<400> SEQUENCE: 235
agacgcttcg gtgtaa                                                   16

<210> SEQ ID NO 236
<211> LENGTH: 17
<212> TYPE: DNA
<213> ORGANISM: Artificial
<220> FEATURE:
<223> OTHER INFORMATION: SNP probe sequence

<400> SEQUENCE: 236
ttttagtacc catgata                                                  17

<210> SEQ ID NO 237
<211> LENGTH: 18
<212> TYPE: DNA
<213> ORGANISM: Artificial
<220> FEATURE:
<223> OTHER INFORMATION: SNP probe sequence

<400> SEQUENCE: 237
caagtgttac tctatgca                                                 18

<210> SEQ ID NO 238
<211> LENGTH: 17
<212> TYPE: DNA
<213> ORGANISM: Artificial
<220> FEATURE:
<223> OTHER INFORMATION: SNP probe sequence

<400> SEQUENCE: 238
catgaactag caccttt                                                  17

<210> SEQ ID NO 239
<211> LENGTH: 16
<212> TYPE: DNA
<213> ORGANISM: Artificial
<220> FEATURE:
<223> OTHER INFORMATION: SNP probe sequence

<400> SEQUENCE: 239
tttgcagtat catgca                                                   16

<210> SEQ ID NO 240
<211> LENGTH: 15
<212> TYPE: DNA
<213> ORGANISM: Artificial
<220> FEATURE:
```

<223> OTHER INFORMATION: SNP probe sequence

<400> SEQUENCE: 240
aacggctgga tcacc                                                        15

<210> SEQ ID NO 241
<211> LENGTH: 19
<212> TYPE: DNA
<213> ORGANISM: Artificial
<220> FEATURE:
<223> OTHER INFORMATION: SNP probe sequence

<400> SEQUENCE: 241
cagtggtata tgcagtgat                                                    19

<210> SEQ ID NO 242
<211> LENGTH: 21
<212> TYPE: DNA
<213> ORGANISM: Artificial
<220> FEATURE:
<223> OTHER INFORMATION: SNP probe sequence

<400> SEQUENCE: 242
aatgtttcaa cttttctttc t                                                 21

<210> SEQ ID NO 243
<211> LENGTH: 15
<212> TYPE: DNA
<213> ORGANISM: Artificial
<220> FEATURE:
<223> OTHER INFORMATION: SNP probe sequence

<400> SEQUENCE: 243
ttcacaaagt ccctg                                                        15

<210> SEQ ID NO 244
<211> LENGTH: 19
<212> TYPE: DNA
<213> ORGANISM: Artificial
<220> FEATURE:
<223> OTHER INFORMATION: SNP probe sequence

<400> SEQUENCE: 244
aactaactgt gatgttgac                                                    19

<210> SEQ ID NO 245
<211> LENGTH: 14
<212> TYPE: DNA
<213> ORGANISM: Artificial
<220> FEATURE:
<223> OTHER INFORMATION: SNP probe sequence

<400> SEQUENCE: 245
atttcgccgt cggc                                                         14

<210> SEQ ID NO 246
<211> LENGTH: 19
<212> TYPE: DNA
<213> ORGANISM: Artificial
<220> FEATURE:
<223> OTHER INFORMATION: SNP probe sequence

<400> SEQUENCE: 246
cctatgaata acagctcta                                                    19

```
<210> SEQ ID NO 247
<211> LENGTH: 16
<212> TYPE: DNA
<213> ORGANISM: Artificial
<220> FEATURE:
<223> OTHER INFORMATION: SNP probe sequence

<400> SEQUENCE: 247
tagtggcgac aatgtg                                                  16

<210> SEQ ID NO 248
<211> LENGTH: 16
<212> TYPE: DNA
<213> ORGANISM: Artificial
<220> FEATURE:
<223> OTHER INFORMATION: SNP probe sequence

<400> SEQUENCE: 248
taaagcctcc agaggt                                                  16

<210> SEQ ID NO 249
<211> LENGTH: 17
<212> TYPE: DNA
<213> ORGANISM: Artificial
<220> FEATURE:
<223> OTHER INFORMATION: SNP probe sequence

<400> SEQUENCE: 249
atccttgtgg agaagct                                                 17

<210> SEQ ID NO 250
<211> LENGTH: 16
<212> TYPE: DNA
<213> ORGANISM: Artificial
<220> FEATURE:
<223> OTHER INFORMATION: SNP probe sequence

<400> SEQUENCE: 250
ttttcctgag ccttaa                                                  16

<210> SEQ ID NO 251
<211> LENGTH: 15
<212> TYPE: DNA
<213> ORGANISM: Artificial
<220> FEATURE:
<223> OTHER INFORMATION: SNP probe sequence

<400> SEQUENCE: 251
tctcccttga aagca                                                   15

<210> SEQ ID NO 252
<211> LENGTH: 17
<212> TYPE: DNA
<213> ORGANISM: Artificial
<220> FEATURE:
<223> OTHER INFORMATION: SNP probe sequence

<400> SEQUENCE: 252
cagcgataac tgtttcc                                                 17

<210> SEQ ID NO 253
<211> LENGTH: 16
<212> TYPE: DNA
<213> ORGANISM: Artificial
<220> FEATURE:
<223> OTHER INFORMATION: SNP probe sequence
```

```
<400> SEQUENCE: 253
tgtgttgttg gtgtga                                                    16

<210> SEQ ID NO 254
<211> LENGTH: 14
<212> TYPE: DNA
<213> ORGANISM: Artificial
<220> FEATURE:
<223> OTHER INFORMATION: SNP probe sequence

<400> SEQUENCE: 254
cgaagcgcga tcaa                                                      14

<210> SEQ ID NO 255
<211> LENGTH: 17
<212> TYPE: DNA
<213> ORGANISM: Artificial
<220> FEATURE:
<223> OTHER INFORMATION: SNP probe sequence

<400> SEQUENCE: 255
tgttagtctt ctccgaa                                                   17

<210> SEQ ID NO 256
<211> LENGTH: 16
<212> TYPE: DNA
<213> ORGANISM: Artificial
<220> FEATURE:
<223> OTHER INFORMATION: SNP probe sequence

<400> SEQUENCE: 256
cgggaatgtt cgtgag                                                    16

<210> SEQ ID NO 257
<211> LENGTH: 18
<212> TYPE: DNA
<213> ORGANISM: Artificial
<220> FEATURE:
<223> OTHER INFORMATION: SNP probe sequence

<400> SEQUENCE: 257
tgatgtggaa aaactcga                                                  18

<210> SEQ ID NO 258
<211> LENGTH: 16
<212> TYPE: DNA
<213> ORGANISM: Artificial
<220> FEATURE:
<223> OTHER INFORMATION: SNP probe sequence

<400> SEQUENCE: 258
tgaagactct gctgaa                                                    16

<210> SEQ ID NO 259
<211> LENGTH: 17
<212> TYPE: DNA
<213> ORGANISM: Artificial
<220> FEATURE:
<223> OTHER INFORMATION: SNP probe sequence

<400> SEQUENCE: 259
tacacgtacg aagagct                                                   17

<210> SEQ ID NO 260
<211> LENGTH: 17
```

```
<212> TYPE: DNA
<213> ORGANISM: Artificial
<220> FEATURE:
<223> OTHER INFORMATION: SNP probe sequence

<400> SEQUENCE: 260
aatgcgtcct tgtctct                                               17

<210> SEQ ID NO 261
<211> LENGTH: 18
<212> TYPE: DNA
<213> ORGANISM: Artificial
<220> FEATURE:
<223> OTHER INFORMATION: SNP probe sequence

<400> SEQUENCE: 261
catgcaatta actcttcc                                              18

<210> SEQ ID NO 262
<211> LENGTH: 20
<212> TYPE: DNA
<213> ORGANISM: Artificial
<220> FEATURE:
<223> OTHER INFORMATION: SNP probe sequence

<400> SEQUENCE: 262
tcaatgacga cgattaatag                                            20

<210> SEQ ID NO 263
<211> LENGTH: 17
<212> TYPE: DNA
<213> ORGANISM: Artificial
<220> FEATURE:
<223> OTHER INFORMATION: SNP probe sequence

<400> SEQUENCE: 263
ccaagttctt ctacaga                                               17

<210> SEQ ID NO 264
<211> LENGTH: 21
<212> TYPE: DNA
<213> ORGANISM: Artificial
<220> FEATURE:
<223> OTHER INFORMATION: SNP probe sequence

<400> SEQUENCE: 264
aagaacaatt acataggtaa a                                          21

<210> SEQ ID NO 265
<211> LENGTH: 15
<212> TYPE: DNA
<213> ORGANISM: Artificial
<220> FEATURE:
<223> OTHER INFORMATION: SNP probe sequence

<400> SEQUENCE: 265
tatgtcccgt tcgat                                                 15

<210> SEQ ID NO 266
<211> LENGTH: 16
<212> TYPE: DNA
<213> ORGANISM: Artificial
<220> FEATURE:
<223> OTHER INFORMATION: SNP probe sequence

<400> SEQUENCE: 266
```
catcatctcc tagacg								16

<210> SEQ ID NO 267
<211> LENGTH: 13
<212> TYPE: DNA
<213> ORGANISM: Artificial
<220> FEATURE:
<223> OTHER INFORMATION: SNP probe sequence

<400> SEQUENCE: 267
cggcggcgga gag								13

<210> SEQ ID NO 268
<211> LENGTH: 16
<212> TYPE: DNA
<213> ORGANISM: Artificial
<220> FEATURE:
<223> OTHER INFORMATION: SNP probe sequence

<400> SEQUENCE: 268
tgtagcttct acccaa								16

<210> SEQ ID NO 269
<211> LENGTH: 20
<212> TYPE: DNA
<213> ORGANISM: Artificial
<220> FEATURE:
<223> OTHER INFORMATION: SNP probe sequence

<400> SEQUENCE: 269
aggattctta ggtgttctac								20

<210> SEQ ID NO 270
<211> LENGTH: 20
<212> TYPE: DNA
<213> ORGANISM: Artificial
<220> FEATURE:
<223> OTHER INFORMATION: SNP probe sequence

<400> SEQUENCE: 270
catgaaccac ttaaaaattg								20

<210> SEQ ID NO 271
<211> LENGTH: 18
<212> TYPE: DNA
<213> ORGANISM: Artificial
<220> FEATURE:
<223> OTHER INFORMATION: SNP probe sequence

<400> SEQUENCE: 271
cattgagaaa tccatttc								18

<210> SEQ ID NO 272
<211> LENGTH: 23
<212> TYPE: DNA
<213> ORGANISM: Artificial
<220> FEATURE:
<223> OTHER INFORMATION: SNP probe sequence

<400> SEQUENCE: 272
ctctagttta ctctcctttg tct								23

<210> SEQ ID NO 273
<211> LENGTH: 19
<212> TYPE: DNA
<213> ORGANISM: Artificial

```
<220> FEATURE:
<223> OTHER INFORMATION: SNP probe sequence

<400> SEQUENCE: 273
cttcatattc agcaatgtt                                              19

<210> SEQ ID NO 274
<211> LENGTH: 19
<212> TYPE: DNA
<213> ORGANISM: Artificial
<220> FEATURE:
<223> OTHER INFORMATION: SNP probe sequence

<400> SEQUENCE: 274
cagtcacaat caagattgt                                              19

<210> SEQ ID NO 275
<211> LENGTH: 13
<212> TYPE: DNA
<213> ORGANISM: Artificial
<220> FEATURE:
<223> OTHER INFORMATION: SNP probe sequence

<400> SEQUENCE: 275
caccgccggt atg                                                    13

<210> SEQ ID NO 276
<211> LENGTH: 18
<212> TYPE: DNA
<213> ORGANISM: Artificial
<220> FEATURE:
<223> OTHER INFORMATION: SNP probe sequence

<400> SEQUENCE: 276
actgtgttgg gttttctt                                               18

<210> SEQ ID NO 277
<211> LENGTH: 15
<212> TYPE: DNA
<213> ORGANISM: Artificial
<220> FEATURE:
<223> OTHER INFORMATION: SNP probe sequence

<400> SEQUENCE: 277
accggccaag gtggt                                                  15

<210> SEQ ID NO 278
<211> LENGTH: 14
<212> TYPE: DNA
<213> ORGANISM: Artificial
<220> FEATURE:
<223> OTHER INFORMATION: SNP probe sequence

<400> SEQUENCE: 278
tgaccctcaa tccc                                                   14

<210> SEQ ID NO 279
<211> LENGTH: 17
<212> TYPE: DNA
<213> ORGANISM: Artificial
<220> FEATURE:
<223> OTHER INFORMATION: SNP probe sequence

<400> SEQUENCE: 279
tcctatgtgt atgagga                                                17
```

```
<210> SEQ ID NO 280
<211> LENGTH: 15
<212> TYPE: DNA
<213> ORGANISM: Artificial
<220> FEATURE:
<223> OTHER INFORMATION: SNP probe sequence

<400> SEQUENCE: 280
caacaacgtg cgagt                                                    15

<210> SEQ ID NO 281
<211> LENGTH: 17
<212> TYPE: DNA
<213> ORGANISM: Artificial
<220> FEATURE:
<223> OTHER INFORMATION: SNP probe sequence

<400> SEQUENCE: 281
cactcttttg agacgtc                                                  17

<210> SEQ ID NO 282
<211> LENGTH: 16
<212> TYPE: DNA
<213> ORGANISM: Artificial
<220> FEATURE:
<223> OTHER INFORMATION: SNP probe sequence

<400> SEQUENCE: 282
ctgccgtatg atccat                                                   16

<210> SEQ ID NO 283
<211> LENGTH: 15
<212> TYPE: DNA
<213> ORGANISM: Artificial
<220> FEATURE:
<223> OTHER INFORMATION: SNP probe sequence

<400> SEQUENCE: 283
tttgcatgtg gcaga                                                    15

<210> SEQ ID NO 284
<211> LENGTH: 17
<212> TYPE: DNA
<213> ORGANISM: Artificial
<220> FEATURE:
<223> OTHER INFORMATION: SNP probe sequence

<400> SEQUENCE: 284
cttgggtacg aggagag                                                  17

<210> SEQ ID NO 285
<211> LENGTH: 18
<212> TYPE: DNA
<213> ORGANISM: Artificial
<220> FEATURE:
<223> OTHER INFORMATION: SNP probe sequence

<400> SEQUENCE: 285
ctgtaatttc tcagaata                                                 18

<210> SEQ ID NO 286
<211> LENGTH: 16
<212> TYPE: DNA
<213> ORGANISM: Artificial
<220> FEATURE:
<223> OTHER INFORMATION: SNP probe sequence
```

```
<400> SEQUENCE: 286
tgttgaaatg gacggc                                                    16

<210> SEQ ID NO 287
<211> LENGTH: 15
<212> TYPE: DNA
<213> ORGANISM: Artificial
<220> FEATURE:
<223> OTHER INFORMATION: SNP probe sequence

<400> SEQUENCE: 287
tgaagagctg gcaca                                                     15

<210> SEQ ID NO 288
<211> LENGTH: 17
<212> TYPE: DNA
<213> ORGANISM: Artificial
<220> FEATURE:
<223> OTHER INFORMATION: SNP probe sequence

<400> SEQUENCE: 288
tgtgacgaaa ttgctct                                                   17

<210> SEQ ID NO 289
<211> LENGTH: 16
<212> TYPE: DNA
<213> ORGANISM: Artificial
<220> FEATURE:
<223> OTHER INFORMATION: SNP probe sequence

<400> SEQUENCE: 289
cttttagtga aaaatg                                                    16

<210> SEQ ID NO 290
<211> LENGTH: 17
<212> TYPE: DNA
<213> ORGANISM: Artificial
<220> FEATURE:
<223> OTHER INFORMATION: SNP probe sequence

<400> SEQUENCE: 290
atgtctggta gagtttt                                                   17

<210> SEQ ID NO 291
<211> LENGTH: 18
<212> TYPE: DNA
<213> ORGANISM: Artificial
<220> FEATURE:
<223> OTHER INFORMATION: SNP probe sequence

<400> SEQUENCE: 291
cattgccctt ttagtgaa                                                  18

<210> SEQ ID NO 292
<211> LENGTH: 19
<212> TYPE: DNA
<213> ORGANISM: Artificial
<220> FEATURE:
<223> OTHER INFORMATION: SNP probe sequence

<400> SEQUENCE: 292
caatgttcaa actgatgga                                                 19

<210> SEQ ID NO 293
```

```
<211> LENGTH: 16
<212> TYPE: DNA
<213> ORGANISM: Artificial
<220> FEATURE:
<223> OTHER INFORMATION: SNP probe sequence

<400> SEQUENCE: 293
tctactctta gcgaca                                                   16

<210> SEQ ID NO 294
<211> LENGTH: 15
<212> TYPE: DNA
<213> ORGANISM: Artificial
<220> FEATURE:
<223> OTHER INFORMATION: SNP probe sequence

<400> SEQUENCE: 294
tgcagcacca aagtc                                                    15

<210> SEQ ID NO 295
<211> LENGTH: 16
<212> TYPE: DNA
<213> ORGANISM: Artificial
<220> FEATURE:
<223> OTHER INFORMATION: SNP probe sequence

<400> SEQUENCE: 295
tgctctctga ttatgc                                                   16

<210> SEQ ID NO 296
<211> LENGTH: 19
<212> TYPE: DNA
<213> ORGANISM: Artificial
<220> FEATURE:
<223> OTHER INFORMATION: SNP probe sequence

<400> SEQUENCE: 296
caatgttcaa actgatgga                                                19

<210> SEQ ID NO 297
<211> LENGTH: 17
<212> TYPE: DNA
<213> ORGANISM: Artificial
<220> FEATURE:
<223> OTHER INFORMATION: SNP probe sequence

<400> SEQUENCE: 297
caactccgaa atggaac                                                  17

<210> SEQ ID NO 298
<211> LENGTH: 16
<212> TYPE: DNA
<213> ORGANISM: Artificial
<220> FEATURE:
<223> OTHER INFORMATION: SNP probe sequence

<400> SEQUENCE: 298
cacatgcatt tttaag                                                   16

<210> SEQ ID NO 299
<211> LENGTH: 18
<212> TYPE: DNA
<213> ORGANISM: Artificial
<220> FEATURE:
<223> OTHER INFORMATION: SNP probe sequence

<400> SEQUENCE: 299
```

```
tcatcatcaa gctcaacc                                                   18

<210> SEQ ID NO 300
<211> LENGTH: 18
<212> TYPE: DNA
<213> ORGANISM: Artificial
<220> FEATURE:
<223> OTHER INFORMATION: SNP probe sequence

<400> SEQUENCE: 300
ccatattctc tagataag                                                   18

<210> SEQ ID NO 301
<211> LENGTH: 14
<212> TYPE: DNA
<213> ORGANISM: Artificial
<220> FEATURE:
<223> OTHER INFORMATION: Chromosomal insertion sequence

<400> SEQUENCE: 301
cacacctagc taat                                                       14

<210> SEQ ID NO 302
<211> LENGTH: 647
<212> TYPE: DNA
<213> ORGANISM: Glycine max

<400> SEQUENCE: 302
agtacctcgc tctctgtctc atcatgctcg ctcgcggcgg cgccggcagt gtctccaccg     60
ccaaacccgc tgtctccgac aacaattctg cgccgctatc cgccgccaaa ctgagctaca    120
aatgttcggt ttgcaacaaa gccttctcct cttaccaagc actcggagga cacaaggcca    180
gccaccggaa gctcgccgga gaaaaccacc cgacctcctc cgcmgtgacg acgagttcgg    240
cgtcgaacgg tggtggtagg acccacgagt gctccatctg ccacaagacg ttttcgacag    300
gacaggcctt gggaggacac aaacgttgtc actacgaagg cggtaacagc gccgtaaccg    360
cctctgaggg agtggggtcc actcacacag gaagccaccg cgatttcgat ctcaacctcc    420
cggcttttcc ggacttctca gcaaggttct tcgtcgatga cgaggttacc agtcctcatc    480
catccaagaa gtcccgtttc aatttgacca tacccaagat tgaaatccct caatactgat    540
ccatagatcc aaaaaaatta ttcagtgttt ttttatatat ttttttaagt tatttgggat    600
taatttgttc ttgtacatat atagtacttg gaccttattc gctagtt                 647

<210> SEQ ID NO 303
<211> LENGTH: 326
<212> TYPE: DNA
<213> ORGANISM: Glycine max

<400> SEQUENCE: 303
gaagagaatg aattaaattc aaggcacaat cttataagcc ttggtcttgt ctatccaact     60
tatgaacgaa ttcttggagt tcctgaatcc caaaaaccca tgttccttgg ccttgttcat    120
gctatccaac attccctccc ctgagaaaat aagatccaca aaccaccaat cagcaacctc    180
gtcaagcttg gtaggcagaa gctgattctc actcacaatc tcatcccaaa caggaccctt    240
atccttcatc aattccgaca aactcaaacc ttcttcctca araagaatcg agaaggacg    300 aatagttgag gaccgaagtg gggacg                                         326

<210> SEQ ID NO 304
```

<211> LENGTH: 1082
<212> TYPE: DNA
<213> ORGANISM: Glycine max
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t

<400> SEQUENCE: 304

```
cgctctcgtg gagaaaagca ggtgtatttg ccctttaat aggtaaagta gagagttcat      60
catcataacc tgccaataac atgtctcatt aagaataatt aatggagaaa ggatgcagtg    120
tactgaagca atagggtga actgtactca cagttagatt ccctccaacc aagaatcatg    180
ttctcacggt caaagactat acggtaacca gtcatgaaat tttctgcatg aagataaata    240
caacgaatat ttcaggtatg natcaangca tcaacaataa ctgtggaagt ttaggtgttt    300
ttgtcatagt attgatgtgt gatttgttaa acttaaaaac agacaaacaa gacaggcatt    360
ggcgaatgct aaagaatttc agaagaaaca taagaaggtc taataagaat atagcagttg    420
tggctgctat attgataaga agcatgaatt gacaaagtaa tctgaaatga agcttcaag    480
atcatatata gtcagatata atttagtttt tnttcaatta aaatactcac gtcctatnat    540
nttcacgttg ttgctttca ggactcccaa acaaagtaag ttaatacct ggacattaca    600
agaaacattt atgaggttaa gagggctgaa atcattaga tattaatatt aaggaaaccc    660
aaagttggat tttatgttct cacctcacca ctgaccgtta ctatagggtc cgtgacaaga    720
taattgtctc cacctttcat agtcagatta atggaaagtt caacagtctg gttwggactg    780
caggtaaagt caaaatcagt gcgatggntt aaatttaaag gaaaagtag tagtagaggc    840
ttctctcaag ctataaatca ccttaattca taacagtact caaaggggag ctcattagaa    900
ctagaagntg aatgccgttg tagtttaatt tcttaattaa actncaaaaa taatggaaaa    960
aaattataaa ctcatgtcac atgaagctct agttaccttc ttaatcaact aaaatcaaga   1020
gggcttacac tgttagtaat ctgcttataa gctgctaaat gaggtatgtg aacgaggacc   1080
ag                                                                 1082
```

<210> SEQ ID NO 305
<211> LENGTH: 121

```
<212> TYPE: DNA
<213> ORGANISM: Glycine max
<220> FEATURE:
<221> NAME/KEY: misc_feature
<222> LOCATION: (69)..(69)
<223> OTHER INFORMATION: n is a, c, g, or t

<400> SEQUENCE: 305
atttctccat tgtatatatg tatacaagtc aagctcttca aaaccaccaa tgcgccaatg    60
mattcaaang tgaagcgtgg tcttaaaaat tcgcatttgc ttctggccag gtctctcgtg   120
g                                                                   121

<210> SEQ ID NO 306
<211> LENGTH: 1116
<212> TYPE: DNA
<213> ORGANISM: Glycine max
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t

<400> SEQUENCE: 306
caatatttgg ggaagaacgc tatggggaac ctttatcaga agatcagatt accctgcctg    60
ccattaagta ttctttaatt aaaagaagca atttaagatg ggaaacagaa gtgcgctggg   120
attgtcctca aaagttacca gaacaatggg gtatattatc gtgaaagcaa gataggtcca   180
ttctccgcag cagtttgaga attgccataa ttattactgt tatgccttgt catctggatg   240
tcacgtgaaa attgagtcct tgctttcgca tatggagctg cccttgctac aaatgaaaat   300
caatagtata aattttttcat tcaagataat cttcatttnt caatgcttag caaatttaac   360
tgtnggccat tcaccatttt tacnaattca acccaagttt gaagtgacaa gttccctcaa   420
attcaaattt cttttatcct gggaaactac tgttggaaaa catgraggct gtatagagag   480
agcaagggaa aaactcggaa tgcaagtatg caaggtggac cataaataac gcactacatt   540
actaacggtt ttaccaagga caatggttaa aaatcaaaag tgatttattt ttaattaant   600
```

```
gtganatatt actaatnttt ttttaccatg ttttctagaa gaagaaaaaa aaatatttat    660
tatttttttt atccattgcc tttagggcgg caaagatcag caaaacacat tagtatatta    720
ataattctcc tantcataaa aaaaatatna ctaattttcc taatgattcc acataaatgt    780
gtgtatttca aattctcaaa ataattgcta ctcaatgcga gcttatgttc agaagacttc    840
acaacataaa anaaatgccg gccttgtgcc cgtttatatt aatgttttta acataacgct    900
ggccttgtac cagcttatat taatgttttt aagtacaagt gcaatacaac tagtataaac    960
tcgacccaat gacattttac taagataact ataacccaca aattaacatt cttacctgta   1020
atttgctgaa cacagaggat attctgtcgc cttttccacc agcaaactga accaaaggga   1080
gaagtagaag agtaaaagaa gcacctaacc caatac                              1116

<210> SEQ ID NO 307
<211> LENGTH: 461
<212> TYPE: DNA
<213> ORGANISM: Glycine max

<400> SEQUENCE: 307
atggctgctt ctgagggaag gccattggtg gaggcagtgg aacacaagga ggatttctat     60
gagcaccaag agccaagtgg atgtgggtat ggatgctttc rgggttttgg gttgagttgg    120
tgtagaagcc atgaagaagg taaaggcctg gtggagcaga agggcaattc gtggctgagt    180
tgcaagttga ggaagataaa ggagttttca gaagtgattc caggccccaa gtggaaaaca    240
ttcatcagaa agataagcgg gtatggaagg aagcagcagc agaagaacag gtttcagtat    300
gatgaacaca gctatgctct caacttcaat agtggggata agagtgaaga tgatgacacg    360 cccccccagtt tctctgctag atttagtgct ccttttccct ctgctcgtcg ccaaactgaa    420
taatgatttg tgcatgctcg tttctgaaga ggtgttattg c                        461

<210> SEQ ID NO 308
<211> LENGTH: 639
<212> TYPE: DNA
<213> ORGANISM: Glycine max
<220> FEATURE:
<221> NAME/KEY: misc_feature
<222> LOCATION: (254)..(254)
<223> OTHER INFORMATION: n is a, c, g, or t

<400> SEQUENCE: 308
cattatgttt ttgttgtaag attggaatgc tttgctaact aattgttctg ttttcccccaa    60 gattccatgt cttagaatac ggattttcta attgttttag attctgggtt tatttttctca   120 tggtttcttg aatagtttag tttgtagaag tatggatatt tacccattta gtctgttgtg    180
ttaagtttat tactttgaac tattggttct tcatctgatt tggatttttgt aataatagga   240 cggagaacat ggcncgtaaa gctgctggag aagaaccttt gccagaggaa gatccttcaa    300
atcccatttt caagccgctc ccagagcctt cacggttgga gagcttcctc ataacaaatc    360
aaatttccaa ctactgcaac caaatcaatg ggtatgtgac taaggctctt ttttccatgt    420
ttgaggagca cgatacttaa gttrccaatt taaagtttct gattttcttc gttttcctat    480
atcatcatgg gtatctcttc tctagccaat agagtttaat tatccttaca ttttccgttg    540
catgttctgc agggtgtcag ggcagagctt taacagactc tatttgatga aggctttgca    600
tgaggattga taagccaatt tttgtttgtc attctgatg                           639

<210> SEQ ID NO 309
<211> LENGTH: 427
```

```
<212> TYPE: DNA
<213> ORGANISM: Glycine max

<400> SEQUENCE: 309
cagaacttct ggttgctaat cctgtggagc tgagtggaaa ggggagaccc cgtgtattct      60
atgatgttac gttgactta  aaagcgttgg gagtaggcat tttctcggta agttttatg     120 ttttaaagct tattgtgaca atgtttgatg ttctttaaag gaatctagta acagttctg     180 aataaaagct ctttcattgt tgtattgtag gctgaagttg ttagacattc aacacaagaa     240
cgtcaatggg aagtgtatag attttgttg  gaggaaagcc gtgactttcc attgaccaga     300
agccaagcaa gaactcagat tgttgacaaa gttagaagaa cactgatggg ctggtaatct     360
ggttcagtat caaatgaaaa rgcactttcc gttcagtttt tatgttaaat atcaatttgg     420
tttgccg                                                               427

<210> SEQ ID NO 310
<211> LENGTH: 501
<212> TYPE: DNA
<213> ORGANISM: Glycine max

<400> SEQUENCE: 310
cgccgccccc taccaccgcc caatgcccac gcgctaccag gaacccgacg atgatgagga      60
cgacaacgaa cccgacgatt tcgacgacga cgaagctgaa acggttacg  acgacgaaaa     120 caacatcgcc gcgtatcctc ggatcccgaa gaagcgcaag gtagtcggca ctgcagcggc     180
aggaggttct tacagttcg  cgccacgtgt caatttctcc tacggaaact cccgcggttc     240
gggttcgggc raggagtgga acgagcacga actttcgta  ctgttagaag tttggggaga     300
caagttcctc cagctcggga ggaacagttt gagatccgag aatggcacg  aggttgcaga     360 aaaagtttcc gaggaattga aaacagagag aacggtgaca cagtgtagaa gcgtgttgga     420
caagctgaaa agaaggtaca ggaaagagaa ggctagaatg gacgaaattg gccttggctc     480
ttgtaaatgg gccttcttca a                                               501

<210> SEQ ID NO 311
<211> LENGTH: 492
<212> TYPE: DNA
<213> ORGANISM: Glycine max
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t

<400> SEQUENCE: 311
aaattccaaa ccagttcaat cctttcagt  catctctttg gtcacgtttt cacagtaaca      60
taacatattc tgtggaaata tggcaaaact tggagactgt gcagctcatt tttttattgc     120
agcaatggtt ttgagcacgt tttacgtgac caaaactgtg gcacaatcag anattgcacc     180
cacatcgcaa atgagactg  gtgcagggtt tgctttgtct gtttctgggg tgaccttatg     240
ttcttctgtg ttggtttcta ttgtggcatt tatgatgcag tgaattgcaa ggcatattgg     300
ctcctattca tgtttgattg gtcttatcat gtacgtgntg aaattatatt ttatgatgaa     360 tttaagggt  tgttttttgtt tctttactat gcttgcttct tgaacacggt cctgtcgttt     420
ttggcattgt aacmtagtac tagctttatg atgagttaca tgtttgtaat tttcgccaag     480
```

```
<210> SEQ ID NO 312
<211> LENGTH: 375
<212> TYPE: DNA
<213> ORGANISM: Glycine max
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t

<400> SEQUENCE: 312
```

| | |
|---|---|
| tacctggcgt tcctgattca tggaacgaaa ttctttatgc acttcttctc aagcgggagg | 60 |
| atttttcga acggagacag catacaacaa aagtttctca agttccacta taattggtcn | 120 |
| atatacagtt tgcagagaat gttataagtt atacaaatct gtgacaaatc ttgctgaatg | 180 |
| aggtgaagct gcaagttgaa tgaggagaat agaaaattac atgacttta gtctcrtgaa | 240 |
| aagaagaaaa gggagaccaa aaaagatgga ggaaatcatc aagggagatt ttaggctaaa | 300 |
| taatatatct gaaactttgg tattaaacta tatgnaatga nattgtatga tccatgaaat | 360 |
| cgatctcacc taatg | 375 |

```
<210> SEQ ID NO 313
<211> LENGTH: 496
<212> TYPE: DNA
<213> ORGANISM: Glycine max

<400> SEQUENCE: 313
```

| | |
|---|---|
| ttagctttaa aatcctcagg cttactgcca aagccttaag gtaaagaact aaaagttaca | 60 |
| agatttctca atttacacca tttactagaa tagtttgact acaaaccaaa aagcattaat | 120 |
| ttagtaacta ctcgttggcc ccggattctg gtaactaaaa gttgctggtc agtggtcagc | 180 |
| aggtgagcat attcatggca gatttaaaag catgaccct agaaagattg tcatccttat | 240 |
| ttcttacctg aattggtact cccaactcct cccccaatgc acgcatcttt gccaaaccag | 300 |
| tctggtagtt tggaccacct cttctgacat atatgtgcat ttgcgctgct ttaagctttg | 360 |
| attcctgtag agtgatgagg aaaccaactc ataaactttc aaattaacaa gttgaagcag | 420 |
| attmagaata caactaacga taacacacct tctctttcag ggctcgaata atcccgttga | 480 |
| atgtggcagc aacatc | 496 |

```
<210> SEQ ID NO 314
<211> LENGTH: 600
<212> TYPE: DNA
<213> ORGANISM: Glycine max

<400> SEQUENCE: 314
```

| | |
|---|---|
| tggggttttt gatgctgaca gcttgagact aagatgtcgt attgcactat ccacatactt | 60 |
| ttcacctcca gcagctttaa gcgggtaagt ttctgcccaa cagatcagac ccaattttac | 120 |
| tctctattgt attaaacatt gagcattat ttaaggatgt agtatcgtga agtcttactt | 180 |
| ccatttggtg atccatattg tggtatacta tattgcagga atcaatctrc gtatcctgtt | 240 |
| gccattgcgg ctcatccact ggaacccaac caatttgctg ttggattgac agatgggtcc | 300 |

```
gtgaaagtga tagagcctag tgaatcagaa ggtaagtggg gaaccagtcc acctatggat    360 aatgaatat tgaacggtag ggcagcatca acatctataa caagcaacct cacacccgac     420
caggcacaaa gataagaaca ttcattgtac cataccagca tattctttcc acctgtaatt    480
tgatcacctt agattttag attttgattc cccccaattt gtcccctaaac aaggtcttgt    540 cagggtcagc tcggacataa aaatggcaaa tgtaagctct tgtcttgtaa acctgaacgc    600
```

<210> SEQ ID NO 315
<211> LENGTH: 438
<212> TYPE: DNA
<213> ORGANISM: Glycine max
<220> FEATURE:
<221> NAME/KEY: misc_feature
<222> LOCATION: (83)..(84)
<223> OTHER INFORMATION: n is a, c, g, or t

<400> SEQUENCE: 315

```
tgggttccgg cacaggccaa taatacataa acattcaatc ttggtcatgt atacaacgaa     60
acccgaatat gaattttttt ttnnaaaaaa aggagaataa taataaatat ataatttagc    120
tcctgcacct ggtgatggca ctgcagccac ggctgtaagg gttggcctga gcgccaggct    180
ggcaattgta gtargaggct ccgcggcgag agcagggac agtgttcctc tgcagcgcac     240
cgtagctgat gtacttggtc gtggctaaga tgcgccggct gatctcgctg tccagctgga    300
actcctcttc catgggcatg gagggtatcc atgtcatttc catgcccagc gctcccgcgt    360
ccgctgtcgg cgacgaagac agaagaagca gagggtggc agaaatcgcg aggaagagcc     420
acgttgcgcg cctacgat                                                 438
```

<210> SEQ ID NO 316
<211> LENGTH: 501
<212> TYPE: DNA
<213> ORGANISM: Glycine max

<400> SEQUENCE: 316

```
cttgacctac gtgaaggaga aaacggtgtc gtcagagaaa acggtgagga gttcggtgga     60
ggaggatggg tcccacgggg gcatgccgtg cttcgggcag ttattcggtg cgttccgcga    120
actgaagcgt cccatgtgga tccttctgtt ggtgacgtgt ctgaactgga tcgcctggtt    180
cccttttttg ctattcgaca ccgactggat ggggcgtgag gtgtacgag ggacagtagg     240 ggaagggaag rcgtacgata gggggtgtccg tgcgggtgcg ttggggctga tgttgaactc    300
tgttgtgctt ggtgcgacgt cgttgggagt ggaagtgctg gcgcgtgggg ttgggggcgt    360
caagaggctg tgggggattg ttaacttctt gctcgcggtt tgtttggcca tgacggtttt    420
ggttactaag atggcccaac attctcgaca atacacccta ctccccaacg cccaccagga    480 accctgcct cctcccgccg c                                              501
```

<210> SEQ ID NO 317
<211> LENGTH: 654
<212> TYPE: DNA
<213> ORGANISM: Glycine max

<400> SEQUENCE: 317

```
gagtgataga taaaccagtg aaatatattt atttatcata aacagaaaaa gaaaaacaca     60
atatgtagga cgcaatgacg catgcaggcc atgtttggct tatttagtta tttatggatc    120
ccgaggtaag ggaagttgta tgcatacgtc ttcaatgctg acgttcacac ctgagtagaa    180
```

-continued

```
gcaggggag cacggtaacc tgaaataaaa agtatttatt atagaagtca tatatata      240 tataggagaa gataaaaaga tgaaaaatat ttttcttgaa ttccttaact aacaccctaa    300
tcacactagc attttgaag aaaagagaga cctccgcagg tggttccggg aggaacatct    360
tttccacact gcctgagggt atagacaact ttccccccgc tgaagtatga ctgaaaattg    420
ttagcaagtc ggcacatgca gggcacatca acatttctca gagcgttgca gcattctgta    480
gatggcggaa tagttggccc tccgggttta tagtactcct cgcattcctc ttgaatagta    540
cccaaattac cattgcatac ttgagccgag atgcgtggca ctgctacaat gccagcaacc    600
accaacatta ttgtaaacmc taatttaatt ccctgcatcc tcaccctccc tcta           654
```

<210> SEQ ID NO 318
<211> LENGTH: 697
<212> TYPE: DNA
<213> ORGANISM: Glycine max

<400> SEQUENCE: 318

```
atctttctt tccttctgct gtatcagtaa taagcacatc tttgcatagt cattgaacag      60
atgccatgtg gggaatacct ggctcaaaaa tagatatcca aagcgtcatt attctttgga    120
gacaaaattc tgtaaagggc ataaaacttc aaaactgaga gctggatgta tcgaaagact    180
ggatggaatt atatcaattt tccgccggtt tcagcaacct ggcaatattg atacatggac    240
aatcctgtta tgttctcaaa tggatatata ctatggagga ggaaaagcag atatgataaa    300
atgatataac ttacacctaa aatcagtata ctttagtcaa ttttctctga atttctacat    360
cactaacact gtcagtaatc gcaggtgaga atatggcaga atagcttgtc atcctgatcc    420
atattttaag aggaatttaa gatgtgcttc gctcttttag gaccaagtcg gacaggacct    480
gatgttacca tgccgtccag tttaaaagaa tttacagcag gataacttcc aggatttaga    540
ttttgtgcct catgctgaca acacctactc ctagcactgc ccatgtgtgg atccagttcg    600
agtgttcttg tgtttcgttg caattccaca ctggactttt cwccaggcaa cctagtcata    660
cgactgaagt tttcttgcac tcgcatattc agtaact                              697
```

<210> SEQ ID NO 319
<211> LENGTH: 406
<212> TYPE: DNA
<213> ORGANISM: Glycine max

<400> SEQUENCE: 319

```
cgaagagaga ccaaactta gcttgagtga gtactcgatg tatagcactg aggcgagttc      60
atgctctcat tgattgctaa ttcaggcaag agttgcaagc catacttatg tatggcttga    120
tatctgttcg tgtacatata ctgctaactg agagtaaaat ggatggtttc ctctactagc    180
tatccacttg tatgattcgc tagacgtaga cacatgtagg taaggtttcc agcrattaga    240
gtatgctggt gagtcagtca gcacatacca cagatcatgg tgtaatgctc aaattcattt    300 tttattttc atatttaag gtagcaactt gatgataaat ttgtatatca cttttagtcg      360
gtctgtcaac ttacattgga gttgcaaacc tgcatctgcg tgctag                    406
```

<210> SEQ ID NO 320
<211> LENGTH: 560
<212> TYPE: DNA
<213> ORGANISM: Glycine max
<220> FEATURE:
<221> NAME/KEY: misc_feature
<222> LOCATION: (396)..(396)
<223> OTHER INFORMATION: n is a, c, g, or t

```
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t

<400> SEQUENCE: 320
tgttcgcgtc acgaagatga tcgaggtggt gttgaacgat cgattgggga agaaggtgcg      60
cgtgaagtgc aacgacgatg acaccatcgg cgacctgaag aagctggtgg cggctcagac     120
gggcacaaga gccgacaaga tccgcatcca gaagtggtac accatataca aggatcacat     180
cactctcaag gattacgaga tccacgacgg catgggtctc gaactctact acaactaaac     240
acaaggtcta tacccatctc aattcttctt tttatagata ctagctaggg ttttgttttt     300
tagggttccc raattttgat ttgttttttcg gcaataatca atggtttgta acgattatgc     360 ttctttttaat tcttcgagtt agacaataat agcgtnaaat tttcgttttt tnttgtttca     420
ggtgtgtttt atgcatgata tattactatg atctgggaat gggatgaggc gccaaatgta     480
attttgactt gcgaaagtcc ctatgatttg aataatgtnc atccccgaat gatattgggt     540
attacatacc gatgacaccc                                                 560

<210> SEQ ID NO 321
<211> LENGTH: 961
<212> TYPE: DNA
<213> ORGANISM: Glycine max
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t

<400> SEQUENCE: 321 ggagagngatg gttgaaaaga atgaggaatc taatgatgtt actacagacc ttgagttgaa     60
gactcctggg tcttctgcag atcaggttag tgttgttttc caaggatatc ccatgataga    120
agatgcatcg gattcaagtt gtgtgtgtgt gtctggtttg caggatttat catctggaca    180
aagaaaatct agcaagttgt caaggaggga aagcagctgc actgaatgga gttcattagg    240
taggtgttct tcttgtagcg ttcaggacag ctcatcaagc agtgtggtgg cragcagaaa    300
ggataangaa tgaaaaagta gacaagttag tcaagttctt gtgccttgaa gctgctgaag    360
tttttcattg tgcatctgct gcaactctgg aggtataagt cattctgttc taatcccaaa    420
ataaaagtca cttctgttat ctcttcttga ctaagaattt ggtccaagta ggtttaagtg    480
ctacataatt ttagcataaa cttccccttc tgggggaaaa cttgaaattt cagctgcaaa    540
atgaccaagt tgaccagtgt ggcttacgtg taggtttgta aattctttca tagttgttat    600
aattgcatga ttcgatacaa ttcagcaagc taacgatttg tatcatgcaa tgaattgtcg    660
atgactttga tctgtacaat acttgcatga attgatgata tcaatgcaat ttcatatagt    720
tagttcaaat cactcaagtc tgaaactcat tatttgtgtt gctaattttc atcaaagaaa    780
ttggaaagcc aaaatatact tggattgtta aatgaaaagg aactgaagta gcactagtga    840
cgcacttact tgattattcc attgttttct tccttgtgaa accaggggct taacagattt    900
tactcactct gtactttatt taactatttc attgctctat ttttatttac ttgtagaatc    960
``` g                                                                961

<210> SEQ ID NO 322
<211> LENGTH: 500
<212> TYPE: DNA
<213> ORGANISM: Glycine max
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 322
aacatggtgt ccatcaacgc aggcttaatg atggcgcatg atctctccat caaacaccct      60
tacctaagag gagccgctga gatgtacgag gatgggtttt cgtgaccgt ngatttrgct     120
ttcttggtgg acgcncacat ctgtgtctac gaggatgtct catcctacgg tcgttatttg    180
tgcttcaatc acatcataaa cacccatgag gacgctgttc agctcgcccg caagttgacg    240
cctggtgcat cttcctcctt gccgcaaagg ttggtcagag ggcgttttg gtcattttga     300
cttgtgtttt tctttgaatg ttgactttga ctttgacata ttcaactctt ttttttttatt   360
ttttatgca gtgatgacta tgggaagagt tttatcgaac agagaattag caacaagaag     420
ttgaacaaat tgatggtgga cttcgaggca taatcgactt ccatggtcat ccttttggac    480
ggtgattaga gcaatcacat                                                500

<210> SEQ ID NO 323
<211> LENGTH: 748
<212> TYPE: DNA
<213> ORGANISM: Glycine max
<220> FEATURE:
<221> NAME/KEY: misc_feature
<222> LOCATION: (655)..(655)
<223> OTHER INFORMATION: n is a, c, g, or t

<400> SEQUENCE: 323
aaccttctcg ggctttggtt ggttggtgaa gaaagtgtac ccaaagcaac atcaacattc      60
tagacccttc cttttcattc tagaccattc cacacacact caacacatat aataataatc    120
atcatagttc ataaccctca ccccaatcca attattatta atcactaagg aactcggaaa    180
aaagagggca ttggcattgc aaatggctcg ttacggcgag ggcgacaagc ggtggatcgt    240
ggaggaccgc cccgacggca ccaacgtcca caactggcac tggtccgaga ccaactgcct    300
cgactggtcc aaaaccttct tcagcaacct cctctccaac ctccctatcc tccacggcga    360
ggctaacctc ttcctcaaaa cgacgtcgct ccgctccctc gacggcgagg cctacgtcaa    420
cgtccgcaag gggaaaatca tccccggcta cgagatcagc ctcacactca attggcaggg    480
cgaagccaaa gattcccagg gaacctcgct tcttaaagtc gacggcaccg tcgagattcc    540
ctacatctcc gacgagaacg ccgacgarga tcccgaggtt agggttaccg ttaacgatga    600
gggaccggtt gggatgagga ttaaggacgc catgctttcc aaggggaagc ccttnatctt    660
ggagaaggtt agggtttggg tccagagcat ggccaaaggt ggtcctgtta aggatgaatt    720
ggaacccaag aaggttgcgc cgtcgttg                                       748

<210> SEQ ID NO 324
<211> LENGTH: 15
<212> TYPE: DNA
<213> ORGANISM: Artificial Sequence

```
<220> FEATURE:
<223> OTHER INFORMATION: Probe

<400> SEQUENCE: 324
actcgtcgtc actgc                                                15

<210> SEQ ID NO 325
<211> LENGTH: 17
<212> TYPE: DNA
<213> ORGANISM: Artificial Sequence
<220> FEATURE:
<223> OTHER INFORMATION: Probe

<400> SEQUENCE: 325
aagctgtacg gcaaaga                                              17

<210> SEQ ID NO 326
<211> LENGTH: 18
<212> TYPE: DNA
<213> ORGANISM: Artificial Sequence
<220> FEATURE:
<223> OTHER INFORMATION: Probe

<400> SEQUENCE: 326
ttcaacagtc tggttagg                                             18

<210> SEQ ID NO 327
<211> LENGTH: 13
<212> TYPE: DNA
<213> ORGANISM: Artificial Sequence
<220> FEATURE:
<223> OTHER INFORMATION: Probe

<400> SEQUENCE: 327
tgcgccaatg cat                                                  13

<210> SEQ ID NO 328
<211> LENGTH: 17
<212> TYPE: DNA
<213> ORGANISM: Artificial Sequence
<220> FEATURE:
<223> OTHER INFORMATION: Probe

<400> SEQUENCE: 328
tctatacagc cttcatg                                              17

<210> SEQ ID NO 329
<211> LENGTH: 16
<212> TYPE: DNA
<213> ORGANISM: Artificial Sequence
<220> FEATURE:
<223> OTHER INFORMATION: Probe

<400> SEQUENCE: 329
cccaaaaccc tgaaag                                               16

<210> SEQ ID NO 330
<211> LENGTH: 21
<212> TYPE: DNA
<213> ORGANISM: Artificial Sequence
<220> FEATURE:
<223> OTHER INFORMATION: Probe

<400> SEQUENCE: 330
cagaaacttt aaattggtaa c                                         21
```

```
<210> SEQ ID NO 331
<211> LENGTH: 17
<212> TYPE: DNA
<213> ORGANISM: Artificial Sequence
<220> FEATURE:
<223> OTHER INFORMATION: Probe

<400> SEQUENCE: 331
tgaacggaaa gtgcctt                                                    17

<210> SEQ ID NO 332
<211> LENGTH: 14
<212> TYPE: DNA
<213> ORGANISM: Artificial Sequence
<220> FEATURE:
<223> OTHER INFORMATION: Probe

<400> SEQUENCE: 332
tcgggcgagg agtg                                                       14

<210> SEQ ID NO 333
<211> LENGTH: 19
<212> TYPE: DNA
<213> ORGANISM: Artificial Sequence
<220> FEATURE:
<223> OTHER INFORMATION: Probe

<400> SEQUENCE: 333
tttggcattg taacatagt                                                  19

<210> SEQ ID NO 334
<211> LENGTH: 19
<212> TYPE: DNA
<213> ORGANISM: Artificial Sequence
<220> FEATURE:
<223> OTHER INFORMATION: Probe

<400> SEQUENCE: 334 tgactttag tctcatgaa                                                   19

<210> SEQ ID NO 335
<211> LENGTH: 20
<212> TYPE: DNA
<213> ORGANISM: Artificial Sequence
<220> FEATURE:
<223> OTHER INFORMATION: Probe

<400> SEQUENCE: 335
cgttagttgt attcttaatc                                                 20

<210> SEQ ID NO 336
<211> LENGTH: 19
<212> TYPE: DNA
<213> ORGANISM: Artificial Sequence
<220> FEATURE:
<223> OTHER INFORMATION: Probe

<400> SEQUENCE: 336
caggaatcaa tctgcgtat                                                  19

<210> SEQ ID NO 337
<211> LENGTH: 17
<212> TYPE: DNA
<213> ORGANISM: Artificial Sequence
<220> FEATURE:
<223> OTHER INFORMATION: Probe
```

```
<400> SEQUENCE: 337
ttgtagtaag aggctcc                                                      17

<210> SEQ ID NO 338
<211> LENGTH: 16
<212> TYPE: DNA
<213> ORGANISM: Artificial Sequence
<220> FEATURE:
<223> OTHER INFORMATION: Probe

<400> SEQUENCE: 338
cctatcgtac gtcttc                                                       16

<210> SEQ ID NO 339
<211> LENGTH: 22
<212> TYPE: DNA
<213> ORGANISM: Artificial Sequence
<220> FEATURE:
<223> OTHER INFORMATION: Probe

<400> SEQUENCE: 339
aacattattg taaacactaa tt                                                22

<210> SEQ ID NO 340
<211> LENGTH: 14
<212> TYPE: DNA
<213> ORGANISM: Artificial Sequence
<220> FEATURE:
<223> OTHER INFORMATION: Probe

<400> SEQUENCE: 340
cctggtgaaa agtc                                                         14

<210> SEQ ID NO 341
<211> LENGTH: 18
<212> TYPE: DNA
<213> ORGANISM: Artificial Sequence
<220> FEATURE:
<223> OTHER INFORMATION: Probe

<400> SEQUENCE: 341
taaggtttcc agcaatta                                                     18

<210> SEQ ID NO 342
<211> LENGTH: 16
<212> TYPE: DNA
<213> ORGANISM: Artificial Sequence
<220> FEATURE:
<223> OTHER INFORMATION: Probe

<400> SEQUENCE: 342
tttagggttc ccgaat                                                       16

<210> SEQ ID NO 343
<211> LENGTH: 14
<212> TYPE: DNA
<213> ORGANISM: Artificial Sequence
<220> FEATURE:
<223> OTHER INFORMATION: Probe

<400> SEQUENCE: 343
tgtggtggca agca                                                         14

<210> SEQ ID NO 344
```

```
<211> LENGTH: 18
<212> TYPE: DNA
<213> ORGANISM: Artificial Sequence
<220> FEATURE:
<223> OTHER INFORMATION: Probe

<400> SEQUENCE: 344
caccaagaaa gccaaatc                                                 18

<210> SEQ ID NO 345
<211> LENGTH: 15
<212> TYPE: DNA
<213> ORGANISM: Artificial Sequence
<220> FEATURE:
<223> OTHER INFORMATION: Probe

<400> SEQUENCE: 345
cgacgaagat cccga                                                    15

<210> SEQ ID NO 346
<211> LENGTH: 13
<212> TYPE: DNA
<213> ORGANISM: Artificial Sequence
<220> FEATURE:
<223> OTHER INFORMATION: Probe

<400> SEQUENCE: 346
cgtcacggcg gag                                                      13

<210> SEQ ID NO 347
<211> LENGTH: 16
<212> TYPE: DNA
<213> ORGANISM: Artificial Sequence
<220> FEATURE:
<223> OTHER INFORMATION: Probe

<400> SEQUENCE: 347
agctgtacgg cgaaga                                                   16

<210> SEQ ID NO 348
<211> LENGTH: 17
<212> TYPE: DNA
<213> ORGANISM: Artificial Sequence
<220> FEATURE:
<223> OTHER INFORMATION: Probe

<400> SEQUENCE: 348
caacagtctg gtttgga                                                  17

<210> SEQ ID NO 349
<211> LENGTH: 15
<212> TYPE: DNA
<213> ORGANISM: Artificial Sequence
<220> FEATURE:
<223> OTHER INFORMATION: Probe

<400> SEQUENCE: 349
tgcgccaatg aattc                                                    15

<210> SEQ ID NO 350
<211> LENGTH: 16
<212> TYPE: DNA
<213> ORGANISM: Artificial Sequence
<220> FEATURE:
<223> OTHER INFORMATION: Probe

<400> SEQUENCE: 350
```
tatacagcct ccatgt                                                    16

<210> SEQ ID NO 351
<211> LENGTH: 14
<212> TYPE: DNA
<213> ORGANISM: Artificial Sequence
<220> FEATURE:
<223> OTHER INFORMATION: Probe

<400> SEQUENCE: 351
cccaaaaccc cgaa                                                      14

<210> SEQ ID NO 352
<211> LENGTH: 21
<212> TYPE: DNA
<213> ORGANISM: Artificial Sequence
<220> FEATURE:
<223> OTHER INFORMATION: Probe

<400> SEQUENCE: 352
agaaacttta aattggcaac t                                              21

<210> SEQ ID NO 353
<211> LENGTH: 18
<212> TYPE: DNA
<213> ORGANISM: Artificial Sequence
<220> FEATURE:
<223> OTHER INFORMATION: Probe

<400> SEQUENCE: 353
ctgaacggaa agtgcttt                                                  18

<210> SEQ ID NO 354
<211> LENGTH: 14
<212> TYPE: DNA
<213> ORGANISM: Artificial Sequence
<220> FEATURE:
<223> OTHER INFORMATION: Probe

<400> SEQUENCE: 354
cgggttcggg caag                                                      14

<210> SEQ ID NO 355
<211> LENGTH: 17
<212> TYPE: DNA
<213> ORGANISM: Artificial Sequence
<220> FEATURE:
<223> OTHER INFORMATION: Probe

<400> SEQUENCE: 355
tggcattgta acctagt                                                   17

<210> SEQ ID NO 356
<211> LENGTH: 19
<212> TYPE: DNA
<213> ORGANISM: Artificial Sequence
<220> FEATURE:
<223> OTHER INFORMATION: Probe

<400> SEQUENCE: 356 tgactttag tctcatgaa                                                  19

<210> SEQ ID NO 357
<211> LENGTH: 19
<212> TYPE: DNA

```
<213> ORGANISM: Artificial Sequence
<220> FEATURE:
<223> OTHER INFORMATION: Probe

<400> SEQUENCE: 357
tcgttagttg tattctgaa                                                        19

<210> SEQ ID NO 358
<211> LENGTH: 18
<212> TYPE: DNA
<213> ORGANISM: Artificial Sequence
<220> FEATURE:
<223> OTHER INFORMATION: Probe

<400> SEQUENCE: 358
tgcaggaatc aatctacg                                                         18

<210> SEQ ID NO 359
<211> LENGTH: 18
<212> TYPE: DNA
<213> ORGANISM: Artificial Sequence
<220> FEATURE:
<223> OTHER INFORMATION: Probe

<400> SEQUENCE: 359
ctggcaattg tagtagga                                                         18

<210> SEQ ID NO 360
<211> LENGTH: 15
<212> TYPE: DNA
<213> ORGANISM: Artificial Sequence
<220> FEATURE:
<223> OTHER INFORMATION: Probe

<400> SEQUENCE: 360
cctatcgtac gcctt                                                            15

<210> SEQ ID NO 361
<211> LENGTH: 23
<212> TYPE: DNA
<213> ORGANISM: Artificial Sequence
<220> FEATURE:
<223> OTHER INFORMATION: Probe

<400> SEQUENCE: 361
caacattatt gtaaaccta att                                                    23

<210> SEQ ID NO 362
<211> LENGTH: 14
<212> TYPE: DNA
<213> ORGANISM: Artificial Sequence
<220> FEATURE:
<223> OTHER INFORMATION: Probe

<400> SEQUENCE: 362
cctggagaaa agtc                                                             14

<210> SEQ ID NO 363
<211> LENGTH: 17
<212> TYPE: DNA
<213> ORGANISM: Artificial Sequence
<220> FEATURE:
<223> OTHER INFORMATION: Probe

<400> SEQUENCE: 363
taaggtttcc agcgatt                                                          17
```

```
<210> SEQ ID NO 364
<211> LENGTH: 17
<212> TYPE: DNA
<213> ORGANISM: Artificial Sequence
<220> FEATURE:
<223> OTHER INFORMATION: Probe

<400> SEQUENCE: 364
tttagggttc ccaaatt                                                  17

<210> SEQ ID NO 365
<211> LENGTH: 15
<212> TYPE: DNA
<213> ORGANISM: Artificial Sequence
<220> FEATURE:
<223> OTHER INFORMATION: Probe

<400> SEQUENCE: 365
agtgtggtgg cgagc                                                    15

<210> SEQ ID NO 366
<211> LENGTH: 17
<212> TYPE: DNA
<213> ORGANISM: Artificial Sequence
<220> FEATURE:
<223> OTHER INFORMATION: Probe

<400> SEQUENCE: 366
tccaccaaga aagctaa                                                  17

<210> SEQ ID NO 367
<211> LENGTH: 15
<212> TYPE: DNA
<213> ORGANISM: Artificial Sequence
<220> FEATURE:
<223> OTHER INFORMATION: Probe

<400> SEQUENCE: 367
cgacgaggat cccga                                                    15
```

RESISTANCE ALLELES IN SOYBEAN

RELATED APPLICATION INFORMATION

This Application claims the benefit of U.S. Provisional Application No. 61/480,430 filed 29 Apr. 2011 and is a Divisional application of U.S. Ser. No. 13/460,826 filed on 30 Apr. 2012, the contents of which are incorporated herein by reference herein.

STATEMENT REGARDING ELECTRONIC FILING OF A SEQUENCE LISTING

A Sequence Listing in ASCII text format, submitted under 37 C.F.R. §1.821, entitled 73238_ST25 USNP.txt, 173,326 bytes in size, generated on Apr. 30, 2012 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having tolerance to iron deficiency chlorosis (IDC).

BACKGROUND

Soybean (*Glycine max* L. Merr) is a major cash crop and investment commodity in North America and elsewhere. Soybean oil is one of the most widely used edible oils, and soybeans are used worldwide both in animal feed and in human food production. Iron deficiency chlorosis (IDC) in soybeans is a widespread problem in the Upper Midwest (North Central region) of the United States and is the result of reduced availability of iron and therefore, reduced iron levels in the plant. High pH in the soil, high water tables, too much rainfall, salinity in the soil, calcium carbonate in the topsoil, and elevated soil nitrate levels all contribute to the problem. The symptoms include interveinal chlorosis (the leaves turn yellow while the veins remain green) and stunting. If the youngest leaves and growing points are damaged due to iron deficiency, growth of the plant will be stunted and yields are reduced substantially.

Different varieties of soybean vary in their sensitivity or tolerance to iron deficiency. Therefore, one of the most effective control measures is planting IDC tolerant soybean varieties, and thus varietal selection is important for the management of IDC. However, currently, determining whether a soybean cultivar might have tolerance to IDC typically involves testing each cultivar in the field or greenhouse under conditions that typically produce IDC. Thus, the present invention overcomes the shortcomings in the art by providing markers associated with tolerance to IDC, thereby allowing the characterization of soybean cultivars for IDC tolerance by molecular analysis rather than phenotypic analysis.

SUMMARY OF THE INVENTION

Compositions and methods for identifying, selecting and/or producing soybean plants with tolerance to iron deficiency chlorosis (IDC) are provided. As described herein, a marker associated with enhanced IDC tolerance may comprise, consist essentially of or consist of a single allele or a combination of alleles at one or more genetic loci.

Accordingly, in one aspect of the present invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein said marker is located within a chromosomal interval selected from the group consisting of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; and (k) any combination of (a) through (j) above, thereby identifying and/or selecting an IDC tolerant soybean plant or part thereof.

In another aspect, the present invention provides a method of identifying and/or selecting an iron deficiency chlorosis (IDC) tolerant soybean plant or part thereof, comprising: detecting, in said soybean plant or part thereof, the presence of a marker associated with IDC tolerance, wherein said marker is selected from the group consisting of: (a) a G allele at SY0152AQ; (b) a G allele at SY0724AQ; (c) an insertion of a nucleotide sequence of CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ, (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; (hh) a A allele at SY0121AQ; (ii) a A allele at SY0122AQ; (jj) a A allele at SY1076AQ; (kk) a A allele at SY0271AQ; (ll) a A allele at SY0307AQ; (mm) a A allele at SY0778AQ; (nn) a C allele at SY1300AQ; (oo) a A allele at SY0386AQ; (pp) a G allele at SY0952AQ; (qq) a A allele at SY0399AQ; (rr) a A allele at SY808AQ; (ss) a A allele at SY0840AQ; (tt) a G allele at SY0474AQ; (uu) a G allele at SY2045AQ; (vv) a G allele at SY1069AQ; (ww) a A allele at SY0622AQ; (xx) a A allele at SY0066AQ; (yy) a G allele at SY0623AQ; (zz) a A allele at SY0673AQ, (aaa) a G allele at SY0674AQ, (bbb) a A allele at SY0928AQ, (ccc) a A allele at Sy2140AQ and any combination of (a) through (ccc) above, thereby identifying and/or selecting an IDC tolerant soybean plant or part thereof.

In an additional aspect of the present invention, a method of identifying and/or selecting an iron deficiency chlorosis (IDC) tolerant soybean plant or part thereof is provided, the method comprising: detecting, in said soybean plant or part thereof, the presence of a combination of genetic markers (haplotype) associated with IDC tolerance in a soybean plant, the combination of genetic markers selected from the group consisting of: (a) a G allele at SY0152AQ and a G allele at SY0724AQ; (b) an insertion of a nucleotide sequence of CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, and any combination thereof; (h) a G allele at SY0369AQ, a G allele at SY0370AQ, a T allele at SY0372AQ, a G allele at SY0373AQ, an insertion of nucleotide sequence CTTACC at SY0374AQ, and any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, and any combination thereof; (l) a G allele at SY0499AQ, an A allele at SY0500AQ, an A allele at SY0501AQ, a G allele at SY0503AQ, a G allele at SY1333AQ, an A allele at SY0504AQ, and any combination thereof; (m) a T allele at SY0224AQ, a C allele at SY0225AQ, a C allele at SY0226AQ, and any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, and any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, and any combination thereof; (p) a G allele at SY0422AQ, an A allele at SY1091AQ, a C allele at SY0133AQ, a G allele at SY0425AQ, and any combination thereof; (q) a C allele at SY0422AQ, a G allele at SY1091AQ, a G allele at SY1258AQ, a G allele at SY1259AQ, an A allele at SY0424CQ, an A allele at SY0425AQ, and any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, and any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, and any combination thereof; and (w) any combination of (a) through (v) above, thereby identifying and/or selecting an IDC tolerant soybean plant or part thereof.

In other aspects, the present invention provides a method of producing an iron deficiency chlorosis (IDC) tolerant soybean plant or part thereof, comprising: detecting, in a soybean germplasm, the presence of a marker associated with IDC tolerance in a soybean plant, wherein said marker is located within a chromosomal interval selected from the group consisting of: (a) a chromosomal interval on chromosome 5 defined by and including a G allele at SY0152AQ and a G allele at SY0724AQ; (b) a chromosomal interval on chromosome 5 defined by and including an insertion of a nucleotide sequence of CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; and (k) any combination of (a) through (j) above, and producing a soybean plant from said soybean germplasm, thereby producing an IDC tolerant soybean plant or part thereof.

In further aspects of the invention, a method of producing an iron deficiency chlorosis (IDC) tolerant soybean plant or part thereof is provided, the method comprising: detecting, in a soybean germplasm, the presence of a marker associated with IDC tolerance, wherein said marker is selected from the group consisting of: (a) a G allele at SY0152AQ; (b) a G allele at SY0724AQ; (c) an insertion of nucleotide sequence of CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ; (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079B; (gg) a G allele at SY0422AQ; (hh) a A allele at SY0121AQ; (ii) a A allele at SY0122AQ; (jj) a A allele at SY1076AQ; (kk) a A allele at SY0271AQ; (ll) a A allele at SY0307AQ; (mm) a A allele at SY0778AQ; (nn) a C allele at SY1300AQ; (oo) a A allele at SY0386AQ; (pp) a G allele at SY0952AQ; (qq) a A allele at SY0399AQ; (rr) a A allele at SY808AQ; (ss) a A allele at SY0840AQ; (tt) a G allele at SY0474AQ; (uu) a G allele at SY2045AQ; (vv) a G allele at SY1069AQ; (ww) a A allele at SY0622AQ; (xx) a A allele at SY0066AQ; (yy) a G allele at SY0623AQ; (zz) a A allele at SY0673AQ, (aaa) a G allele at SY0674AQ, (bbb) a A allele at SY0928AQ, (ccc) a A allele at Sy2140AQ and any combination of (a) through (ccc) above, thereby identifying and/or selecting an IDC tolerant soybean plant or part thereof.

In another aspect of the present invention, a method of producing an iron deficiency chlorosis (IDC) tolerant soybean plant or part thereof is provided, the method comprising: detecting, in said soybean plant or part thereof, the presence of a combination of genetic markers associated with IDC tolerance in a soybean plant, the combination of genetic markers selected from the group consisting of: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, and any combination thereof; (h) a G allele at SY0369AQ, a G allele at SY0370AQ, a T allele at SY0372AQ, a G allele at SY0373AQ, an insertion of nucleotide sequence CTTACC at SY0374AQ, and any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, and any combination thereof; (l) a G allele at SY0499AQ, an A allele at SY0500AQ, an A allele at SY0501AQ, a G allele at SY0503AQ, a G allele at SY1333AQ, an A allele at SY0504AQ, and any combination thereof; (m) a T allele at SY0224AQ, a C allele at SY0225AQ, a C allele at SY0226AQ, and any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, and any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, and any combination thereof; (p) a G allele at SY0422AQ, an A allele at SY1091AQ, a C allele at SY0133AQ, a G allele at SY0425AQ, and any combination thereof; (q) a C allele at SY0422AQ, a G allele at SY1091AQ, a G allele at SY1258AQ, a G allele at SY1259AQ, an A allele at SY0424CQ, an A allele at SY0425AQ, and any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, and any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, and any combination thereof; and (w) and any combination of (a) through (v) and producing a soybean plant from said soybean germplasm, thereby producing an IDC tolerant soybean plant or part thereof.

In additional aspects, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, wherein said marker is located within a chromosomal interval selected from the group consisting of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; and (k) any combination of (a) through (j) above, and selecting a progeny soybean plant or germplasm that possesses said marker within its genome, thereby selecting an IDC tolerant soybean plant or germplasm.

Other aspects of the present invention provide a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, wherein said marker is selected from the group consisting of: (a) a G allele at SY0152AQ; (b) a G allele at SY0724AQ; (c) an insertion of nucleotide sequence CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ; (l) an A allele at SY0501AQ; (m) a G allele at SY0503AQ; (n) a T allele at SY0224AQ; (o) a C allele at SY0225AQ; (p) a C allele at SY0226AQ, (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; (hh) a A allele at SY0121AQ; (ii) a A allele at SY0122AQ; (jj) a A allele at SY1076AQ; (kk) a A allele at SY0271AQ; (ll) a A allele at SY0307AQ; (mm) a A allele at SY0778AQ; (nn) a C allele at SY1300AQ; (oo) a A allele at SY0386AQ; (pp) a G allele at SY0952AQ; (qq) a A allele at SY0399AQ; (rr) a A allele at SY808AQ; (ss) a A allele at SY0840AQ; (tt) a G allele at SY0474AQ; (uu) a G allele at SY2045AQ; (vv) a G allele at SY1069AQ; (ww) a A allele at SY0622AQ; (xx) a A allele at SY0066AQ; (yy) a G allele at SY0623AQ; (zz) a A allele at SY0673AQ, (aaa) a G allele at SY0674AQ, (bbb) a A allele at SY0928AQ, (ccc) a A allele at Sy2140AQ and any combination of (a) through (ccc) above, thereby identifying and/or selecting an IDC tolerant soybean plant or part thereof.

In other embodiments, the present invention provides a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a combination of genetic markers (haplotype) associated with IDC tolerance in a soybean plant, the combination of genetic markers selected from the group consisting of: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, and any combination thereof; (h) a G allele at SY0369AQ, a G allele at SY0370AQ, a T allele at SY0372AQ, a G allele at SY0373AQ, an insertion of nucleotide sequence CTTACC at SY0374AQ, and any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, and any combination thereof; (l) a G allele at SY0499AQ, an A allele at SY0500AQ, an A allele at SY0501AQ, a G allele at SY0503AQ, a G allele at SY1333AQ, an A allele at SY0504AQ, and any combination thereof; (m) a T allele at SY0224AQ, a C allele at SY0225AQ, a C allele at SY0226AQ, and any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, and any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, and any combination thereof; (p) a G allele at SY0422AQ, an A allele at SY1091AQ, a C allele at SY0133AQ, a G allele at SY0425AQ, and any combination thereof; (q) a C allele at SY0422AQ, a G allele at SY1091AQ, a G allele at SY1258AQ, a G allele at SY1259AQ, an A allele at SY0424CQ, an A allele at SY0425AQ, and any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, and any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, and any combination thereof; and (w) and any combination of (a) through (v); and selecting a progeny soybean plant or germplasm that possesses said marker within its genome, thereby selecting an IDC tolerant soybean plant or germplasm.

Soybean plants and/or germplasms identified, produced or selected by the methods of this invention are also provided, as are any progeny and/or seeds derived from a soybean plant or germplasm identified, produced or selected by these methods.

These and other aspects of the invention are set forth in more detail in the description of the invention below.

BRIEF DESCRIPTION OF THE DRAWINGS

FIG. 1 shows the connected population structure developed from the parental materials. The lines indicate a population and the number inside the circles indicate the parent material.

DETAILED DESCRIPTION

The present invention provides compositions and methods for identifying, selecting and/or producing soybean plants having iron deficiency tolerance, as well as soybean plants and parts thereof, including but not limited to seeds, that are identified, selected and/or produced by a method of this invention. The present invention further provides an assay for the detection of IDC in a soybean plant. In addition, the present invention provides soybean plants and/or soybean germplasm having within their genomes one or more SNP or QTL markers associated with tolerance to iron deficiency chlorosis.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

Definitions

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP, QTL, haplotype) can mean one marker or a plurality of markers (e.g., 2, 3, 4, 5, 6, and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with tolerance to iron deficiency chlorosis in a soybean plant relative to a control soybean plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with an IDC tolerance allele" refers to a marker whose presence or absence can be used to predict whether a plant will display tolerance to iron deficiency chlorosis.

Iron deficiency chlorosis (IDC) is a physiological disease in soybean plants that is caused by a lack of iron in the plant. Most soils contain sufficient iron. However, in some soils the iron is insoluble and thus unavailable to the plants. As a result of the unavailability of the iron in the soil, plants grown in such soil lack iron. It is also known in the art that IDC can be the result of any one or combination of a) the plant's inability to uptake iron from the soil (e.g. iron insolubility, or root uptake hindered), b) the inability of the plant to transport the iron to the leaf and c) the inability of the plant to activate the iron in the leaf. Any one of these (a-c) scenarios can lead to the symptoms that are indicative of IDC. Herein, the terms "Iron deficiency chlorosis" or "IDC" interchangeably represent a physiological disease in any plant that is caused by the lack of iron whether that lack of iron is due to the plant's inability to uptake the iron; a plant's inability to transport the iron or thirdly the plant's inability to activate the iron in the leaf tissue.

As used herein, the terms "low iron," "low iron conditions," "low iron growth conditions," "low iron availability" or "iron deficiency" or the like refer to conditions where iron availability is less than optimal for soybean growth and can cause physiological disease, e.g., iron deficiency chlorosis, due to the lack of soluble or available iron in the growth medium (e.g., soil). While the absolute level of iron may be sufficient, the form of the iron, which is affected by various environmental factors, may make the iron that is present unavailable for plant use (cannot be taken up by the plant's roots). See, Dahiya and Singh, *Plant and Soil* 51:13-18 (1979). For example, high carbonate levels, high pH, high salt content (high salinity; e.g., phosphorus, manganese and zinc), saturated soils (and/or poor drainage) and/or other environmental factors can result in lower iron solubility; thereby, reducing the solubilized forms of iron that are necessary for plant uptake. Thus, soils having low available iron include, but are not limited to, those that are calcareous (i.e., high in calcium carbonate) and have a high pH (greater than 7.5). Iron levels in soil that are optimal/not optimal for plant growth are well known in the art as are methods for measuring iron content.

The initial symptoms of iron deficiency chlorosis include interveinal chlorosis in the newly developing trifoliate leaves. Interveinal chlorosis can be described as a contrast of the inter-vein tissue color, which turns yellow, as compared to the vein color, which remains green. The interveinal chlorosis is referred to as "yellow flash." Yellow flash occurs at about 21 days after planting or at the V2 stage of growth. Eventually, the leaves of symptomatic plants may develop necrotic spots that coalesce and then, finally the leaves may fall off. Tolerant varieties may express more normal leaf color and little contrast between inter-vein tissue color and vein color. Intolerant varieties express greenish-yellow or yellow or yellowish-white colored inter-vein tissue while the vein remains green which produces relatively greater and greater contrast. Intolerant varieties are also slow in vegetative growth and biomass compared to tolerant varieties. Extremely intolerant varieties produce white trifoliate leaves that quickly decline and become necrotic. Extremely intolerant plants essentially stop growing vegetatively, producing maximum contrast compared to tolerant varieties.

The term "recovery" as used herein refers to the extent of iron deficiency chlorosis symptoms as measured in newly developed leaves or about 14 days after the initial yellow flash. Tolerant varieties signal recovery by producing a more normal green color in the new leaves (i.e., little contrast between leaf tissue and veinal tissue) as compared to the initial yellow flash response measured earlier in that same plant. Intolerant varieties continue to produce yellow flash symptoms in the new leaves resulting in a continuing contrast between interveinal tissue and the veins, as discussed herein.

As used herein, the term "iron deficiency tolerance" or "iron deficiency chlorosis tolerance" refers to a plant's ability to have increased efficiency in uptake of, transporting and activating iron as compared to one or more control plants not tolerant to IDC (e.g., a plant lacking a marker associated with iron deficiency tolerance). In some cases an iron deficiency tolerant plant can uptake iron, transport iron or activate iron once in the leaf tissue at an increased or more efficient rate than a control plant not tolerant to iron deficiency chlorosis grown in the same or similar environment.

Thus, "tolerance" in a soybean plant to iron deficient or low iron growth conditions is an indication that the soybean plant is less affected by the low iron growth conditions with respect to yield, survivability and/or other relevant agronomic measures, compared to a less tolerant, more "susceptible" plant. Tolerance is a relative term, indicating that a "tolerant" soybean plant survives and/or produces a better yield in iron deficient growth conditions when compared to a different (less tolerant) soybean plant (e.g., a different soybean strain or variety) grown in similar conditions of low iron availability. That is, under iron deficient growth conditions a tolerant plant can have a greater survival rate and/or yield, as compared to a soybean plant that is susceptible or intolerant to these low iron growth conditions. Iron deficiency "tolerance" sometimes can be used interchangeably with iron deficiency "resistance." Iron deficiency chlorosis intolerant soybean varieties and cultivars are well known in the art. A non-limiting example of an IDC intolerant soybean cultivar is soybean cultivar M08851 (U.S. Pat. No. 7,126,047).

In some embodiments, a plant of this invention that is iron deficiency tolerant or iron deficiency chlorosis tolerant includes a plant that exhibits reduced yellow flash symptoms as compared to a plant not having in its genome the genetic markers described herein as associated with IDC tolerance. In other embodiments, a plant of this invention that is IDC tolerant also includes a plant that exhibits recovery from yellow flash as compared to a plant not having in its genome the genetic markers described herein as associated with IDC tolerance. In still other embodiments, a plant of this invention that is iron deficiency tolerant includes a plant that exhibits both reduced yellow flash symptoms and recovery from yellow flash as compared to a plant not having in its genome the marker(s) described herein as associated with IDC tolerance.

As is understood by the skilled artisan, soybean plant tolerance to low-available iron conditions varies widely, and can represent a range of more tolerant to less-tolerant phenotypes. Non-limiting examples of methods for determining the relative tolerance or susceptibility of different plants, plant lines or plant families under low-available iron conditions include visual observation (e.g., visual chlorosis scoring system) (See, Helms et al. Agronomy J 102:492-498 (2010)) and/or electronic scanning using a Greenseeker® RT100 radiometer (See, PCT/US10/46303; WO/2011/022719). Other methods for determining IDC tolerance include but are not limited to the use of hydroponics (See, Niebur and Fehr, *Crop Sci.* 21:551-554 (1981)).

In the case of a visual chlorosis scoring system, a plant that is grown in soil having low available iron, or in low available iron experimental conditions, can be assigned a tolerance rating of between 1 (highly tolerant; yield and survivability not significantly affected; all plants normal green color) to 9 (highly susceptible; most or all plants dead; those that live are stunted and have little living tissue) based on visual observation of the level of chlorosis in the plant.

In a further example, a radiometer can be used to take electronic measurements. In this case, a plant that is grown in a known low available iron soil, or in low available iron experimental conditions, is assigned a tolerance rating of between 1 (highly tolerant; yield and survivability not significantly affected; all plants normal green color) to 0 (highly susceptible; most or all plants dead; those that live are stunted and have little living tissue) based on the reading provided by scanning the foliage with the radiometer.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome.

Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with IDC tolerance may be introgressed from a donor into a recurrent parent that is IDC intolerant. The resulting offspring could then be backcrossed one or more times and selected until the progeny possess the genetic marker(s) associated with iron deficiency chlorosis tolerance in the recurrent parent background.

As used herein, the term "linkage" refers to the degree with which one marker locus is associated with another marker locus or some other locus (for example, an IDC tolerance locus). The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., IDC tolerance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (www.soybase.org). In some embodiments, a genetic marker of this invention is an SNP allele, a SNP allele located in a chromosome interval and/or a haplotype (combination of SNP alleles) each of which is associated with IDC tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 2)

Accordingly, in some embodiments of this invention, a marker is detected by amplifying a *Glycine* sp. nucleic acid with two oligonucleotide primers by, for example, the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of probes of this invention include SEQ ID NOs:19-54 and 137-300.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.).

The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny", "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "reference sequence" refers to a defined nucleotide sequence used as a basis for nucleotide sequence comparison (e.g., Chromosome 3 of *Glycine max* cultivar Williams 82). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic Mapping

Genetic loci correlating with particular phenotypes, such as tolerance to iron deficiency chlorosis, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with tolerance to iron deficiency chlorosis in soybean. Detection of these markers and/or other linked markers can be used to identify, select and/or produce soybean plants having IDC tolerance and/or to eliminate soybean plants from breeding programs or from planting that do not have IDC tolerance

Markers Associated with Tolerance to Iron Deficiency Chlorosis

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

Table 1 provides a sample listing of twenty IDC associated markers (SNPs) and respective associated IDC trait or traits phenotyped. Table 2 provides a summary of markers associated with IDC tolerance in soybean, their corresponding name, the physical location of the marker on the respective soybean chromosome, and the target allele that is associated with IDC tolerance.

Markers of the present invention are described herein with respect to the positions of marker loci in the 8X public build of the Williams82 soybean genome at the SoyBase internet resource (www.soybase.org/SequenceIntro.php) or USDA at (bfgl.anri.barc.usda.gov/cgi-bin/soybean/Linkage.pl). See Table 2 Table 2 below.

TABLE 1

Twenty genetic markers associated and respective IDC tolerance traits.

| Assay name | Linked IDC Trait* |
|---|---|
| SY0226AQ | Mean (IC_R); flash (ICFLR); recovery (ICR_R) |
| SY1076AQ | Mean (IC_R); flash (ICFLR); recovery (ICR_R) |
| SY0271AQ | Mean (IC_R); flash (ICFLR); recovery (ICR_R) |
| SY0781AQ | Mean (IC_R); flash (ICFLR); recovery (ICR_R) |
| SY0322AQ | Mean (IC_R); flash (ICFLR); recovery (ICR_R) |
| SY1300AQ | Mean (IC_R); flash (ICFLR); recovery (ICR_R) |
| SY0325AQ | Mean (IC_R); flash (ICFLR); recovery (ICR_R) |
| SY0399AQ | Mean (IC_R); flash (ICFLR); recovery (ICR_R) |
| SY0424CQ | Mean (IC_R); flash (ICFLR); recovery (ICR_R) |
| SY0425AQ | Mean (IC_R); flash (ICFLR); recovery (ICR_R) |
| SY0840AQ | Mean (IC_R); flash (ICFLR); recovery (ICR_R) |
| SY0474AQ | Mean (IC_R); flash (ICFLR); recovery (ICR_R) |
| SY0498AQ | Mean (IC_R); flash (ICFLR); recovery (ICR_R) |
| SY0499AQ | Mean (IC_R); flash (ICFLR); recovery (ICR_R) |
| SY0504AQ | Mean (IC_R); flash (ICFLR); recovery (ICR_R) |
| SY0622AQ | Mean (IC_R); flash (ICFLR); recovery (ICR_R) |
| SY0623AQ | Mean (IC_R); flash (ICFLR); recovery (ICR_R) |
| SY0673AQ | Mean (IC_R); flash (ICFLR); recovery (ICR_R) |
| SY0674AQ | Mean (IC_R); flash (ICFLR); recovery (ICR_R) |
| SY0928AQ | Mean (IC_R); flash (ICFLR); recovery (ICR_R) |

*See Table 6, Example 2, for a definition of the codes as used herein for the IDC traits.

| Assay name | Public SNP name/ Locus name | Chromo- some | Physical position in Williams82 genome | Linkage group | LG position (cM) | SEQ ID NO for DNA fragment comprising SNP/indel | SEQ ID NO for probe 1 Sequence | Probe 1 detected nucleo- tide | SEQ ID NO for probe Sequence | Probe 2 detected nucleo- tide |
|---|---|---|---|---|---|---|---|---|---|---|
| SY0226AQ | BARC-039595-07515 | 14 | 5029071 | B2 | 26.97 | 6 | 24 | G | 42 | C |
| SY1076AQ | | 6 | 3533016 | C2 | 32.70 | 307 | 308 | A | 309 | C |
| SY0271AQ | | 6 | 3369861 | C2 | 36.69 | 310 | 311 | A | 312 | G |
| SY0781AQ | | 2 | 2850183 | D1b | 22.10 | | | G | | A |
| SY0322AQ | | 2 | 3091839 | D1b | 22.70 | | | T | | A |
| SY1300AQ | | 2 | 4189924 | D1b | 33.99 | 319 | 320 | C | 321 | A |
| SY0325AQ | | 2 | 4545096 | D1b | 36.6 | | | A | | G |
| SY0399AQ | | 15 | 24823131 | E | 94.73 | 328 | 329 | A | 330 | G |
| SY0424CQ | BARC-030359-06859 | 13 | 32171109 | F | 90.84 | 19 | 191 | A | 273 | G |
| SY0425AQ | | 13 | 34437456 | F | 92.55 | | | G | | A |
| SY0840AQ | | 18 | 60781120 | G | 127.05 | 334 | 335 | A | 336 | G |
| SY0474AQ | | 18 | 61162023 | G | 129.01 | 337 | 338 | G | 339 | A |
| SY0498AQ | BARC-032647-09003 | 12 | 36574820 | H | 91.92 | 15 | 33 | G | 51 | A |
| SY0499AQ | BARC-030421-06864 | 12 | 37684002 | H | 101.11 | 16 | 34 | G | 52 | A |
| SY0504AQ | BARC-025709-05013 | 12 | 39890002 | H | 117.61 | 17 | 35 | G | 53 | A |
| SY0622AQ | | 19 | 40201168 | L | 65.52 | 346 | 347 | A | 348 | C |
| SY0623AQ | | 19 | 41343324 | L | 69.09 | 352 | 353 | G | 354 | A |
| SY0673AQ | | 3 | 45098253 | N | 105.76 | 355 | 356 | A | 357 | C |
| SY0674AQ | | 3 | 45416367 | N | 110.61 | 358 | 359 | G | 360 | A |
| SY0928AQ | | 3 | 45597649 | N | 113.05 | 361 | 362 | A | 363 | G |

TABLE 2

Summary of genetic markers associated with IDC.

| Assay name | SNP name/ Locus name | Chromo- some | Physical osition in Williams82 genome | Linkage group | LG position (cM) | SEQ ID NO for DNA fragment comprising SNP | SEQ ID NO for Probe 1 sequence | Probe 1 detected nucleo- tide | SEQ ID NO for Probe 2 name | Probe 2 detected nucleo- tide |
|---|---|---|---|---|---|---|---|---|---|---|
| SY0152AQ | BARC -029149-06088 | 5 | 1035989 | A1 | 4.94 | 1 | 19 | G | 37 | A |
| SY0724AQ | BARC- 020033-04410 | 5 | 1305487 | A1 | 5.83 | 2 | 20 | G | 38 | A |
| SY1154AQ | BARC -015905-02012 | 5 | 1306354 | A1 | 5.84 | 3 | 21 | Insert | 39 | delete |

TABLE 2-continued

Summary of genetic markers associated with IDC.

| Assay name | SNP name/ Locus name | Chromo-some | Physical osition in Williams82 genome | Linkage group | LG position (cM) | SEQ ID NO for DNA fragment comprising SNP | SEQ ID NO for Probe 1 sequence | Probe 1 detected nucleo-tide | SEQ ID NO for Probe 2 name | Probe 2 detected nucleo-tide |
|---|---|---|---|---|---|---|---|---|---|---|
| SY0153AQ | BARC -024383-04865 | 5 | 1401213 | A1 | 6.15 | 4 | 22 | A | 40 | C |
| SY0224AQ | BARC -021353-04045 | 14 | 4305821 | B2 | 23.00 | 5 | 23 | T | 41 | A |
| SY0226AQ | BARC -039595-07515 | 14 | 5029071 | B2 | 26.97 | 6 | 24 | C | 42 | G |
| SY0781AQ | BARC-027478-06590 | 2 | 2850183 | D1b | 22.10 | 7 | 25 | A | 43 | G |
| SY0322AQ | BARC -028749-06007 | 2 | 3091839 | D1b | 22.70 | 8 | 26 | T | 44 | A |
| SY0325AQ | BARC -016063-02051 | 2 | 4545096 | D1b | 36.6 | 9 | 27 | A | 45 | G |
| SY0328AQ | BARC -040713-07825 | 2 | 8685663 | D1b | 54.83 | 10 | 28 | G | 46 | A |
| SY0369AQ | BARC -030579-06906 | 17 | 37973334 | D2 | 99.70 | 11 | 29 | A | 47 | G |
| SY0374AQ | BARC -016167-02298 | 17 | 40852374 | D2 | 133.00 | 12 | 30 | Insert | 48 | delete |
| SY0422AQ | BARC -029683-06315 | 13 | 29825175 | F | 80.96 | 13 | 31 | G | 49 | C |
| SY0425AQ | BAR -032717-09021 | 13 | 34437456 | F | 92.55 | 14 | 32 | G | 50 | A |
| SY0498AQ | BARC -032647 -09003 | 12 | 36574820 | H | 91.92 | 15 | 33 | G | 51 | A |
| SY0499AQ | BARC -030421-06864 | 12 | 37684002 | H | 101.11 | 16 | 34 | A | 52 | G |
| SY0504AQ | BARC -025709-05013 | 12 | 39890002 | H | 117.61 | 17 | 35 | G | 53 | A |
| SY0815AQ | BARC-031461-07098 | 13 | 28187977 | F | 75.78 | 18 | 36 | G | 54 | A |
| SY0723BQ | BARC-025589-06525 | 5 | 1221071 | A1 | 5.55 | 55 | 137 | G | 219 | A |
| SY0225AQ | BARC-031281-07037 | 14 | 5086314 | B2 | 23.48 | 56 | 138 | C | 220 | A |
| SY2190AQ | Solexa Variant 45958116 | 14 | 4943836 | B2 | 24.20 | 57 | 139 | A | 221 | G |
| SY0782AQ | BARC-020105-04465 | 2 | 3111353 | D1b | 22.59 | 58 | 140 | G | 222 | A |
| SY2783 | BARC-016063-02049 | 2 | 4544845 | D1b | 36.36 | 59 | 141 | C | 223 | A |
| SY2789 | BARC-016573-02145 | 2 | 4901498 | D1b | 39.08 | 60 | 142 | T | 224 | A |
| SY0326AQ | BARC-016573-02146 | 2 | 4901534 | D1b | 39.08 | 61 | 143 | A | 225 | G |
| SY1018AQ | BARC-045259-08916 | 2 | 5612835 | D1b | 42.95 | 62 | 144 | G | 226 | C |
| SY1553AQ | Solexa Variant 8489702 | 2 | 5770488 | D1b | 43.81 | 63 | 145 | C | 227 | A |
| SY1554AQ | Solexa Variant 1115728 | 2 | 5967462 | D1b | 44.88 | 64 | 146 | G | 228 | A |
| SY1556AQ | Solexa Variant 10115697 | 2 | 6277241 | D1b | 46.57 | 65 | 147 | A | 229 | C |
| SY1558AQ | Solexa Variant 13145772 | 2 | 6563655 | D1b | 48.13 | 66 | 148 | A | 230 | G |
| SY1559AQ | Solexa Variant 43421811 | 2 | 6750184 | D1b | 49.14 | 67 | 149 | A | 231 | G |
| SY1560AQ | Solexa Variant 5554913 | 2 | 6941554 | D1b | 50.18 | 68 | 150 | A | 232 | G |
| SY1561AQ | Solexa Variant 3592864 | 2 | 7103233 | D1b | 51.06 | 69 | 151 | A | 233 | G |
| SY0991AQ | BARC-028393-05860 | 2 | 7260411 | D1b | 51.92 | 70 | 152 | G | 234 | A |
| SY1303AQ | BARC-050325-09554 | 2 | 7266159 | D1b | 54.47 | 71 | 153 | A | 235 | G |
| SY1000AQ | BARC-014995-01945 | 2 | 7340691 | D1b | 54.53 | 72 | 154 | A | 236 | G |
| SY2802 | BARC-019149-03314 | 2 | 7472350 | D1b | 54.63 | 73 | 155 | C | 237 | A |
| SY0784AQ | BARC-019149-03315 | 2 | 7472790 | D1b | 54.63 | 74 | 156 | G | 238 | A |
| SY2529AQ | Solexa Variant 3088957 | 17 | 38197936 | D2 | 101.70 | 75 | 157 | A | 239 | G |
| SY2530AQ | Solexa Variant 798961 | 17 | 38249591 | D2 | 102.16 | 76 | 158 | G | 240 | A |
| SY2531AQ | Solexa Variant 799016 | 17 | 38366805 | D2 | 103.21 | 77 | 159 | G | 241 | C |
| SY2532AQ | Solexa Variant 3090170 | 17 | 38467762 | D2 | 104.11 | 78 | 160 | G | 242 | A |
| SY2534AQ | Solexa Variant 8398844 | 17 | 38645085 | D2 | 105.69 | 79 | 161 | G | 243 | A |
| SY0370AQ | BARC-013653-01222 | 17 | 38730132 | D2 | 106.45 | 80 | 162 | A | 244 | G |
| SY2535AQ | Solexa Variant 43757059 | 17 | 38838688 | D2 | 107.31 | 81 | 163 | C | 245 | G |
| SY2536AQ | Solexa Variant 10529459 | 17 | 38956483 | D2 | 108.23 | 82 | 164 | T | 246 | A |
| SY2537AQ | Solexa Variant 800459 | 17 | 39092231 | D2 | 109.30 | 83 | 165 | G | 247 | A |
| SY2538AQ | Solexa Variant 800598 | 17 | 39222387 | D2 | 110.33 | 84 | 166 | A | 248 | G |
| SY2539AQ | Solexa Variant 62025471 | 17 | 39350989 | D2 | 111.34 | 85 | 167 | A | 249 | G |
| SY1313AQ | BARC-011591-00299 | 17 | 39707504 | D2 | 114.15 | 86 | 168 | C | 250 | A |
| SY1432AQ | BARC-042475-08274 | 17 | 39925577 | D2 | 117.60 | 87 | 169 | G | 251 | A |
| SY2542AQ | Solexa Variant 802495 | 17 | 40019956 | D2 | 119.10 | 88 | 170 | G | 252 | A |
| SY2543AQ | Solexa Variant 802503 | 17 | 40033832 | D2 | 119.32 | 89 | 171 | G | 253 | A |
| SY2544AQ | Solexa Variant 3098371 | 17 | 40102736 | D2 | 120.41 | 90 | 172 | C | 254 | A |
| SY2545AQ | Solexa Variant 802638 | 17 | 40191230 | D2 | 121.81 | 91 | 173 | A | 255 | G |
| SY2546AQ | Solexa Variant 8400374 | 17 | 40266167 | D2 | 123.00 | 92 | 174 | A | 256 | G |
| SY2549AQ | Solexa Variant 3099616 | 17 | 40430393 | D2 | 125.60 | 93 | 175 | A | 257 | T |
| SY2550AQ | Solexa Variant 3099654 | 17 | 40477390 | D2 | 126.35 | 94 | 176 | A | 258 | G |
| SY2552AQ | Solexa Variant 8400643 | 17 | 40599087 | D2 | 128.27 | 95 | 177 | C | 259 | G |
| SY2553AQ | Solexa Variant 10531173 | 17 | 40685656 | D2 | 129.64 | 96 | 178 | C | 260 | A |
| SY2554AQ | Solexa Variant 3100774 | 17 | 40733711 | D2 | 130.41 | 97 | 179 | C | 261 | A |
| SY0372AQ | BARC-044655-08750 | 17 | 40774357 | D2 | 131.05 | 98 | 180 | T | 262 | A |
| SY2913 | BARC-029645-06278 | 17 | 40841974 | D2 | 132.15 | 99 | 181 | G | 263 | A |
| SY0373AQ | BARC-029645-06276 | 17 | 40842311 | D2 | 132.16 | 100 | 182 | A | 264 | G |
| SY2958 | BARC-029683-06313 | 13 | 29825335 | F | 80.96 | 101 | 183 | A | 265 | T |
| SY1091AQ | BARC-044829-08820 | 13 | 29702280 | F | 81.14 | 102 | 184 | A | 266 | G |
| SY2884 | BARC-044829-08813 | 13 | 29702177 | F | 81.14 | 103 | 185 | A | 267 | G |
| SY1258AQ | BARC-030899-06963 | 13 | 29310338 | F | 81.72 | 104 | 186 | A | 268 | G |
| SY1258Q | BARC-030899-06964 | 13 | 29310045 | F | 81.72 | 105 | 187 | G | 269 | C |
| SY1259AQ | BARC-041141-07915 | 13 | 30012841 | F | 83.25 | 106 | 188 | G | 270 | A |
| SY1259BQ | BARC-041141-07916 | 13 | 30012524 | F | 83.25 | 107 | 189 | G | 271 | A |
| SY0133A | BARC-030359-06858 | 13 | 32170760 | F | 90.84 | 108 | 190 | C | 272 | A |
| SY0424CQ | BARC-030359-06859 | 13 | 32171109 | F | 90.84 | 19 | 191 | A | 273 | G |
| SY2290AQ | Solexa Variant 8697430 | 12 | 36649158 | H | 94.63 | 109 | 192 | A | 274 | G |
| SY2292AQ | Solexa Variant 8287230 | 12 | 36702135 | H | 96.57 | 111 | 193 | A | 275 | G |

TABLE 2-continued

Summary of genetic markers associated with IDC.

| Assay name | SNP name/ Locus name | Chromo-some | Physical osition in Williams82 genome | Linkage group | LG position (cM) | SEQ ID NO for DNA fragment comprising SNP | SEQ ID NO for Probe 1 sequence | Probe 1 detected nucleo-tide | SEQ ID NO for Probe 2 name | Probe 2 detected nucleo-tide |
|---|---|---|---|---|---|---|---|---|---|---|
| SY2294AQ | Solexa Variant 6764969 | 12 | 36779864 | H | 99.40 | 112 | 194 | A | 276 | C |
| SY1229AQ | BARC-015079-02561 | 12 | 36780299 | H | 99.42 | 113 | 195 | G | 277 | A |
| SY2296AQ | Solexa Variant 7688926 | 12 | 37820942 | H | 102.96 | 114 | 196 | G | 278 | A |
| SY2300AQ | Solexa Variant 568862 | 12 | 38060977 | H | 106.11 | 115 | 197 | C | 279 | G |
| SY2301AQ | Solexa Variant 568998 | 12 | 38139852 | H | 107.58 | 116 | 198 | A | 280 | G |
| SY0500AQ | BARC-039237-07479 | 12 | 38202616 | H | 108.11 | 117 | 199 | A | 281 | G |
| SY0501AQ | BARC-029981-06767 | 12 | 38340395 | H | 109.77 | 118 | 200 | A | 282 | C |
| SY2303AQ | Solexa Variant 570546 | 12 | 38706235 | H | 112.08 | 119 | 201 | A | 283 | G |
| SY2306AQ | Solexa Variant 32481323 | 12 | 39284935 | H | 115.74 | 120 | 202 | A | 284 | G |
| SY1333AQ | BARC-062843-18117 | 12 | 39824427 | H | 115.85 | 121 | 203 | G | 285 | C |
| SY2307AQ | Solexa Variant 41487777 | 12 | 39447867 | H | 116.77 | 122 | 204 | A | 286 | G |
| SY2308AQ | Solexa Variant 7693159 | 12 | 39641559 | H | 117.17 | 123 | 205 | A | 287 | G |
| SY0503AQ | BARC-027816-06683 | 12 | 38676052 | H | 117.58 | 124 | 206 | G | 288 | A |
| SY0078AQ | BARC-022043-04271 | 13 | 28329680 | F | 76.72 | 125 | 207 | A | 289 | G |
| SY0816AQ | BARC-022043-04271 | 13 | 28329680 | F | 76.72 | 126 | 208 | A | 290 | G |
| SY2730AQ | | 13 | 28451936 | F | 77.49 | 127 | 209 | A | 291 | G |
| SY2732AQ | | 13 | 28543769 | F | 78.06 | 128 | 210 | C | 292 | A |
| SY2733AQ | | 13 | 28544253 | F | 78.06 | 129 | 211 | G | 293 | A |
| SY0079AQ | BARC-029823-06424 | 13 | 28634881 | F | 78.63 | 130 | 212 | C | 294 | G |
| SY0420BQ | BARC-029823-06438 | 13 | 28635076 | F | 78.63 | 131 | 213 | T | 295 | T |
| SY0079BQ | BARC-029823-06439 | 13 | 28635101 | F | 78.63 | 132 | 214 | C | 296 | A |
| SY2743AQ | | 13 | 29223877 | F | 79.1 | 133 | 215 | A | 297 | T |
| SY2741AQ | | 13 | 29223891 | F | 78.79 | 134 | 216 | A | 298 | G |
| SY2742AQ | | 13 | 29223895 | F | 78.95 | 135 | 217 | A | 299 | A |
| SY0132AQ | BARC-029683-06319 | 13 | 29825027 | F | 80.56 | 136 | 218 | A | 300 | c |
| SY1076AQ | | 6 | 3533016 | C2 | 32.70 | 302 | 324 | A | 346 | C |
| SY0271AQ | | 6 | 3369861 | C2 | 36.69 | 303 | 325 | A | 347 | G |
| SY0307AQ | | 1 | 49210095 | D1a | 72.72 | 304 | 326 | A | 348 | T |
| SY1300AQ | | 2 | 4189924 | D1b | 33.99 | 305 | 327 | C | 349 | A |
| SY0386AQ | | 15 | 5897794 | E | 31.99 | 306 | 328 | A | 350 | G |
| SY0399AQ | | 15 | 24823131 | E | 94.73 | 307 | 329 | A | 351 | G |
| SY0840AQ | | 18 | 60781120 | G | 127.05 | 308 | 330 | A | 352 | G |
| SY0474AQ | | 18 | 61162023 | G | 129.01 | 309 | 331 | G | 353 | A |
| SY2045AQ | | 9 | 38695948 | K | 69.90 | 310 | 332 | G | 354 | A |
| SY0622AQ | | 19 | 40201168 | L | 65.52 | 311 | 333 | A | 355 | C |
| SY0623AQ | | 19 | 41343324 | L | 69.09 | 312 | 334 | G | 356 | A |
| SY0673AQ | | 3 | 45098253 | N | 105.76 | 313 | 335 | A | 357 | C |
| SY0674AQ | | 3 | 45416367 | N | 110.61 | 314 | 336 | G | 358 | A |
| SY0928AQ | | 3 | 45597649 | N | 113.05 | 315 | 337 | A | 359 | G |
| SY2140AQ | | 10 | 44378814 | O | 116.87 | 316 | 338 | A | 360 | G |
| SY0121AQ | | 14 | 1359785 | B2 | 7.04 | 317 | 339 | A | 361 | C |
| SY0122AQ | | 14 | 1949216 | B2 | 8.15 | 318 | 340 | A | 362 | T |
| SY0778AQ | | 1 | 50885379 | D1a | 93.69 | 319 | 341 | A | 363 | G |
| SY0952AQ | | 15 | 7030013 | E | 33.92 | 320 | 342 | G | 364 | A |
| SY0808AQ | | 15 | 32474587 | E | 95.92 | 321 | 343 | A | 365 | G |
| SY1069AQ | | 9 | 40300598 | K | 75.67 | 322 | 344 | G | 366 | A |
| SY0066AQ | | 19 | 40774016 | L | 67.31 | 323 | 345 | A | 367 | G |

In some embodiments, any one of the marker allele(s) associated with iron deficiency chlorosis are as set forth in Table 2 may be used to identify, select or produce a plant having tolerance to iron deficiency chlorosis. In some embodiments any combination of two or more marker alleles as set forth in Table 2 could be used to identify, select or produce a plant having tolerance to iron deficiency chlorosis In some embodiments of this invention, the marker allele (s) associated with iron deficiency chlorosis as set forth in Table 2 can be located in one or more of the following chromosomal intervals: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; (k) a chromosomal interval on chromosome 17 defined by and including a G allele at SY0370AQ and a G allele at SY0373AQ; (l) a chromosomal interval on chromosome 17 defined by and including an A allele at SY1313AQ and a T allele at SY0372AQ; (m) a chromosomal interval on chromosome 2 defined by and including an A allele at SY0326AQ and a G allele at SY0784AQ; (n) a chromosomal interval on chromosome 13 defined by and including a G allele at SY1259AQ and an A allele at SY0424CQ; (o) a chromosomal interval on chromosome 13 defined by and including an A allele at SY0078AQ and a C allele at SY0132AQ; (p) a chromosomal interval on chromosome 13 defined by and including an A allele at SY0078AQ and an A allele at SY0132AQ; (q) a chromosomal interval on chromosome 13 defined by and including an A allele at SY0816AQ and a C allele at SY0079AQ; (r) a chromosomal interval on chromosome 13 defined by and including an A allele at SY0816AQ and a G allele at SY0079AQ; or any combination thereof.

As would be understood by one of skill in the art, additional chromosomal intervals can be defined by the SNP markers provided herein in Table 2.

In other embodiments, a combination of genetic markers of this invention as set forth in Table 2 (haplotype) is associated with iron deficiency chlorosis, the combination of genetic markers selected from the group consisting of: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, and any combination thereof; (h) a G allele at SY0369AQ, a G allele at SY0370AQ, a T allele at SY0372AQ, a G allele at SY0373AQ, an insertion of nucleotide sequence CTTACC at SY0374AQ, and any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, and any combination thereof; (l) a G allele at SY0499AQ, an A allele at SY0500AQ, an A allele at SY0501AQ, a G allele at SY0503AQ, a G allele at SY1333AQ, an A allele at SY0504AQ, and any combination thereof; (m) a T allele at SY0224AQ, a C allele at SY0225AQ, a C allele at SY0226AQ, and any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, and any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, and any combination thereof; (p) a G allele at SY0422AQ, an A allele at SY1091AQ, a C allele at SY0133AQ, a G allele at SY0425AQ, and any combination thereof; (q) a C allele at SY0422AQ, a G allele at SY1091AQ, a G allele at SY1258AQ, a G allele at SY1259AQ, an A allele at SY0424CQ, an A allele at SY0425AQ, and any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, and any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, and any combination thereof; and (w) any combination of (a) through (v) above.

Accordingly, this invention further provides methods of identifying, selection, and/or producing an iron deficiency chlorosis (IDC) tolerant soybean plant or part thereof, comprising: detecting, in said soybean plant or part thereof, the presence of a combination of genetic markers associated with IDC tolerance in a soybean plant, as described herein.

In further embodiments, the marker can comprise, consist essentially of or consist of any marker linked to the aforementioned markers. That is, any genetic marker that is in linkage disequilibrium with any of the aforementioned markers (SNPs, chromosome intervals and/or combinations of markers (haplotypes)) may also be used to identify, select and/or produce a soybean plant having IDC tolerance. Linked markers may be determined, for example, by using resources available on the SoyBase website (www.soybase.org).

The present invention further provides that the detecting of a molecular marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of an SNP, for example as those SNP allele markers identified in Table 2. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (i.e., has a homology of in some embodiments more than 80%, in some embodiments more than 90%, in some embodiments more than 95%, in some embodiments more than 97%, and in some embodiments more than 98% or 99%) to the expected sequence based on the sequence of the marker associated with that SNP in the plant in which the marker was first detected.

The detection of an amplified DNA fragment having the predicted length or the predicted nucleic acid sequence can be performed by any of a number or techniques, including, but not limited to, standard gel-electrophoresis techniques or by using automated DNA sequencers. These methods are not described here in detail as they are well known to those of ordinary skill in the art, although exemplary approaches are set forth in the Examples.

As shown in Table 2, the SNP markers of this invention are associated with IDC tolerance. In some embodiments, as described herein, one marker or a combination of markers can be used to detect the presence of an IDC tolerant plant. In some embodiments, a marker can be located within a chromosomal interval (QTL) or be present in the genome of the plant as a haplotype as defined herein.

Thus, methods for identifying and/or selecting a soybean plant or germplasm comprising IDC tolerance comprise detecting the presence of a genetic marker (e.g., SNP, SNP located in chromosomal interval (QTL) and/or combination of SNPs) associated with IDC tolerance in a soybean plant or part thereof. Thus, the genetic marker can be detected in any sample taken from the soybean plant or from a soybean germplasm, including, but not limited to, the whole plant or germplasm or any part thereof (e.g., a seed, a leaf, a tissue culture, a cell, etc.).

Accordingly, in one aspect of the present invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein said marker is located within a chromosomal interval comprising, consisting essentially of, or consisting of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; or (k) any combination of (a) through (j) above, thereby identifying and/or selecting an IDC tolerant soybean plant or part thereof.

In some embodiments of the present invention, a method of identifying and/or selecting an iron deficiency chlorosis (IDC) tolerant soybean plant or part thereof is provided, the method comprising: detecting, in said soybean plant or part thereof, the presence of a combination of genetic markers (haplotype) associated with IDC tolerance in a soybean plant, the combination of genetic markers comprises, consists essentially of, or consists of: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, or any combination thereof; (h) a G allele at SY0369AQ, a G allele at SY0370AQ, a T allele at SY0372AQ, a G allele at SY0373AQ, an insertion of nucleotide sequence CTTACC at SY0374AQ, or any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, or any combination thereof; (l) a G allele at SY0499AQ, an A allele at SY0500AQ, an A allele at SY0501AQ, a G allele at SY0503AQ, a G allele at SY1333AQ, an A allele at SY0504AQ, or any combination thereof; (m) a T allele at SY0224AQ, a C allele at SY0225AQ, a C allele at SY0226AQ, or any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, or any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, or any combination thereof; (p) a G allele at SY0422AQ, an A allele at SY1091AQ, a C allele at SY0133AQ, a G allele at SY0425AQ, or any combination thereof; (q) a C allele at SY0422AQ, a G allele at SY1091AQ, a G allele at SY1258AQ, a G allele at SY1259AQ, an A allele at SY0424CQ, an A allele at SY0425AQ, or any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, or any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, or any combination thereof; or (w) any combination of (a) through (v) above, thereby identifying and/or selecting an IDC tolerant soybean plant or part thereof.

In another embodiment, the present invention provides a method of identifying and/or selecting an iron deficiency chlorosis (IDC) tolerant soybean plant or part thereof, comprising: detecting, in said soybean plant or part thereof, the presence of a marker associated with IDC tolerance, wherein said marker comprises, consists essentially of, or consists of: (a) a G allele at SY0152AQ; (b) a G allele at SY0724AQ; (c) an insertion of nucleotide sequence CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ, (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an A allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; or any combination of (a) through (gg) above, thereby identifying and/or selecting an IDC tolerant soybean plant or part thereof.

In another aspect of the invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as reduced yellow flash symptoms, and the marker is associated with reduced yellow flash symptoms in a soybean plant and is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; or (g) any combination of (a) through (f) above, thereby identifying and/or selecting an IDC tolerant soybean plant or part thereof.

In other embodiments of this invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as reduced yellow flash symptoms, and the marker is associated with reduced yellow flash symptoms in a soybean plant and comprises: (a) a G allele at SY0152AQ; (b) a G allele at SY0724AQ; (c) an insertion of nucleotide sequence CACACCTAGCTAAT (SEQ ID NO:301) at SY1154AQ; (e) an A allele at SY0153AQ; (f) an A allele at SY0781AQ; (g) a T allele at SY0322AQ; (h) a G allele at SY0370AQ; (i) a T allele at SY0372AQ; (j) a G allele at SY0373AQ; (k) a insertion of GGTAAG at SY0374AQ; (l) an A allele at SY0500AQ; (m) an A allele at SY0501AQ; (n) a G allele at SY0503AQ; (o) a G allele at SY0504AQ; (p) a G allele at SY0504AQ; or (q) any combination of (a) through (p) above, thereby identifying and/or selecting an IDC tolerant soybean plant or part thereof.

In a further aspect, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant and is located within a chromosomal interval of: (a) a chromosomal interval on chromosome 5 defined by and including a G allele at SY0152AQ and a G allele at SY0724AQ; (b) a chromosomal interval on chromosome 14 defined by and including a T allele at SY0224AQ and a C allele at SY0226AQ; (c) a chromosomal interval on chromosome 2 defined by and including (i) an A allele at SY0325AQ and a G allele at SY0328AQ or (ii) a G allele at SY0325AQ and a G allele at SY0328AQ; (d) a chromosomal interval on chromosome 13 defined by and including (i) a G allele at SY0422AQ and a G allele at SY0425AQ or (ii) a C allele at SY0422AQ and an A allele at SY0425AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 13 defined by and including an A allele at SY0815AQ and a G allele at SY0422AQ or (g) any combination of (a) through (f) above, thereby identifying and/or selecting an IDC tolerant soybean plant or part thereof.

In a further aspect, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant and is located within a chromosomal interval of as indicated by any combination of one or more SNP markers as indicated in Table 2.

The present invention additionally provides a method of identifying and/or selecting an iron deficiency chlorosis (IDC) tolerant soybean plant or part thereof, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant and comprises: (a) a G allele at SY0152AQ; (b) a G allele at SY0724AQ; (c) a T allele at SY0224AQ; (d) a C allele at SY0225AQ; (e) a C allele at SY0226AQ; (f) an A allele at SY0326AQ; (g) a C allele at SY1018AQ; (h) an A allele at SY0991AQ; (i) an A allele at SY1000AQ; (j) a G allele at SY0784AQ; (k) a G allele at SY0328AQ; (l) an A allele at SY0815AQ; (m) an A allele at SY0078AQ; (n) a C allele at SY0132AQ; (o) an A allele at SY0816AQ; (p) a C allele at SY0079AQ; (q) an A allele at SY0079BQ; (r) a T allele at SY0420BQ; or (s) any combination of (a) through (r) above, thereby identifying and/or selecting an IDC tolerant soybean plant or part thereof.

Another embodiment of the invention comprises the use of one or more markers to identify, select or create a soybean plant that are tolerant or nontolerant (listed respectfully "tolerant allele or intolerant allele) to IDC the one or more markers selected from the group consisting of the following alleles: (a) a G or A allele at SY0152AQ; (b) a G or A allele at SY0724AQ; (c) a nucleotide insertion comprising CACACCTAGCTAAT or deletion of said nucleotide at SY1154AQ; (d) a A or C allele at SY0153AQ; (e) a A or C allele at SY0121AQ; (f) a A or T allele at SY0122AQ; (g) a T or A allele at SY0224AQ; (h) a C or G allele at SY0226AQ; (i) a A or C allele at SY1076AQ; (j) a A or G allele at SY0271AQ; (k) a A or T allele at SY0307AQ; (l) a A or G allele at SY0778AQ; (m) a G or A allele at SY0781AQ; (n) a T or A allele in SY0322AQ; (o) a C or A allele at SY1300AQ; (p) a A or G allele at SY0325AQ; (q) a G or A allele at SY0328AQ; (r) a A or G allele at SY0369AQ; (s) a G or A allele at SY2537AQ; (t) a T or A allele at SY2549AQ; (u) a A or G allele at SY0386AQ; (v) a G or A allele at SY0952AQ; (w) a A or G allele at SY0399AQ; (x) a A or G allele at SY0399AQ; (y) a A or G allele at SY0808AQ; (z) a G or C allele at SY0422AQ; (aa) a A or G allele at SY1258AQ; (bb) a G or A allele at SY0424CQ; (cc) a G or A allele at SY0425AQ; (dd) a A or G allele at SY0840AQ; (ee) a G or A allele at SY0474AQ; (ff) a G or A allele at SY0498AQ; (gg) a A or G allele at SY0499AQ; (hh) a G or A allele at SY0504AQ; (ii) a G or A allele at SY2045AQ; (jj) a G or A allele at SY1069AQ; (kk) a A or C allele at SY0622AQ; (ll) a A or G allele at SY0066AQ; (mm) a G or A allele at SY0623AQ; (nn) a A or C allele at SY0673AQ; (oo) a A or C allele at SY0673AQ; (pp) a G or A allele at SY0674AQ; (qq) a A or G allele at SY0928AQ; and (rr) a A or G allele at SY2140AQ.

In another aspect of the invention a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as reduced yellow flash and recovery from yellow flash, and the marker is associated with reduced yellow flash and recovery from yellow flash in a soybean plant and is located within a chromosomal interval of: (a) a chromosomal interval on chromosome 5 defined by and including a G allele at SY0152AQ and a G allele at SY0724AQ; (b) a chromosomal interval on chromosome 12 defined by and including (i) a G allele at SY0498AQ and an A allele at SY0499AQ or (ii) an A allele at SY0498AQ and a G allele at SY0499AQ; or (c) any combination of (a) and/or (b) above, thereby identifying and/or selecting an IDC tolerant soybean plant or part thereof.

In one embodiment, one may select for IDC markers within specific regions of the Soybean genome these regions comprise (+/−10-20 nucleotides from each relative position within said interval) (a) a chromosomal interval consisting of positions 4.94 to 6.15 on Soybean chromosome 5; (b) a chromosomal interval consisting of positions 7.04-26.97 on Soybean chromosome 14; (c) a chromosomal interval consisting of positions 32.70-36.69 on Soybean chromosome 6; (d) a chromosomal interval consisting of positions 72.72 or 93.69 on Soybean chromosome 1; (e) a chromosomal interval consisting of positions 22.10-54.83 on Soybean chromosome 2; (f) a chromosomal interval consisting of positions 99.70-132.16 on Soybean chromosome 17; (g) a chromosomal interval consisting of positions 31.99-95.92 on Soybean chromosome 15; (h) a chromosomal interval consisting of positions 77.49-92.55 on Soybean chromosome 13; (i) a chromosomal interval consisting of positions 127.05-129.01 on Soybean chromosome 18; (j) a chromosomal interval consisting of positions 91.92-117.61 on Soybean chromosome 12; (k) a chromosomal interval consisting of positions 69.90-75.67 on Soybean chromosome 9; (l) a chromosomal interval consisting of positions 65.52-69.09 on Soybean chromosome 19; (m) a chromosomal interval consisting of positions 105.76-113.05 on Soybean chromosome 3; (n) a chromosomal interval consisting of position 116.87 on Soybean chromosome 10 and (o) any combination of markers selected from the chromosome intervals as stated in (a)-(n) above.

The present invention further provides a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as reduced yellow flash and recovery from yellow flash, and the marker is associated with reduced yellow flash and recovery from yellow flash in a soybean plant and comprises: (a) a G allele at SY0152AQ; (b) a G allele at SY0724AQ; or (c) any combination of (a) and/or (b) above, thereby identifying and/or selecting an IDC tolerant soybean plant or part thereof.

As described herein, methods for identifying and/or selecting a soybean plant or germplasm having IDC tolerance can comprise detecting the presence of a marker or a combination of markers associated with IDC tolerance. Any combination of the genetic markers of this invention can be used to identify and/or select a soybean plant or germplasm having IDC tolerance.

As described herein, in some aspects of this invention, the reduced yellow flash symptoms and/or recovery from yellow flash are exhibited by the soybean plant when the soybean plant is grown in calcareous soil having a pH greater than 7.5 and the marker is associated with reduced yellow flash symptoms and/or recovery from yellow flash in a soybean plant when the soybean plant is grown in calcareous soil having a pH greater than 7.5.

Accordingly, some embodiments of the present invention provide a method of identifying and/or selecting an iron deficiency chlorosis (IDC) tolerant soybean plant, wherein the IDC tolerance is exhibited as reduced yellow flash symptoms and/or recovery from yellow flash when the plant is grown calcareous soil having a pH greater than 7.5, and the marker (e.g., SNP allele, combination of SNP alleles and/or SNP allele located in a chromosome interval) is associated with reduced yellow flash symptoms and/or recovery from yellow flash in a soybean plant grown in calcareous soil having a pH greater than 7.5.

Marker-Assisted Selection

The subject matter disclosed herein also relates to methods for producing IDC tolerant soybean plants comprising detecting the presence of an allele associated with IDC tolerance in a donor soybean plant according to the methods as described herein and transferring a nucleic acid sequence comprising at least one allele thus detected from the donor plant to an IDC intolerant recipient soybean plant. The transfer of the nucleic acid sequence can be performed by any of the methods described herein.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding. It is also understood by those skilled in the art that it is of equal value to be able to select for plants that are not tolerant to IDC in for example, a Soybean plant breeding program.

The presently disclosed subject matter thus also provides methods for selecting a plant of the genus *Glycine* exhibiting tolerance to iron deficiency chlorosis (IDC) comprising detecting in the plant the presence of one or more genetic markers associated with IDC tolerance as defined herein. In an exemplary embodiment of the presently disclosed methods for selecting such a plant, the method comprises providing a sample of genomic DNA from a soybean plant; and (b) detecting in the sample of genomic DNA at least one genetic marker associated with IDC tolerance. In some embodiments, the detecting can comprise detecting one or more SNPs, a combination of SNPs (haplotype), and/or SNPs located in chromosomal intervals that are associated with IDC tolerance.

The providing of a sample of genomic DNA from a soybean plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. In exemplary embodiments of this invention, the nucleotide sequences comprising the genetic markers (SNPs) and probes for the detection of respective markers are provided in Table 2.

In some embodiments of this invention, a method is provided, said method comprising the transfer by introgression of the nucleic acid sequence from an IDC tolerant donor soybean plant into an IDC intolerant recipient soybean plant by crossing the plants. This transfer can be accomplished by using traditional breeding techniques. IDC tolerant loci are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode for the desired trait. As disclosed herein, such identification and selection is based on selection of one or more SNP alleles of this invention or markers associated therewith. MAB can also be used to develop near-isogenic lines (NIL) harboring one or more IDC tolerance alleles of interest, allowing a more detailed study of an effect of such allele(s), and is also an effective method for development of backcross inbred line (BIL) populations. Soybean plants developed according to these embodiments can in some embodiments derive a majority of their traits from the recipient plant and derive IDC tolerance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with IDC tolerance into an IDC intolerant recipient soybean plant. For example, inbred IDC tolerant soybean plant lines can be developed using the techniques of recurrent selection and backcrossing, selfing, and/or dihaploids, or any other technique used to make parental lines. In a method of recurrent selection and backcrossing, IDC tolerance can be introgressed into a target recipient plant (the recurrent parent) by crossing the recurrent parent with a first donor plant, which differs from the recurrent parent and is referred to herein as the "non-recurrent parent." The recurrent parent is a plant that is IDC intolerant or has a low level of IDC tolerance and, in some embodiments, possesses commercially desirable characteristics, such as, but not limited to disease and/or insect resistance, valuable nutritional characteristics, valuable abiotic stress tolerance (including, but not limited to, drought tolerance, salt tolerance), and the like. In some embodiments, the non-recurrent parent exhibits IDC tolerance and comprises a nucleic acid sequence that is associated with IDC tolerance. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence associated with IDC tolerance. Also, MAB can be used to confirm the results obtained from the quantitative bioassays. In some embodiments, the markers defined herein are suitable to select proper offspring plants by genotypic screening.

Following screening, the F1 hybrid plants that exhibit an IDC tolerance phenotype or, in some embodiments, the genotype, and thus comprise the requisite nucleic acid sequence associated with IDC tolerance, can be then selected and backcrossed to the recurrent parent for one or more generations in order to allow for the soybean plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant plant with the target segment from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase website (www.soybase.org).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with IDC tolerance. Thus, in some embodiments, the present invention relates to methods for producing soybean plants having an IDC tolerance associated allele comprising detecting the presence of at least one allele associated with IDC tolerance in a donor soybean plant as described herein, crossing the donor soybean plant with a second soybean plant or germplasm, and detecting in the progeny plant(s) the presence of said at least one allele, thereby transferring the at least one allele thus detected from the donor plant to the second soybean plant and thus producing a soybean plant having IDC tolerance. In some embodiments, the second plant is IDC intolerant. The transfer of the allele can be performed by any of the methods described herein.

Embodiments of the invention provides a method of identifying, selecting or producing an iron deficiency chlorosis (IDC) tolerant soybean plant through any one or a combination of the markers as set forth in Table 2.

In some embodiments of the present invention, a method of producing an iron deficiency chlorosis (IDC) tolerant soybean plant is provided, the method comprising: detecting, in a soybean germplasm, the presence of a marker associated with IDC tolerance in a soybean plant, wherein said marker is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; or (k) any combination of (a) through (j) above, and producing a soybean plant from said soybean germplasm, thereby producing an IDC tolerant soybean plant.

In other embodiments, the method of producing comprises detecting, in a soybean germplasm, the presence of a marker associated with IDC tolerance in a soybean plant, wherein said marker comprises: (a) a G allele at SY0152AQ; (b) a G allele at SY0724AQ; (c) an insertion of nucleotide sequence CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ, (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; or any combination of (a) through (gg) above.

In other embodiments, the method of producing comprises detecting, in a soybean germplasm, the presence of a combination of markers associated with IDC tolerance in a soybean plant, wherein said combination of markers comprises: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, or any combination thereof; (h) a G allele at SY0369AQ, a G allele at SY0370AQ, a T allele at SY0372AQ, a G allele at SY0373AQ, an insertion of nucleotide sequence CTTACC at SY0374AQ, or any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, or any combination thereof; (l) a G allele at SY0499AQ, an A allele at SY0500AQ, an A allele at SY0501AQ, a G allele at SY0503AQ, a G allele at SY1333AQ, an A allele at SY0504AQ, or any combination thereof; (m) a T allele at SY0224AQ, a C allele at SY0225AQ, a C allele at SY0226AQ, or any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, or any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, or any combination thereof; (p) a G allele at SY0422AQ, an A allele at SY1091AQ, a C allele at SY0133AQ, a G allele at SY0425AQ, or any combination thereof; (q) a C allele at SY0422AQ, a G allele at SY1091AQ, a G allele at SY1258AQ, a G allele at SY1259AQ, an A allele at SY0424CQ, an A allele at SY0425AQ, or any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, or any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, or any combination thereof; or (w) any combination of (a) through (v) above.

In further embodiments, the present invention provides a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as reduced yellow flash symptoms, and the marker is associated with reduced yellow flash symptoms in a soybean plant and is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; or (g) any combination of (a) through (f) above, and producing a soybean plant from said soybean germplasm, thereby producing an IDC tolerant soybean plant.

Additional embodiments of the invention provide a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as recovery from yellow flash, and the marker is associated with recovery from yellow flash in a soybean plant and is located within a chromosomal interval of: (a) a chromosomal interval on chromosome 5 defined by and including a G allele at SY0152AQ and a G allele at SY0724AQ; (b) a chromosomal interval on chromosome 14 defined by and including a T allele at SY0224AQ and a C allele at SY0226AQ; (c) a chromosomal interval on chromosome 2 defined by and including (i) an A allele at SY0325AQ and a G allele at SY0328AQ or (ii) a G allele at SY0325AQ and a G allele at SY0328AQ; (d) a chromosomal interval on chromosome 13 defined by and including (i) a G allele at SY0422AQ and a G allele at SY0425AQ or (ii) a C allele at SY0422AQ and an A allele at SY0425AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 13 defined by and including an A allele at SY0815AQ and a G allele at SY0422AQ or (g) any combination of (a) through (f) above, and producing a soybean plant from said soybean germplasm, thereby producing an IDC tolerant soybean plant.

Additional embodiments of the invention provide a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as reduced yellow flash symptoms and recovery from yellow flash, and the marker is associated with reduced yellow flash symptoms and recovery from yellow flash in a soybean plant and is located within a chromosomal interval of: (a) a chromosomal interval on chromosome 5 defined by and including a G allele at SY0152AQ and a G allele at SY0724AQ; (b) a chromosomal interval on chromosome 12 defined by and including (i) a G allele at SY0498AQ and an A allele at SY0499AQ or (ii) an A allele at SY0498AQ and a G allele at SY0499AQ; or (c) any combination of (a) and/or (b) above, and producing a soybean plant from said soybean germplasm, thereby producing an IDC tolerant soybean plant.

In other embodiments, the present invention provides a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as reduced yellow flash symptoms, and the marker is associated with reduced yellow flash symptoms in a soybean plant and comprises: (a) a G allele at SY0152AQ; (b) a G allele at SY0724AQ; (c) an insertion of nucleotide sequence CACACCTAGCTAAT (SEQ ID NO:301) at SY1154AQ; (e) an A allele at SY0153AQ; (f) an A allele at SY0781AQ; (g) a T allele at SY0322AQ; (h) a G allele at SY0370AQ; (i) a T allele at SY0372AQ; (j) a G allele at SY0373AQ; (k) a insertion of GGTAAG at SY0374AQ; (l) an A allele at SY0500AQ; (m) an A allele at SY0501AQ; (n) a G allele at SY0503AQ; (o) a G allele at SY0504AQ; (p) a G allele at SY0504AQ; or (q) any combination of (a) through (p) above, and producing a soybean plant from said soybean germplasm, thereby producing an IDC tolerant soybean plant.

Additional embodiments of the invention provide a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as recovery from yellow flash, and the marker is associated with recovery from yellow flash in a soybean plant and comprises: (a) a G allele at SY0152AQ; (b) a G allele at SY0724AQ; (c) a T allele at SY0224AQ; (d) a C allele at SY0225AQ; (e) a C allele at SY0226AQ; (f) an A allele at SY0326AQ; (g) a C allele at SY1018AQ; (h) an A allele at SY0991AQ; (i) an A allele at SY1000AQ; (j) a G allele at SY0784AQ; (k) a G allele at SY0328AQ; (l) an A allele at SY0815AQ; (m) an A allele at SY0078AQ; (n) a C allele at SY0132AQ; (o) an A allele at SY0816AQ; (p) a C allele at SY0079AQ; (q) an A allele at SY0079BQ; (r) a T allele at SY0420BQ; or (s) any combination of (a) through (r) above, and producing a soybean plant from said soybean germplasm, thereby producing an IDC tolerant soybean plant.

Further embodiments of the invention provide a method of producing an iron deficiency chlorosis (IDC) tolerant soybean plant, comprising: detecting, in a soybean germplasm, the presence of a marker associated with IDC tolerance in a soybean plant, wherein the IDC tolerance is exhibited as reduced yellow flash symptoms and recovery from yellow flash, and the marker is associated with reduced yellow flash symptoms and recovery from yellow flash in a soybean plant and comprises: (a) a G allele at SY0152AQ; (b) a G allele at SY0724AQ; or (c) any combination of (a) and/or (b) above, and producing a soybean plant from said soybean germplasm, thereby producing an IDC tolerant soybean plant.

Additionally, provided herein is a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, wherein said marker is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; or (k) any combination of (a) through (j) above, and selecting a progeny soybean plant or germplasm that possesses said marker within its genome, thereby selecting an IDC tolerant soybean plant or germplasm.

Additionally, provided herein is a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a combination of markers associated with IDC tolerance in a soybean plant, wherein said combination of markers comprises: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, or any combination thereof; (h) a G allele at SY0369AQ, a G allele at SY0370AQ, a T allele at SY0372AQ, a G allele at SY0373AQ, an insertion of nucleotide sequence CTTACC at SY0374AQ, or any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, or any combination thereof; (l) a G allele at SY0499AQ, an A allele at SY0500AQ, an A allele at SY0501AQ, a G allele at SY0503AQ, a G allele at SY1333AQ, an A allele at SY0504AQ, or any combination thereof; (m) a T allele at SY0224AQ, a C allele at SY0225AQ, a C allele at SY0226AQ, or any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, or any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, or any combination thereof; (p) a G allele at SY0422AQ, an A allele at SY1091AQ, a C allele at SY0133AQ, a G allele at SY0425AQ, or any combination thereof; (q) a C allele at SY0422AQ, a G allele at SY1091AQ, a G allele at SY1258AQ, a G allele at SY1259AQ, an A allele at SY0424CQ, an A allele at SY0425AQ, or any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, or any combination thereof; (v) an A allele at SY0815AQ, an A allele at SY0078AQ, an A allele at SY0132AQ, an A allele at SY0816AQ, a G allele at SY0079AQ, an A allele at SY0079BQ, a G allele at SY0420BQ, a G allele at SY0422AQ, or any combination thereof; or (w) any combination of (a) through (v) above, and selecting a progeny soybean plant or germplasm that possesses said marker within its genome, thereby selecting an IDC tolerant soybean plant or germplasm.

Further embodiments of the invention provide a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, wherein said marker comprises: (a) a G allele at SY0152AQ; (b) a G allele at SY0724AQ; (c) an insertion of nucleotide sequence CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ, (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; or any combination of (a) through (gg) above, and selecting a progeny soybean plant or germplasm that possesses said marker within its genome, thereby selecting an IDC tolerant soybean plant or germplasm.

In other embodiments, the present invention provides a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, further wherein the IDC tolerance is exhibited as reduced yellow flash symptoms, and said marker is associated with reduced yellow flash symptoms in a soybean plant and is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; or (g) any combination of (a) through (f) above, and selecting a progeny soybean plant or germplasm that possesses said marker within its genome, thereby selecting an IDC tolerant soybean plant or germplasm.

One embodiment of the invention is the use of at least one marker from Table 2 associated with IDC in a soybean plant breeding program.

In further embodiments, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, further wherein the IDC tolerance is exhibited as recovery from yellow flash, and said marker is associated with recovery from yellow flash in a soybean plant and is located within a chromosomal interval of: (a) a chromosomal interval on chromosome 5 defined by and including a G allele at SY0152AQ and a G allele at SY0724AQ; (b) a chromosomal interval on chromosome 14 defined by and including a T allele at SY0224AQ and a C allele at SY0226AQ; (c) a chromosomal interval on chromosome 2 defined by and including (i) an A allele at SY0325AQ and a G allele at SY0328AQ or (ii) a G allele at SY0325AQ and a G allele at SY0328AQ; (d) a chromosomal interval on chromosome 13 defined by and including (i) a G allele at SY0422AQ and a G allele at SY0425AQ or (ii) a C allele at SY0422AQ and an A allele at SY0425AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 13 defined by and including an A allele at SY0815AQ and a G allele at SY0422AQ or (g) any combination of (a) through (f) above, and selecting a progeny soybean plant or germplasm that possesses said marker within its genome, thereby selecting an IDC tolerant soybean plant or germplasm.

In further embodiments, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, further wherein the IDC tolerance is exhibited as reduced yellow flash symptoms and recovery from yellow flash, and said marker is associated with reduced yellow flash symptoms and recovery from yellow flash in a soybean plant is located within a chromosomal interval of: (a) a chromosomal interval on chromosome 5 defined by and including a G allele at SY0152AQ and a G allele at SY0724AQ; (b) a chromosomal interval on chromosome 12 defined by and including (i) a G allele at SY0498AQ and an A allele at SY0499AQ or (ii) an A allele at SY0498AQ and a G allele at SY0499AQ; or (c) any combination of (a) and/or (b) above, and selecting a progeny soybean plant or germplasm that possesses said marker within its genome, thereby selecting an IDC tolerant soybean plant or germplasm.

In some embodiments of this invention, a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, further wherein the IDC tolerance is exhibited as reduced yellow flash symptoms, and said marker is associated with reduced yellow flash symptoms in a soybean plant and comprises: (a) a G allele at SY0152AQ; (b) a G allele at SY0724AQ; (c) an insertion of nucleotide sequence CACACCTAGCTAAT (SEQ ID NO:301) at SY1154AQ; (e) an A allele at SY0153AQ; (f) an A allele at SY0781AQ; (g) a T allele at SY0322AQ; (h) a G allele at SY0370AQ; (i) a T allele at SY0372AQ; (j) a G allele at SY0373AQ; (k) a insertion of GGTAAG at SY0374AQ; (l) an A allele at SY0500AQ; (m) an A allele at SY0501AQ; (n) a G allele at SY0503AQ; (o) a G allele at SY0504AQ; (p) a G allele at SY0504AQ; or (q) any combination of (a) through (p) above, and selecting a progeny soybean plant or germplasm that possesses said marker within its genome, thereby selecting an IDC tolerant soybean plant or germplasm.

In other embodiments, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, further wherein the IDC tolerance is exhibited as recovery from yellow flash, and said marker is associated with recovery from yellow flash in a soybean plant and comprises: (a) a G allele at SY0152AQ; (b) a G allele at SY0724AQ; (c) a T allele at SY0224AQ; (d) a C allele at SY0225AQ; (e) a C allele at SY0226AQ; (f) an A allele at SY0326AQ; (g) a C allele at SY1018AQ; (h) an A allele at SY0991AQ; (i) an A allele at SY1000AQ; (j) a G allele at SY0784AQ; (k) a G allele at SY0328AQ; (l) an A allele at SY0815AQ; (m) an A allele at SY0078AQ; (n) a C allele at SY0132AQ; (o) an A allele at SY0816AQ; (p) a C allele at SY0079AQ; (q) an A allele at SY0079BQ; (r) a T allele at SY0420BQ; or (s) any combination of (a) through (r) above, and selecting a progeny soybean plant or germplasm that possesses said marker within its genome, thereby selecting an IDC tolerant soybean plant or germplasm.

In further embodiments, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, further w wherein the IDC tolerance is exhibited as reduced yellow flash symptoms and increased recovery from yellow flash, and said marker is associated with reduced yellow flash symptoms and recovery from yellow flash in a soybean plant and comprises: (a) a G allele at SY0152AQ; (b) a G allele at SY0724AQ; or (c) any combination of (a) and/or (b) above, and selecting a progeny soybean plant or germplasm that possesses said marker within its genome, thereby selecting an IDC tolerant soybean plant or germplasm.

In some embodiments, the second soybean plant or germplasm of this invention is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In additional embodiments of this invention, a method of introgressing a genetic marker associated with iron deficiency chlorosis (IDC) tolerance into a genetic background lacking said marker is provided, the method comprising: crossing a donor comprising said marker with a recurrent parent that lacks said marker; and backcrossing progeny comprising said marker with the recurrent parent, wherein said progeny are identified by detecting, in their genomes, the presence of a marker associated with IDC tolerance in a soybean plant, wherein said marker is located within a chromosomal interval of: (a) a chromosomal interval on chromosome 5 defined by and including a G allele at SY0152AQ and a G allele at SY0724AQ; (b) a chromosomal interval on chromosome 5 defined by and including an insertion of nucleotide sequence CACACCTAGCTAAT (SEQ ID NO:301) at SY1154AQ and an A allele at SY0153AQ; (c) a chromosomal interval on chromosome 2 defined by and including (i) a G allele at SY0781AQ and a T allele at SY0322AQ or (ii) an A allele at SY0781AQ and a T allele at SY0322AQ; (d) a chromosomal interval on chromosome 17 defined by and including (i) an A allele at SY0369AQ and an insertion of nucleotide sequence CTTACC at SY0374AQ or (ii) a G allele at SY0369AQ and an insertion of nucleotide sequence CTTACC at SY0374AQ; (e) a chromosomal interval on chromosome 12 defined by and including (i) a G allele at SY0498AQ and an A allele at SY0499AQ or (ii) an A allele at SY0498AQ and a G allele at SY0499AQ; (f) a chromosomal interval on chromosome 12 defined by and including (i) an A allele at SY0499AQ and a G allele at SY0504AQ or (ii) a G allele at SY0499AQ and an A allele at SY0504AQ; (g) a chromosomal interval on chromosome 14 defined by and including a T allele at SY0224AQ and a C allele at SY0226AQ; (h) a chromosomal interval on chromosome 2 defined by and including (i) an A allele at SY0325AQ and a G allele at SY0328AQ or (ii) a G allele at SY0325AQ and a G allele at SY0328AQ; (i) a chromosomal interval on chromosome 13 defined by and including (i) a G allele at SY0422AQ and a G allele at SY0425AQ or (ii) a C allele at SY0422AQ and an A allele at SY0425AQ; (j) a chromosomal interval on chromosome 13 defined by and including an A allele at SY0815AQ and a G allele at SY0422AQ; or (k) any combination of (a) through (j) above, thereby producing an IDC tolerant soybean plant or germplasm comprising said genetic marker associated with IDC tolerance in the genetic background of the recurrent parent, thereby introgressing the genetic marker associated with IDC tolerance into a genetic background lacking said marker.

In other embodiments, the present invention provides a method of introgressing a combination of genetic markers associated with iron deficiency chlorosis (IDC) tolerance into a genetic background lacking said combination of markers, comprising: crossing a donor comprising said combination of markers with a recurrent parent that lacks said combination of markers; and backcrossing progeny comprising said combination of markers with the recurrent parent, wherein said progeny are identified by detecting, in their genomes, the presence of said combination of markers associated with IDC tolerance in a soybean plant, wherein said combination of genetic markers comprises: (a) a G allele at SY0152AQ and a G allele at SY0724AQ; (b) an insertion of nucleotide sequence CACACCTAGCTAAT (SEQ ID NO:301) at SY1154AQ and an A allele at SY0153AQ; (c) a G allele at SY0781AQ and a T allele at SY0322AQ; (d) an A allele at SY0781AQ and a T allele at SY0322AQ; (e) an A allele at SY0369AQ and an insertion of nucleotide sequence CTTACC at SY0374AQ; (f) a G allele at SY0369AQ and an insertion of nucleotide sequence CTTACC at SY0374AQ; (g) an A allele at SY0369AQ, a G allele at SY0370AQ, a T allele at SY0372AQ, a G allele at SY0373AQ, an insertion of nucleotide sequence CTTACC at SY0374AQ, or any combination thereof; (h) a G allele at SY0369AQ, a G allele at SY0370AQ, a T allele at SY0372AQ, a G allele at SY0373AQ, an insertion of nucleotide sequence CTTACC at SY0374AQ, or any combination thereof; (i) a G allele at SY0498AQ and an A allele at SY0499AQ; (j) an A allele at SY0498AQ and a G allele at SY0499AQ; (k) an A allele at SY0499AQ, an A allele at SY0500AQ, an A allele at SY0501AQ, a G allele at SY0503AQ, a G allele at SY0504AQ, or any combination thereof; (l) a G allele at SY0499AQ, an A allele at SY0500AQ, an A allele at SY0501AQ, a G allele at SY0503AQ, a G allele at SY1333AQ, a G allele at SY0504AQ, or any combination thereof; (m) a T allele at SY0224AQ, a C allele at SY0225AQ, a C allele at SY0226AQ, or any combination thereof; (n) an A allele at SY0325AQ, an A allele at SY0326AQ, an C allele at SY1018AQ, an A allele at SY0991AQ, an A allele at SY1000AQ an G allele at SY0784AQ, a G allele at SY0328AQ, or any combination thereof; (o) a G allele at SY0325AQ, an A allele at SY0326AQ, a C allele at SY1018AQ, an A allele at SY0991AQ, an A allele at SY1000AQ, a G allele at SY0784AQ, a G allele at SY0328AQ, or any combination thereof; (p) a G allele at SY0422AQ, an A allele at SY1091AQ, a C allele at SY0133AQ, a G allele at SY0425AQ, or any combination thereof; (q) a C allele at SY0422AQ, a G allele at SY1091AQ, a G allele at SY1258AQ, a G allele at SY1259AQ, an A allele at SY0424CQ, an A allele at SY0425AQ, or any combination thereof; (r) a G allele at SY0370AQ and a G allele at SY0373AQ; (s) an A allele at SY1313AQ and a T allele at SY0372AQ; (t) an A allele at SY0326AQ and a G allele at SY0784AQ; (u) an A allele at SY0815AQ, an A allele at SY0078AQ, a C allele at SY0132AQ, an A allele at SY0816AQ, a C allele at SY0079AQ, an A allele at SY0079BQ, a T allele at SY0420BQ, a G allele at SY0422AQ, or any combination thereof; (v) an A allele at SY0815AQ, an A allele at SY0078AQ, an A allele at SY0132AQ, an A allele at SY0816AQ, a G allele at SY0079AQ, an A allele at SY0079BQ, an A allele at SY0420BQ, a G allele at SY0422AQ, or any combination thereof; or (w) any combination of (a) through (v) above, thereby producing an IDC tolerant soybean plant or germplasm comprising said combination of markers associated with IDC tolerance in the genetic background of the recurrent parent, thereby introgressing the combination of markers associated with IDC tolerance into a genetic background lacking said combination of markers.

In other embodiments, the present invention provides a method of introgressing a genetic marker associated with iron deficiency chlorosis (IDC) tolerance into a genetic background lacking said marker, comprising: crossing a donor comprising said marker with a recurrent parent that lacks said marker; and backcrossing progeny comprising said marker with the recurrent parent, wherein said progeny are identified by detecting, in their genomes, the presence of a marker associated with IDC tolerance in a soybean plant, wherein said marker comprises: (a) a G allele at SY0152AQ; (b) a G allele at SY0724AQ; (c) an insertion of nucleotide sequence CACACCTAGCTAAT (SEQ ID NO:301) at SY1154AQ; (d) an A allele at SY0153AQ; (e) a T allele at SY0322AQ; (f) an insertion of nucleotide sequence CTTACC at SY0374AQ; (g) a G allele at SY0370AQ; (h) a T allele at SY0372AQ; (i) a G allele at SY0373AQ; (j) an insertion of nucleotide sequence CTTACC at SY0374AQ; (k) an A allele at SY0500AQ, (l) an A allele at SY0501AQ; (m) a G allele at SY0503AQ; (n) a T allele at SY0224AQ; (o) a C allele at SY0225AQ; (p) a C allele at SY0226AQ; (q) an A allele at SY0326AQ; (r) an C allele at SY1018AQ; (s) an A allele at SY0991AQ; (t) an A allele at SY1000AQ; (u) an G allele at SY0784AQ; (v) a G allele at SY0328AQ; (w) a G allele at SY0370AQ; (x) a G allele at SY0373AQ; (y) an A allele at SY1313AQ; (z) a T allele at SY0372AQ; (aa) an A allele at SY0326AQ; (bb) a G allele at SY0784AQ; (cc) an A allele at SY0815AQ; (dd) an A allele at SY0078AQ; (ee) an A allele at SY0816AQ; (ff) an A allele at SY0079BQ; (gg) a G allele at SY0422AQ; or any combination of (a) through (gg) above; thereby producing an IDC tolerant soybean plant or germplasm comprising said marker associated with IDC tolerance in the genetic background of the recurrent parent, thereby introgressing said marker associated with IDC tolerance into a genetic background lacking said marker.

As described herein, the reduced yellow flash symptoms and/or recovery from yellow flash are exhibited by the soybean plant when the soybean plant is grown in calcareous soil having a pH greater than 7.5 and the marker, chromosome interval and/or combination of markers is associated with reduced yellow flash symptoms and/or recovery from yellow flash in a soybean plant when the soybean plant is grown in calcareous soil having a pH greater than 7.5.

Accordingly, some embodiments of the present invention provide a method of producing and/or selecting an iron deficiency chlorosis (IDC) tolerant soybean plant, wherein the IDC tolerance is exhibited as reduced yellow flash symptoms and/or recovery from yellow flash when the plant is grown in calcareous soil having a pH greater than 7.5, and the marker (e.g., SNP allele, combination of SNP alleles, SNP allele located in a chromosome interval) is associated with reduced yellow flash symptoms and/or recovery from yellow flash in a soybean plant grown in calcareous soil having a pH greater than 7.5.

The present invention provides soybean plants and germplasms having IDC tolerance. As discussed above, the methods of the present invention can be utilized to identify, produce and/or select a soybean plant or germplasm having IDC tolerance. In addition to the methods described above, a soybean plant or germplasm having IDC tolerance may be produced by any method whereby a marker associated with IDC tolerance (for example any one or more of the markers identified in Table 2) is introduced into the soybean plant or germplasm by such methods that include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having a genetic marker associated with IDC tolerance, obtainable by the methods of the presently disclosed subject matter, are aspects of the presently disclosed subject matter. The soybean plant, or part thereof, or soybean germplasm of this invention having a genetic marker associated with IDC tolerance can be heterozygous or homozygous for the genetic marker.

In some embodiments, the soybean plant or germplasm may be the progeny of a cross between an elite variety of soybean and a variety of soybean that comprises an allele associated with IDC tolerance. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The soybean plant or germplasm may be the progeny of an introgression wherein the recurrent parent is an elite variety of soybean and the donor comprises a genetic marker associated (e.g., SNP, combination of SNPs, SNP located in a chromosome interval) with IDC tolerance as described herein.

The soybean plant or germplasm may be the progeny of a cross between a first elite variety of soybean (e.g., a tester line) and the progeny of a cross between a second elite variety of soybean (e.g., a recurrent parent) and a variety of soybean that comprises a genetic marker associated with IDC tolerance as described herein (e.g., a donor).

The soybean plant or germplasm may be the progeny of a cross between a first elite variety of soybean and the progeny of an introgression wherein the recurrent parent is a second elite variety of soybean and the donor comprises a genetic marker associated with IDC tolerance.

Another aspect of the presently disclosed subject matter relates to a method of producing seeds that can be grown into IDC tolerant soybean plants. In some embodiments, the method comprises providing an IDC tolerant soybean plant of this invention (e.g. via use of IDC markers as disclosed in Table 2), crossing the IDC tolerant soybean plant with another soybean plant, and collecting seeds resulting from the cross, which when planted, produce IDC tolerant soybean plants.

Accordingly, the present invention provides improved soybean plants, seeds, and/or soybean tissue culture produced by the methods described herein.

In some embodiments, the presently disclosed subject matter provides methods for analyzing the genomes of soybean plants/germplasms to identify those that include desired markers associated with IDC tolerance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs capable of initiating DNA polymerization by a DNA polymerase on a *Glycine max* nucleic acid template to generate a *Glycine max* amplicon. In some embodiments, the *Glycine max* marker amplicon corresponds to *Glycine max* marker comprising a nucleotide sequence of any of SEQ ID NOs: 1-18, 55-136 and 302-323. In view of the disclosure of SEQ ID NOs: 1-18, 55-136 and 302-323as being linked to IDC tolerance loci, one of ordinary skill in the art would be aware of various techniques that could be employed to analyze the sequences of the corresponding soybean nucleic acids.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

QTL Mapping and Phenotyping Soybean Plant Material

Syngenta soybean plant materials were used to develop the iron deficiency chlorosis (IDC) quantitative trait loci (QTL) mapping populations. The parent populations were either IDC tolerant or IDC intolerant soybean materials based upon phenotyping of the population and knowledge of the germplasm. The parent materials classifications are provided in Table 3.

A connected structure of populations was fashioned from the parent materials (See, FIG. 1). Table 4 shows the generation, harvest method, timeline, and nursery location of the QTL population. Finally, checks were chosen based upon breeding experience and product knowledge. The phenotyping check classifications are listed in Table 5.

TABLE 3

Parent materials classifications

| Parental Material | IDC Tolerance Classification |
|---|---|
| 03DL052038 | Tolerant |
| 04KL108888 | Tolerant |
| 9378 | Intolerant |
| 1162 | Intolerant |
| 9428 | Intolerant |
| 5763 | Intolerant |
| 1519 | Intolerant |
| 1531 | Intolerant |

TABLE 4

Population development

| Generation | Harvest Method | Timeline |
|---|---|---|
| Crossing | Bulk | Summer Year 1 |
| F1 Plants | Bulk | Fall Year 1-Winter Year 2 |
| F2 Plants | SSD* | Spring Year 2 |
| F3 Plants | SSD* | Summer Year 2 |
| F4 Plants | Plant pull | Fall Year 2-Winter Year 3 |

*SSD = Single Seed Descent

TABLE 5

IDC phenotyping of check populations.

| Tolerant Checks | Intolerant Checks |
|---|---|
| 03DL052038 | 1107 |
| 2251 | 8295 |

TABLE 5-continued

IDC phenotyping of check populations.

| Tolerant Checks | Intolerant Checks |
|---|---|
| 4015 | 8413 |
| 8047 | 8851 |
| 0011 | 1285 |

Example 2

Experiment Design and Phenotyping

The eleven F4 populations as shown in FIG. 1 were arranged into eleven—two replicate, three location, IDC phenotyping experiments. The same ten phenotyping checks/controls were used in all experiments. The experimental design was Randomized Complete Block (RCB), which also included a repeating intolerant check (material 8314) occurring every 10th hill.

The three planting locations were used: Truman, Minn.; Ogden, Iowa; and Fort Dodge, Iowa. The field area at each site was prepared with a 48 inch wide rotary tiller just prior to planting to remove compaction.

The plots were kept weed free throughout the life of the experiment; however, no Post-Emergence herbicide was used. The planter's four row units were spaced 10 inches apart and the hills were placed every 15 inches down the row to minimize the field size needed. Six seeds per hill (replicates) were planted. The 12 experiments were contiguously arranged in a block. Experimental replicates were blocked and mapped adjacent to each other. The hills within replicates were arranged in a serpentine fashion Plants were evaluated for IDC visually and by electronic scanning (radiometer). Table 6, below, summarizes the trait codes, description, type, minimum and maximum values for each type of measurement, and the calculation (formula) when applicable that were used in the evaluations. At approximately the V2 stage of growth, the hills were visually rated and canopy reflectance measured (or NDVI (Normalized Difference Vegetation Index)) with a Greenseeker® RT100 radiometer. The visual rating and NDVI measurement were repeated 14 days later. These times, V2 stage and 14 days later, correspond to IDC yellow flash symptom and recovery reaction times, respectively.

As shown in Table 6, ICFLR and ICFLN are codes that identify the Yellow Flash ratings for visual and radiometer, respectively. Likewise, ICR_R and ICR_N are codes that identify the Recovery for the visual ratings and the radiometer number, respectively. IC_R and IC_N are codes that identify the mean of the yellow flash and recovery data for the visual ratings and the radiometer number, respectively. The visual ratings scale was 1-9 with 1 being the best (no chlorosis) and 9 being the worst (plant death). Arithmetic averages of the visual and radiometer traits were calculated. Table 7 shows the results of a single experiment.

TABLE 6

Phenotyping Traits

| Trait Code | Description | Type of Measurement | Type of Measurement* | Minimum Value | Maximum Value | Calculation |
|---|---|---|---|---|---|---|
| IC_N | Mean of Flash and Recovery | Radiometry | Measured | 0 | 1 | ICFLN + ICR_N)/2 |
| IC_R | Mean of Flash and Recovery | Visual | Measured | 1 | 9 | ICFLR + ICR_R)/2 |
| IC_AN | Mean of Flash and Recovery | Radiometry | Adjusted | 0 | 1 | ICFAN + ICR_AN)/2 |
| IC_AR | Mean of Flash and Recovery | Visual | Adjusted | 1 | 9 | ICFAR + ICR_AR)/2 |
| ICFAN | Flash | Radiometry | Adjusted | 0 | 1 | |
| ICFAR | Flash | Visual | Adjusted | 1 | 9 | |
| ICFLN | Flash | Radiometry | Measured | 0 | 1 | |
| ICFLR | Flash | Visual | Measured | 1 | 9 | |
| ICR_N | Recovery | Radiometry | Measured | 0 | 1 | |
| ICR_R | Recovery | Visual | Measured | 1 | 9 | |
| ICRAN | Recovery | Radiometry | Adjusted | 0 | 1 | |
| ICRAR | Recovery | Visual | Adjusted | 1 | 9 | |

*Indicates whether the phenotypic data was adjusted by the surface analysis utility as discussed in Example 5.

TABLE 7

Phenotyping results from a single experiment (sorted by IC_R).

| | | Visual | | | Radiometer | | |
|---|---|---|---|---|---|---|---|
| ENTRY | Material | IC_R | ICFLR | ICR_R | IC_N | ICFLN | ICR_N |
| 42 | 03DL052038 Tolerant Control | 1.7 | 2.2 | 0.6 | 0.474 | 0.441 | 0.514 |
| 21 | | 2 | 2.5 | 0.9 | 0.473 | 0.466 | 0.509 |
| 3 | | 2.2 | 2.7 | 0.9 | 0.455 | 0.399 | 0.514 |
| 20 | | 2.2 | 2.9 | 0.6 | 0.415 | 0.408 | 0.452 |
| 37 | 2251 Tolerant Control | 2.2 | 2.5 | 1.3 | 0.469 | 0.447 | 0.507 |
| 16 | | 2.7 | 2.4 | 2.3 | 0.454 | 0.45 | 0.495 |
| 44 | 4015 Tolerant Control | 3 | 3 | 1.9 | 0.415 | 0.398 | 0.49 |
| 8 | | 3 | 3.7 | 1.3 | 0.447 | 0.453 | 0.475 |
| 39 | 8047 Tolerant Control | 3 | 3.5 | 1.6 | 0.389 | 0.376 | 0.457 |
| 31 | | 3.5 | 4 | 1.9 | 0.433 | 0.369 | 0.495 |

TABLE 7-continued

Phenotyping results from a single experiment (sorted by IC_R).

| ENTRY | Material | Visual | | | Radiometer | | |
|---|---|---|---|---|---|---|---|
| | | IC_R | ICFLR | ICR_R | IC_N | ICFLN | ICR_N |
| 14 | | 3.7 | 4.4 | 1.6 | 0.448 | 0.444 | 0.48 |
| 33 | 0011 Tolerant Control | 3.7 | 3.1 | 3.6 | 0.171 | 0.177 | 0.164 |
| 13 | | 3.8 | 4.5 | 1.9 | 0.397 | 0.392 | 0.445 |
| 30 | | 3.8 | 4.2 | 2.6 | 0.308 | 0.382 | 0.276 |
| 22 | | 4 | 4.3 | 2.6 | 0.398 | 0.404 | 0.437 |
| 35 | | 4 | 4.1 | 2.6 | 0.462 | 0.469 | 0.508 |
| 7 | | 4.3 | 3.7 | 3.9 | 0.435 | 0.468 | 0.455 |
| 5 | | 4.3 | 4.2 | 3.3 | 0.379 | 0.417 | 0.38 |
| 10 | | 4.3 | 4.5 | 3.3 | 0.395 | 0.417 | 0.409 |
| 15 | | 4.5 | 4.4 | 3.3 | 0.417 | 0.435 | 0.461 |
| 19 | | 4.5 | 4.8 | 2.9 | 0.383 | 0.388 | 0.425 |
| 4 | | 4.7 | 4.8 | 3.6 | 0.37 | 0.368 | 0.397 |
| 6 | | 4.7 | 5 | 2.9 | 0.275 | 0.43 | 0.173 |
| 24 | | 4.7 | 4.2 | 3.9 | 0.319 | 0.382 | 0.351 |
| 18 | | 5 | 5.2 | 3.6 | 0.322 | 0.351 | 0.337 |
| 2 | | 5.2 | 5.2 | 3.9 | 0.355 | 0.383 | 0.408 |
| 32 | | 5.3 | 4.7 | 4.6 | 0.319 | 0.378 | 0.345 |
| 36 | | 5.3 | 5.2 | 4.3 | 0.23 | 0.283 | 0.2 |
| 9 | | 5.5 | 5 | 4.6 | 0.397 | 0.365 | 0.461 |
| 17 | | 5.5 | 4.5 | 5.3 | 0.336 | 0.352 | 0.371 |
| 27 | | 5.5 | 4.7 | 4.9 | 0.38 | 0.41 | 0.417 |
| 25 | | 5.8 | 5.5 | 4.6 | 0.335 | 0.378 | 0.359 |
| 28 | | 5.8 | 5 | 5.3 | 0.351 | 0.381 | 0.385 |
| 40 | 1107 Intolerant Control | 5.8 | 5.7 | 4.9 | 0.331 | 0.355 | 0.353 |
| 29 | | 6 | 6.2 | 4.6 | 0.34 | 0.367 | 0.389 |
| 11 | | 6.2 | 4.9 | 6.3 | 0.235 | 0.291 | 0.301 |
| 41 | 8295 Intolerant Control | 6.2 | 5.8 | 5.6 | 0.325 | 0.376 | 0.352 |
| 1 | 8413 Intolerant Control | 6.2 | 5.1 | 5.5 | 0.345 | 0.392 | 0.37 |
| 26 | | 6.3 | 5.2 | 5.9 | 0.224 | 0.31 | 0.255 |
| 43 | 8851 Intolerant Control | 6.3 | 5.9 | 5.9 | 0.271 | 0.322 | 0.295 |
| 38 | 1285 Intolerant Control | 6.7 | 5.5 | 6.6 | 0.238 | 0.248 | 0.257 |
| | Mean General | 4.6 | 4.4 | 3.6 | 0.362 | 0.384 | 0.391 |
| | Mean Control | 2.7 | 2.9 | 1.8 | 0.383 | 0.368 | 0.426 |
| | Trials w/data | 2 | 3 | 2 | 2 | 3 | 2 |
| | Entries w/data | 41 | 41 | 41 | 41 | 41 | 41 |
| | LSD General (5%) EE | 2 | 1.5 | 2.8 | 0.161 | 0.106 | |
| | LSD* Control (5%) EC | 1.5 | 1.1 | 2.1 | 0.125 | 0.082 | |
| | CV** (Effective) % | 22 | 19.1 | 39.4 | 22.175 | 16.957 | 31.129 |

*LSD = Least significant different;
**CV = Coefficient of Variation

The IDC phenotyping results in Table 7 indicate that at 95% confidence level, significant differences were detected between materials/entries. LSD General (5%) EE and LSD Control (5%) EC statistics allow entry to entry or entry to control comparisons, respectively. The results also indicate that significant differences are detected in the traits within visual and radiometer phenotyping.

Example 3

Classification of IDC Prone Soils

Soil samples were collected from eight IDC phenotyping locations in Nebraska, Iowa, Minnesota and North Dakota. These samples were collected from field spots in which non-IDC tolerant soybean plants show IDC symptoms. These soils samples were analyzed for standard soil nutrients, salts, and pH at Mid-West Laboratories, Omaha Neb. The data from these soil samples was analyzed for Principal Component Analysis (PCA). PCA is a multivariate analysis which can be used to reveal patterns or clusters in multivariate data. Principal component 1 and Principal component 2 revealed two main distinct clusters for these soil samples. Soils samples collected from Iowa-Southern Minnesota and North Dakota-Northern Minnesota were grouped in two distinct clusters. A location from Nebraska did not group with any of these two clusters. This analysis indicated that soil conditions and their properties which cause IDC can be grouped into three classes—Iowa-Southern Minnesota type soils, North Dakota-Northern Minnesota type soils and Nebraska type soils.

Example 4

Genotyping of the IDC QTL Population

All parents of the populations identified in Example 1 were fingerprinted with genome wide SNP markers. The fingerprinting data on the parents was used to determine polymorphic SNPs for each population. Only suitable polymorphic SNPs were genotyped for each population. Table 8 provides the number of markers used to genotype each population.

TABLE 8

The number of genotyping markers.

| Population Number | Pedigree | Number of recombinant inbred lines (RILs) | Number of SNPs |
|---|---|---|---|
| 1 | 04KL108888/9428 | 60 | 193 |
| 2 | 04KL108888/1162 | 29 | 195 |

TABLE 8-continued

The number of genotyping markers.

| Population Number | Pedigree | Number of recombinant inbred lines (RILs) | Number of SNPs |
|---|---|---|---|
| 3 | 9378/03DL052038 | 80 | 192 |
| 4 | 5763/03DL052038 | 81 | 202 |
| 5 | 1519/03DL052038 | 53 | 147 |
| 6 | 9428/03DL052038 | 52 | 183 |
| 7 | 1531/03DL052038 | 64 | 153 |
| 8 | 1162/1519 | 85 | 199 |
| 9 | 9378/9428 | 45 | 54 |
| 10 | 1531/9378 | 83 | 132 |
| 11 | 1531/1162 | 41 | 132 |

The tissue of recombinant inbred lines (RILs) was obtained by growing them in the field or greenhouse. DNA was extracted from the leaf tissue of 7-10 day old seedlings (7-10 days after planting). DNA can be extracted from plant tissue in any way known in the art, including the CTAB (hexadecyltrimethylammonium bromide) method (See, e.g., Stewart et al., *BioTechniques* 14(5):748-749 (1993)), sodium hydroxide, and the Dellaporta method (Dellaporta et al., *Plant Mol. Biol. Rep.* 1:19-21 (1983)). See also, Sambrook & Russell *Molecular Cloning: A Laboratory Manual, Third Edition*, Cold Spring Harbor Laboratory Press, Cold Spring Harbor, N.Y., United States of America (2001)) for additional DNA extraction methods. DNA is diluted in TE buffer and stored at 4° C. until used in PCR reactions as described below in Table 9.

TABLE 9

PCR was set up in 5 μl final volumes according to the following formula.

| Reagent | Stock concentration | Per reaction (μl) | For 96 samples (μl) | Final concentration |
|---|---|---|---|---|
| 2X Master Mix (JumpStart™ Taq ReadyMix™) | 2X | 2.5 | 296.88 | 1X |
| AbD primer/probe mix (80x) | 40x | .0625 | 6 | 0.5x |
| PCR-quality H2O | — | 2.44 | 234.24 | — |
| DNA (dried in 384) | 4.5 ng/μl | 4 | — | 3.6 ng/ul (18 ng) |
| Final Volume (ul) | | 5.00 | 357.44 | |

The Master Mix is JumpStart™ Taq ReadyMix™ (Sigma Catalogue No. 2893; Sigma Chemical Co., St. Louis, Mo., United States of America), a premix of all the components, including nucleotides and Taq polymerase (but not primers and/or probes) necessary to perform a 5'-nuclease assay. Before use, 1375 μl of 1.0 M $MgCl_2$ (Sigma Catalogue No. M1028) and 250 μl of 300 μM Sulforhodamine 101 (Sigma Catalogue No. S7635), also known as ROX, are added to a 125 mL bottle of JumpStart™ Taq ReadyMix™. PCR plates were placed in an ABI 9700 thermal cycler and the program set forth in Table 10 was run:

TABLE 10

PCR program.

| Task | SNP1 |
|---|---|
| Initial denaturation | 50° C. for 2 min; followed by 95° C. for 10 min |
| Cycles | 95° C. for 15 sec |
| | 60° C. for 1 min |
| Number of cycles | 40 |
| Final elongation | 72° C. for 5 min |
| Hold | Hold at 4° C. |

The ABI 7900 Sequence Detection System (or Taqman®) was used to visualize the results of an allelic discrimination (SNP) assay. Using the Sequence Detection System (SDS) software, allele calls were made based on the fluorescence for the two dyes measured in each sample.

Example 5

Phenotypic Data Analysis

The raw data was analyzed using fixed effects analysis of variance (ANOVA), with the traits and populations kept separate. Populations were phenotyped with two replicates at two locations in Iowa. The model below was used, allowing testing for material ID*location interactions. Least square means within and across locations used as phenotype variables for Quantitative Trait Locus (QTL) analysis.

IDC trait=location+material ID+material ID*location+error.

Since the potential severity of IDC is related to spatially variable soil properties, statistical methods that can reduce the effects of this variability are important to increase the ability to detect QTL. Software containing a surface analysis utility was used to perform spatial adjustments based on the phenotype of a repeated check planted throughout the evaluation trial. This tool was used as a way to reduce spatial effects caused by differing potentials for IDC development across different areas of the phenotyping locations. If surface analysis could not detect the spatial patterns in phenotypic data, it returned the original, measured values. This leads to high correlations between the original measured and surface adjusted values. Therefore, comparisons between measured and surface analysis adjusted phenotype data were performed using pair-wise correlations of means across locations in the statistical analysis software package, JMP.

Across the mapping populations, 62 out of 66 comparisons (representing different combinations of IDC trait (e.g., yellow flash, recovery and mean)) had correlations of 0.98, 0.99, or 1.0. The remaining four comparisons were all from one mapping population. They had correlation coefficients ranging from 0.29 to 0.94. Regardless of the level of correlation, all traits whether surface-analyzed or from ANOVA were used in the QTL analysis.

Example 6

QTL Analysis Using Network Population Mapping (NPM)

To detect QTLs for IDC tolerance, Network Population Mapping analysis was performed using Syngenta software and analysis method (See, US Patent Publication No. 20100269216). This method is superior to standard biparental QTL mapping in that it uses multiple mapping populations (termed connected networks) that are designed so that the mapping parents are used in multiple populations. This design results in greater statistical power to detect QTL, since individuals across all populations are used for testing for the presence of QTL.

The population network was analyzed using the NPM method, with 1000 permutations performed to empirically determine a 0.05 significance threshold for every trait, rather than arbitrarily choosing a significance threshold. In the final analysis, trait-location combinations with very low heritability of 0.2 or less were excluded from some populations, which increased the number and significance of detected QTL.

The raw results from NPM analysis were processed using an internally developed SAS script. The output from the script was used to create summarized reports for QTL that passed the permutation test.

The network detected multiple QTL across the soy genome. Two important values in QTL studies are the LOD (logarithm of odds) and $R^2$. A higher LOD value represents greater statistical evidence for the presence of a QTL, and a higher $R^2$ indicates that the particular QTL has more effect on the trait of interest. The maximum LOD was 20.3, and the maximum $R^2$ was 0.65.

Example 7

Selecting QTL of High Confidence

From the large number of QTL observed, a subset of high confidence QTL was selected. For example, in one case, QTL could be found for only one trait-location combination at a marginal significance level, and would thus be of limited utility for marker-assisted breeding. Thus, this QTL was not included in the high confidence subset. In other cases, QTL were found that had a marginal LOD score but a suspiciously high $R^2$ value.

Thus, the following criteria were used to prioritize QTL regions and QTL were retained if:

(1) they had a LOD score of 2.7 or greater with a reasonable $R^2$, (2) were observed in more than one phenotyping location, or (3) were observed for multiple correlated traits in the same genomic region at one or more phenotyping locations.

Based on the criteria outlined above, only those QTL that were of a high confidence were considered further.

Example 8

Validation of the Utility of the QTLs Associated with IDC

Eighteen candidate validation populations were made between soybean varieties to determine the utility of these QTLs in improving the tolerance to iron deficiency chlorosis in soybean.

Out of these 18 populations, 12 were selected for validation based on their relationship to the parents of the discovery populations and numbers of segregating QTL. F3 progenies of the 12 populations were genotyped as described in Example 4 using marker assays flanking QTL (only QTL of very high confidence identified in Example 7 were used). For each population, 1380 F3 progenies were genotyped. Out of these 1380 progenies some were selected based on their QTL status. Selected progenies are evaluated for IDC at four locations in Iowa and Minnesota as per the Example 2.

Standard statistical analyses are conducted to determine the performance of the QTL in selection for progeny having tolerance to IDC.

The list of SNP markers comprising the QTL of the present invention is provided in Table 2, above.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of producing a soybean plant tolerant to iron deficiency chlorosis (IDC), comprising the steps of:
   (a) isolating a nucleic acid from a soybean plant or part thereof;
   (b) detecting in said nucleic acid, the presence of a plurality of single nucleotide polymorphism (SNP) markers associated with IDC tolerance in a soybean plant, wherein said markers are located within a chromosomal interval comprising physical positions 1035989-1401213 on Soybean chromosome 5, and further wherein said chromosomal interval comprises (i) a G allele at SY0152AQ; (ii) a G allele at SY0723BQ; (iii) a G allele at SY0724AQ; (iv) a SEQ ID NO: 301 insertion at SY1154AQ; and (v) an A allele at SY0153AQ as described in Table 2;
   (c) identifying and/or selecting an iron deficiency chlorosis (IDC) tolerant soybean plant or part thereof;
   (d) crossing the soybean plant of (c) with a second soybean plant not having said plurality of markers of step (b) in its genome;
   (e) collecting seed from the cross in step (d); and
   (f) growing a progeny soybean plant from said seed which comprises said plurality of markers in its genome, thereby producing a soybean plant with increased tolerance to IDC relative to a soybean plant not comprising said plurality of markers;
   wherein said plurality of markers identifies a soybean plant comprising all of SNP alleles (i)-(v).

2. The method of claim 1, wherein said chromosomal interval positions of (b) correspond to the reference genome of Williams 82.

3. The method of claim 1, wherein the nucleic acid of (b) comprises SEQ ID NOs: 1-4 and 55.

4. The method of claim 1, wherein a plant not tolerant to IDC is selected in the absence of any one of (i) a G allele at SY0152AQ; (ii) a G allele at SY0723BQ; (iii) a G allele at SY0724AQ; (iv) a SEQ ID NO: 301 insertion at SY 1154AQ; and (v) an allele at SY0153AQ as described in Table 2.

5. The method of claim 1 wherein IDC tolerance is exhibited by reduced yellow flash symptoms.

6. The method of claim 3, wherein the iron deficiency chlorosis (IDC) tolerant soybean plant or part thereof is identified through use of any one of nucleotide probes comprising a nucleotide sequence as depicted in any one of SEQ ID NOs: 19-22; 37-40; 137 and 219.

7. The method of claim 3, wherein the iron deficiency chlorosis (IDC) tolerant soybean or part thereof is identified through use of a PCR primer pair that anneals to any one of SEQ ID NOs: 1-4 or 55, wherein the primer pair is capable of initiating DNA polymerization by a DNA polymerase on a *Glycine max* nucleic acid template to generate a *Glycine max* amplicon.

8. The method of claim 7, wherein the amplicon comprises a nucleotide sequence that is distinguishing for the presence or absence of alleles selected from the group consisting of: (i) a G allele at SY0152AQ; (ii) a G allele at SY0723BQ; (iii) a G allele at SY0724AQ; (iv) a SEQ ID NO: 301 insertion at SY 1154AQ; (v) an A allele at SY0153AQ and any combination of (i) through (v).

* * * * *